(12) United States Patent
Ling et al.

(10) Patent No.: US 6,830,913 B1
(45) Date of Patent: Dec. 14, 2004

(54) ABCB9 TRANSPORTER AND USES THEREOF

(75) Inventors: Victor Ling, Vancouver (CA); Michelle L. Pollard, Vancouver (CA); Bruce P. Connop, Vancouver (CA); Fang Zhang, Victoria (CA)

(73) Assignee: Active Pass Pharmaceuticals, Inc., Vancouver (CA)

( * ) Notice: Subject to any disclaimer, the term of this patent is extended or adjusted under 35 U.S.C. 154(b) by 477 days.

(21) Appl. No.: 09/724,653

(22) Filed: Nov. 28, 2000

(Under 37 CFR 1.47)

Related U.S. Application Data

(60) Provisional application No. 60/167,930, filed on Nov. 29, 1999.

(51) Int. Cl.[7] .......................... C12N 9/00; C12N 15/09; C12N 9/10; C12N 9/14; C12N 1/20; C12N 15/00; C07K 1/00; C07H 21/04
(52) U.S. Cl. ...................... 435/196; 435/69.1; 435/183; 435/193; 435/194; 435/195; 435/252.3; 435/320.1; 530/350; 536/23.2; 536/23.4; 536/23.5
(58) Field of Search .......................... 435/69.1, 252.3, 435/320.1, 183–196; 536/23.2, 23.4, 23.5; 530/350

(56) References Cited

FOREIGN PATENT DOCUMENTS

| WO | WO 00/11014 | 3/2000 |
|---|---|---|
| WO | WO 00/18912 | 4/2000 |

OTHER PUBLICATIONS

Allikmets et al., "Characterization of the human ABC superfamily: isolation and mapping of 21 new genes using the expressed sequence tags database," Human Molecular Genetics 5(10):1649–1655, Oct. 1996.

Kobayashi et al., "A half–type ABC transporter TAPL is highly conserved between rodent and man, and the human gene is not responsive to interferon–gamma in contrast to TAP1 and TAP2," Journal of Biochemistry (Tokyo) 128(4):711–718, Oct. 2000.

Yamaguchi et al., "An ABC transporter homologous to TAP proteins," FEBS Letters 457(2):231–236, Aug. 27, 1999.

Zhang et al., "Characterization of ABCB9, an ATP binding cassette protein associated with lysosomes," Journal of Biological Chemistry 275(30):23287–23294, Jul. 28, 2000.

GenBank Accession No. AB027520, Jan. 8, 2000., Yamaguchi et al.

GenBank Accession No. AB045381, Jul. 29, 2000., Maeda et al.

GenBank Accession No. AB045382, Jul. 29, 2000, Maeda et al.

GenBank Accession No. AF216494, Aug. 1, 2000., Zhang et al.

GenBank Accession No. AF216495, Aug. 1, 2000, Zhang et al.

GenBank Accession No. AI206549, Oct. 16, 1998, NCI–C-GAP.

GenBank Accession No. CAD08921, Oct. 25, 2001, Parkhill et al.

GenBank Accession No. F06569, Feb. 20, 1995, Auffray et al.

Fisher, "Isolation and Characterization of a Novel Member of the ATP–Binding Cassette Superfamily in Humans," master's thesis, University of Torontol, Ontario, Canada, 1996, pp. 1–77.

Luciani et al. "Cloning of two novel ABC transportes mapping on human chromosome 9," *Genomics* 21(1):150–159, May 1, 1994.

Patel and Latterich, "The AAA team: related ATPases with diverse functions," *Trends Cell Biol.* 8(2):65–71, Feb. 1998.

*Primary Examiner*—Manjunath Rao
(74) *Attorney, Agent, or Firm*—Seed Intellectual Property Law Group PLLC

(57) ABSTRACT

The invention provides isolated nucleic acid molecules, designated ABCB9 transporter nucleic acid molecules, which encode novel ABC transporter family members. The invention also provides antisense nucleic acid molecules, recombinant expression vectors containing ABCB9 transporter nucleic acid molecules, host cells into which the expression vectors have been introduced, and nonhuman transgenic animals in which an ABCB9 transporter gene has been introduced or disrupted. The invention still further provides isolated ABCB9 transporter proteins, fusion proteins, antigenic peptides, anti-ABCB9 transporter antibodies, and screening assays for ABCB9 transporter modulators. Diagnostic and therapeutic methods utilizing compositions of the invention are also provided.

15 Claims, 8 Drawing Sheets

ABCB9 nucleotide sequence

```
CGCCCGGGCAGGTCAGCCTGTCTCAAGGCACGCCAGTCTCAGCTCCGACCTTGCAGCCTCCGACCTTGCAGCGGCGCAGCCGCGGGTGGGAGGTGGGAGGAGCAGCGGGAA
GAGCGGAGCGAGGACCCGGTCCGGGCAGTCTTCAATGAGCAGCCGGGAAACTGCACCCAGAACCCGAGCCTGCTGCCGCGCCCCTCCCAGAGCTC
ACCTGGTGCCAGGTAACAGGCCTGGCCTGCCCTGTGATGATGGCCTTGCCCCCGTGAGCTACAACCTGGCCTTCAGCACCCGCCACCTCC
AACCAGCAGGAAGGGGCTGTGTGGAGGACATCCGCACCTTCAACATCTTTGACTCGGTCGGATCTCTGGGCAGCCTGCCTGTTACCGCAGCTGCCTGCT
CCTGGGAGCCGCAGCCACCATTGTGTGTGGCCAAGAACAGTGCGCTGCTCTTCTCTTGGGGACCCCTCGTGCGCCCTCGGTCATCCGTGTGCCTCTTCGT
GCTGGGAGCATCTATGCCATGGTGAAGCTGTGCTTCTCAGAGGTGCCAGGCCCATCCGGGACCCTGGTTTTGGGCCTGTTGTGTGGACGTACAT
TTCACTCGGCGCATCCTTCTCGGGAGCGGCGGCCCGGGCCACCGCTGTCTGGAGACCTGTCCTACACCAAGCCCGAGCCTGGCCTTCCTCGT
CTTCCCTGGGAGCGGCGGCCCGGCCACCGCTGTCTGGAGACCTGTCCTACACCAAGCCCGAGCCTGGCCTTCCTCGT
GGCCGCTCCTTCTTCCTCATCGTGTGCCTGCAGCCTCTGGCCATTGCCCGCCAGTGTATTCGGGCGCAGTATTCGGGCGCAGGTTTTACCCTCAT
CATGGATCAGTTCAGCACACGGCTTCGCCTTCGAACATTCGAAACTGTCGTCTCCAGAACATCAATGTCTTCCTGCGGAACACAGTCAAGGTCACGGGCGT
ATTTGCCAGACTGAACATTCGACCTCGGACACCACCTGGTCAGCAGCTGTCTCCAGAACATCAATGTCTTCCTGCGGAACACAGTCAAGGTCACGGGCGT
CATCTCCCGCCCTGACTTCATGTTCAGCTGTCAGCTTCATGGGCTTCCACCTTCGGTCATCAGTGTGTCAACATCATCTACGGCAAGTA
GGTGGTCTTCATGTTCAGCTGTCAGCTTCATGGGCTTCCACCTTCGGTCATCAGTGTGTCAACATCATCTACGGCAAGTA
CTACAAGAGGCTCTCCAAAGAGTCAGAGCCCAGAATGCCCAGAGTCCAGAATGCCCAGAGTCCAGAATGTGCCATGGCAGCCATCAGTGCCAGTGCCATGGCAGCCATCAGTGCCTACATGTCCGGAGCTT
CGCCAATGAGGAGGAGAGGAGCCAGAGTGTACCTGCAGCAGTGTACAGGGGCAGTGATCTCCTCTACGGGGCCAAGCTGTACCAGCGGCAACCT
CTGGGCAGCCAGCGGCTCACACTGTCGGTTGTGTCCAGATTGTATGGAGTCCGTGGGCAGCTCCGTGTCATCTCCGGCCTGATGCAGGAGTGGGGCTGTGA
CATCATCTTCATCATCTTCATCATCTACGAGTTTCATCGACCGGCAGCGACCATGGTGCACCACCCAGTCCTCGAGAACTTCTACCCCCTGTCCT
GAAGGTGTTGATTCATGACCGGCAGCGACCATGGTGCACCACCCAGTCCTCGAGAACTTCTACCCCCTGTCCTTGCCCCTGAGGGCCGGGTGGCAGCTTGAGGCACCTGGACTTTGAGAATGT
GACCCTTCACCTACCGCACTCGGCCCCACACCCAGTCCTGTGTCAACATCTGTGAGAACTTCTACCCCCTGTCCTTGCCCCTGAGGGCCGGGTGGCAGCTTGAGGCACCTGGACTTTGAGAATGT
GGGCAGTGGAAGGGCGCCTTTGCTGCCCAGTGTCAGGTGGTCCGAGAGCGAGATCTGATCCGAGAAGCAGCGGGTGGCCGGCAGCATCAGCAGAGACAG
CCACCACAAGTACCTTGCACCGTGGTGGTCAGGTGGTCCGAGAGCGAGATCTGATCCGAGAAGCAGCGGGTGGCCGGCAGCATCAGCAGAGACAG
GGGAGAAGGGCGCCTTTGATGCCAGTGCTGCCAGGTATCTGATCGCAGAAGCAGCGGGTGGCCGAACCCCAGCCGCACACACAGTCCTCAGCAGCCG
TGAGCACCGTGGAGCACGCGCACTCATTGTGCTGGACAAGGCCGGTAGTGCTGGACAGCAGCGCCAGGGCCCACCACCAGCAGCCGGGCCAGGGCCAGGGCCC
TCTACGCCAAGCTGGTGTGCAGCGGCAGCAGCAGGCTTCAGCC[CCC]GCCGCAGACTTCACGACTGTGGGCTTGACAGATGCTGCCAGCTGCCACCAACGGCAGTCAC
```

FIG. 1-1

AAGGCCTGATGGGGGGCCCCCTGCTTCTCCGGTGGGGCAGAGGACCCGGTGCCTGCTGGCAGATGTGCCACGGAGGCCCCCAGCTGCCCTCCGA
GCCCAGGCCTGCAGCACTGAAAGACGACCTGCCATGTCCCATGGATCACCGCTTCCTGCATCTGCCCTGGTCCCTGCCCCATTCCCAGGCACT
CCTTACCCCTGCTGCCCTGAGCCCAACGCCTTCACGGACCCCTCCAGCCTCCTAAGCAAAGGTAGAGCTGCCTTTAAACCTAGGTCTTACCAGGG
TTTTTACTGTGTTTGGTTGAGCCAGCACCCAGTCAACTCCTAGATTTCAAAAACCTTTTCTAATTGGGAGTAAGCTGCACTTTCACCAAGATGTT
CTAGAAACTTCTGAGCCAGGAGTGAATGGCCCTTCCAGAGACTAGGCCTCTCCCCTTTACCCTCCAGAGAAGGG
GCTTCCCTGTCCCGGAGGACACGGGGAACGGGGATTTTCCGTCTCTTGTGAGTCTGTGGCCAGGCGGGTAGGGAGCGTGGAG
GGCATCTGTCTGCCATCGCCCCGCTGCCAATCTAAGCCAGTCTCACTGTGAACCACACGAAACCTCAACTGGGGGAGTGAGGGGCTGGCCAGTCTG
GAGGGCCTCAGGGGTGCCAGGCCACGTGGATGTTCATGAGATGTCATTCTGCCCCACCCCTGTCTCTTCGCCACCCCTCCCCAAGCCCGGCCCCTGT
CAGAGGTTGCAACATGTTGAGAGAACCCGGTCAATAAAGTGTACTACCCTCTTACCCCTAAAAAAAAAAAAAAAAAAAAAA

AGG[X]C  Translation initiation motif
ATG  Translation initiation codon
TGA  Translation termination codon
AATAAA  Polyadenylation signal The nucleotide sequences of the ESTs R25718 and F06569 are in brackets and underlined, respectively.

*FIG. 1-2*

ABCB9 amino acid sequence

MRLWKAVVTLAFMSVDICVTTAIYVFSHLDRSLLEDIRHFNIFDSVLDLWAACLYRSCLLLGATIGVAKNSALGPRRLRASWLVITLVCLFVGIY
AMVKLLLFSEVRRPIRDPWFWALFVWTYISLGASFLLWWLLSTVRPGTQALEPGAATEAEGFPGSGRPPPEQASGATLQKLLSYTKPDVAFLVAAS
FFLIVAALGETFLPYYTGRAIDGIVIQKSMDQFSTAVVIVCLLAIGSSFAAGIRGGIFTLIFARLNIRLRNCLFRSLVSQETSFFDENRTGDLISR
LTSDTTMVSDLVSQNINVFLRNTVKVTGVVVEMFSLSWQLSLVTFMGFPIIMMVSNIYGKYKRLSKEVQNALARASNTAEETISAMKTVRSFANE
EEEAEVYLRKLQQVYKLNRKEAAAYMYVWGSGLTLLVVQVSILYYGGHLVISGQMTSGNLIAFIIYEFVLGDCMESVGSVYSGLMQGVGAAEKVF
EFIDRQPTMVHDGSLAPDHLEGRVDFENVTFTYRTRPHTQVLQNVSFSLSPGKVTALVGPSGSGKSSCVNILENFYPLEGGRVLLDGKPISAYDHK
YLHRVISLVSQEPVLFARSITDNISYGLPTVPFEMVVEAAQKANAHGFIMELQDGYSTETGEKGAQLSGGQKQRVAMARALVRNPPVLILDEATSA
LDAESEYLIQQAIHGNLQKHTVLIIAHRLSTVEHAHLIVVLDKGRVVQQGTHQQLLAQGGLYAKLVQRQMLGLQPAADFTAGHNEPVANGSHKA

GPSGSGKSS       Walker A

LSGGQKQRVAMA    ABC transporter signature

RALVRNPPVLILDEAT    Walker B

FIG. 2

Clustal W(1.4) multiple sequence alignment.

8 Sequences Aligned.      Alignment Score = 59218
Gaps Inserted = 53        Conserved Identities = 149

Pairwise Alignment Mode: Slow
Pairwise Alignment Parameters:                      Multiple Alignment Parameters:
Open Gap Penalty = 10.0    Extend Gap Penalty = 0.1      Open Gap Penalty = 10.0    Extend Gap Penalty = 0.1
  Similarity Matrix: blosum                               Delay Divergent = 40%    Gap Distance = 8
                                                         Similarity Matrix: blosum

```
ABCB9       1   MRLWKAVVTLAFMSVDICVTTAIYVFSHLDRSLLEDIRHFNIF--DSVLDLWAACLYRSCLLLGATIGVAKNSALG------------PRRLRAS     82
rat TAPL    1   MRLWKAVVTLAFVSMDVGVTTAIYAFSHLDRSLLEDIRHFNIF--DSVLDLWAACLYRSCLLLGATIGVAKNSALG------------PRRLRAS     82
ABCB2       1   MASSRCPAPRGCRCLPGASLAWLGTVLLLLADWVLLRTALPRIFSLLVPTALPLLRVWAVGLSRWAVLWLGACGVLRATVGSKSENAGAQGWLAALKPLA  100
Mouse TAP1  1                    MAAHVWLAAA-LLLLVDWLLLRPMLPGIFSLLVP-EVPLLRVWVVGLSRWAILGLGVRGVLGVTAG--------AHGWLAALQPLV    76
Rat TAP1    1                    MAAHAWPTAALLLLLLVDWLLLRPVLPGIFSLLVP-EVPLLRVWAVGLSRWAILGLGVRGVLGVTAG--------ARGWLAALQPLV    77
ABCB3       1               MRLPDLRPWTSLLLVDAALLWLLQGPLGTLLP--QGLPGLWLEGTLR-----LGGLWGLLKLRGLL------------GFVGTLL    66
Mouse TAP2  1               MALSYLRPWVSLLLADMALLGLLQGSLGNLLP--QGLPGLWIEGTLR----LGVLWGLLKVGELL------------GLVGTLL    66
Rat TAP2    1               MALSHRPWASLLLVDLALLGLLQSSLGTLLP--PGLPGLWLEGTLR----LGVLWGLLKVGGLL------------RLVGTFL    66
                                                      *                  *   :                 *  :

ABCB9      83   WLVITLVCLFVGIYAMVKLLLFSEVRRPIRDPWF--WALFVWTYISLGASFLLWWLLSTVRPGTQALEPGAATEAEGFPGSGRPPPEQASGATLQKLLSY  180
rat TAPL   83   WLVITLVCLFVGIYAMAKLLLFSEVRRPIRDPWF--WALFVWTYISLAASFLLWGLLATVRPDAEALEP--------GNEGFHGEGGAPAEQASGATLQKLLSY  176
ABCB2     101   AALGLALPGLALFRELISWGAPGSADSTRLLHWGSHPTAFVVSYAAALPAAALWHKLG-------SLWVP-----------------------GGQGGSGNPVRRLLGC  179
Mouse TAP1 77   AALSLALPGLALFRELAAWGTLREGDSAGLLYWNSRPDAFAISYVAALPAAALWHKLG-------SLWAP-----------------------SGNRDAGDMLCRMLGF  155
Rat TAP1   78   AALGLALPGLASFRKLSAWGALREGDNAGLLHWNSRLDAFVLSYVAALPAAALWHKLG-------GFWAP-----------------------SGHKGAGDMLCRMLGF  156
ABCB3      67   LPLCLATPLTVSLRALVAGASRAPPARVASAPWS--WLLVGYG--AAGLSWSLWAVLS--PPGAQEKEQ------------DQVNNKVLMWRLLKL  144
Mouse TAP2 67   PLLCLATPLFFSLRALVGGTASTSVVRVASASWG--WLLAGYG--AVALSWAVAVLS--PAGVQEKEP------------GQEN-RTLMKRLLKL  143
Rat TAP2   67   PLLCLTNPLFFSLRALVGSTMSTSVVRVASASWG--WLLADYG--AVALSLAVWAVLS--PAGAQEKEP------------GQENNRALMIRLLRL  144
                   *   *    *             *            * *                             :  :  :*
```

```
ABCB9       481  EFIDRQPTMVHDGSLAPDHLEGRVDFENVTFYRTRPHTQVLQNVSFSLSPGKVTALVGPSGSGKSSCVNILENFYPLEGGRVLLDGKPISAYDHKYLHR  580
rat TAPL    477  EFIDRQPTMVHDGRLAPDHLEGRVDFENVTFYRTRPHTQVLQNVSFSLSPGKVTALVGPSGSGKSSCVNILENFYPLQGGRVLLDGEPIGAYDHKYLHR  576
ABCB2       480  EYLDRTPRCPPSGLLTPLHLEGLVQFQDVSFAYPNRPDVLVLQGLTFTLRPGEVTALVGPNGSGKSTVAALLQNLYQPTGGQLLLDGKPLPQYEHRYLHR  579
Mouse TAP1  456  EYLDRTPCSPLSGSLAPSNMKGLVEFQDVSFAYPNQPKVQVLQGLTFTLHPGTVTALVGPNGSGKSTVAALLQNLYQPTGGQLLLDGQRLVQYDHHYLHT  555
Rat TAP1    457  EYLDRTPCSPLSGSLAPLNMKGLVKFQDVSFAYPNHPNVQVLQGLTFTLYPGKVTALVGPNGSGKSTVAALLQNLYQPTGGKVLLDGEPLVQYDHHYLHT  556
ABCB3       445  SYMDRQPNLPSPGTLAPTTLQGVVKFQDVSFAYPNRPDRPVLKGLTFTLRPGEVTALVGPNGSGKSTVAALLQNLYQPTGGQVLLDGQVLLDGEKPISQYEHCYLHS  544
Mouse TAP2  444  SYLDRKPNLPQPGILAPPWLEGRVEFQDVSFSYPRPEKPVLQGLTFTLHPGTVTALVGPNGSGKSTVAALLQNLYQPTGGQLLLDGEPLTEYDHHYLHR  543
Rat TAP2    445  SYLDRRPNLPNPGTLAPPRLEGRVEFQDVSFSYPSRPEKPVLQGLTFTLHPGKVTALVGPNGSGKSTVAALLQNLYQPTGGQLLLDGEPLVQYDHHYLHR  544
                      * *:*.   *   * .*  ** * ** ********* **** .   :*:*** .: **::*** *** .: :*** *.* ***

ABCB9       581  VISLVSQEPVLFARSITDNISYGLPTVPF-EMVVEAAQKANAHGFIMELQDGYSTETGEKGAQLSGGQKQRVAMARALVRNPPVLILDEATSALDAESEY  679
rat TAPL    577  VISLVSQEPVLFARSITDNISYGLPTVPF-EMVVEAAQKANAHGFIMELQDGYSTETGEKGAQLSGGQKQRVAMARALVRNPPVLILDEATSALDAESEY  675
ABCB2       580  QVAAVGQEPQVFGRSLQENIAYGLTQKPTMEEITAAAVKSGAHSFISGLPQGYDTEVGETGNQLSGGQRQAVALARALIRKPCVLILDDATSALDAGNQL  679
Mouse TAP1  556  QVAAVGQEPLLFGRSFRENIAYGLNRTPTMEEITAVAVESGAHDFISGFPQGYDTEVGETGNQLSGGQRQAVALARALIRKPLLLILDDATSALDAGNQL  655
Rat TAP1    557  QVAAVGQEPLLFGRSFRENIAYGLTRTPTMEEITAVAMESGAHDFISGFPQGYDTEVGETGNQLSGGQRQAVALARALIRKPRLLILDDATSALDAGNQL  656
ABCB3       545  QVVSVGQEPVLFSGSVRNNIAYGLQSCED-DKVMAAAQAAHADDFIQEMEHGIYTDVGEKGSQLAAGQKQRLAIARALVRDPRVLILDEATSALDVQCEQ  643
Mouse TAP2  544  QVVLVGQEPVLFSGSVKDNIAYGLRDCED-AQVMAAAQAACADDFIGEMTNGINTEIGEKGGQLAVGQKQRLAIARALVRNPRVLILDEATSALDAQCEQ  642
Rat TAP2    545  QVVLVGQEPVLFSGSVKDNIAYGLRDCED-AQVMAAAQAACADDFIGEMTNGINTEIGEKGSQLAVGQKQRLAIARALVRNPRVLILDEATSALDAECEQ  643
                  :* .**::*:* .*  . *****   .       *. . .   *    :    .    .   .:***..*:**:**:**:*:.**:*:*** ****..******

ABCB9       680  LIQQAIHGN--LQKHTVLIIAHRLSTVEHAHLIVVLDKGRVVQQGTHQQLLAQGGLYAKLVQRQMLGLQPAADFTAGHNEPVANGSHKA  766
rat TAPL    676  LIQQAIHGN--LQRHTVLIIAHRLSTVERAHLIVVLDKGRVVQQGTHQQLLAQGGLYAKLVQRQMLGLEHPDYTAGHKEPPSNTEHKA  762
ABCB2       680  QVEQLLYESPERYSRSVLLITQHLSLVEQADHILFLEGGAIREGGTHQQLMEKKGCYWAMVQAPADAPE                      748
Mouse TAP1  656  RVQRLLYESPKRASRTVLLITQQLSLAEQAHHILFLREGSVGEQGTHLQLMKRGGCYRAMVEALAAPAD                      724
Rat TAP1    657  RVQRLLYESPEWASRTVLLITQQLSLAERAHHILFLKEGSVCEQGTHLQLMERGGCYRSMWEALAAPSD                      725
ABCB3       644  ALQDWNS----RGDRTVLVIAHRLQTVQRAHQILVLQEG---KLQKLAQL                                          686
Mouse TAP2  643  ALQNWRS----QGDRTMLVIAHRLHTVQNADQVLVLKQG---RLVEHDQLRDGQDVYAHLVQQRLEA                        702
Rat TAP2    644  ALQTWRS----QEDRTMLVIAHRLHTVQNADQVLVLKQG---QLVEHDQLRDEQDVYAHLVQQRLEA                        703
                              :       **
```

FIG. 3-3

SEQUENCE LISTING

```
<160> NUMBER OF SEQ ID NOS:  20

<210> SEQ ID NO 1
<211> LENGTH: 3536
<212> TYPE: DNA
<213> ORGANISM: Homo sapiens
<220> FEATURE:
<221> NAME/KEY: CDS
<222> LOCATION: (299)..(2596)

<400> SEQUENCE: 1
cgcccgggca ggtcagcctg tctcaaggca cgccagtctc agctccgacc ttgcagcggc        60
gcagcgcggg tgggaggcgg ggaggagcag cgggaagagc ggagcgagga cccggtccgg       120
cgcagtcttc aatgagcagc gcggaaactg cacccccagac ccgagcctgc tgcgcgcccc     180
ctcccagagc tcacctggtg ccaggtaaca ggcctggcct cgccctgtgg atgatgatgg       240
```

-continued

```
ccttgccccc gtgagctaca acctggcctt cagcacccgc ccacctccaa ccagcagg         298 atg cgg ctg tgg aag gcg gtg gtg gtg act ttg gcc ttc atg agt gtg         346
Met Arg Leu Trp Lys Ala Val Val Val Thr Leu Ala Phe Met Ser Val
 1               5                  10                  15 gac atc tgc gtg acc acg gcc atc tat gtc ttc agc cac ctg gac cgc         394
Asp Ile Cys Val Thr Thr Ala Ile Tyr Val Phe Ser His Leu Asp Arg
             20                  25                  30 agc ctc ctg gag gac atc cgc cac ttc aac atc ttt gac tcg gtg ctg         442
Ser Leu Leu Glu Asp Ile Arg His Phe Asn Ile Phe Asp Ser Val Leu
         35                  40                  45 gat ctc tgg gca gcc tgc ctg tac cgc agc tgc ctg ctg gga gcc             490
Asp Leu Trp Ala Ala Cys Leu Tyr Arg Ser Cys Leu Leu Leu Gly Ala
     50                  55                  60 acc att ggt gtg gcc aag aac agt gcg ctg ggg ccc cgg cgg ctg cgg         538
Thr Ile Gly Val Ala Lys Asn Ser Ala Leu Gly Pro Arg Arg Leu Arg
 65                  70                  75                  80 gcc tcg tgg ctg gtc atc acc ctc gtg tgc ctc ttc gtg ggc atc tat         586
Ala Ser Trp Leu Val Ile Thr Leu Val Cys Leu Phe Val Gly Ile Tyr
                 85                  90                  95 gcc atg gtg aag ctg ctc ctc ttc tca gag gtg cgc agg ccc atc cgg         634
Ala Met Val Lys Leu Leu Leu Phe Ser Glu Val Arg Arg Pro Ile Arg
             100                 105                 110 gac ccc tgg ttt tgg gcc ctg ttc gtg tgg acg tac att tca ctc ggc         682
Asp Pro Trp Phe Trp Ala Leu Phe Val Trp Thr Tyr Ile Ser Leu Gly
         115                 120                 125 gca tcc ttc ctg ctc tgg tgg ctg ctg tcc acc gtg cgg cca ggc acc         730
Ala Ser Phe Leu Leu Trp Trp Leu Leu Ser Thr Val Arg Pro Gly Thr
     130                 135                 140 cag gcc ctg gag cca ggg gcg gcc acc gag gct gag ggc ttc cct ggg         778
Gln Ala Leu Glu Pro Gly Ala Ala Thr Glu Ala Glu Gly Phe Pro Gly
145                 150                 155                 160 agc ggc cgg cca ccg ccc gag cag gcg tct ggg gcc acg ctg cag aag         826
Ser Gly Arg Pro Pro Pro Glu Gln Ala Ser Gly Ala Thr Leu Gln Lys
                 165                 170                 175 ctg ctc tcc tac acc aag ccc gac gtg gcc ttc ctc gtg gcc gcc tcc         874
Leu Leu Ser Tyr Thr Lys Pro Asp Val Ala Phe Leu Val Ala Ala Ser
             180                 185                 190 ttc ttc ctc atc gtg gca gct ctg gga gag acc ttc ctg ccc tac tac         922
Phe Phe Leu Ile Val Ala Ala Leu Gly Glu Thr Phe Leu Pro Tyr Tyr
         195                 200                 205 acg ggc cgc gcc att gat ggc atc gtc atc cag aaa agc atg gat cag         970
Thr Gly Arg Ala Ile Asp Gly Ile Val Ile Gln Lys Ser Met Asp Gln
     210                 215                 220 ttc agc acg gct gtc gtc atc gtg tgc ctg ctg gcc att ggc agc tca        1018
Phe Ser Thr Ala Val Val Ile Val Cys Leu Leu Ala Ile Gly Ser Ser
225                 230                 235                 240 ttt gcc gca ggt att cgg ggc ggc att ttt acc ctc ata ttt gcc aga        1066
Phe Ala Ala Gly Ile Arg Gly Gly Ile Phe Thr Leu Ile Phe Ala Arg
                 245                 250                 255 ctg aac att cgc ctt cga aac tgt ctc ttc cgc tca ctg gtg tcc cag        1114
Leu Asn Ile Arg Leu Arg Asn Cys Leu Phe Arg Ser Leu Val Ser Gln
             260                 265                 270 gag aca agc ttc ttt gat gag aac cgc aca ggg gac ctc atc tcc cgc        1162
Glu Thr Ser Phe Phe Asp Glu Asn Arg Thr Gly Asp Leu Ile Ser Arg
         275                 280                 285 ctg acc tcg gac acc acc atg gtc agc gac ctg gtc tcc cag aac atc        1210
Leu Thr Ser Asp Thr Thr Met Val Ser Asp Leu Val Ser Gln Asn Ile
     290                 295                 300 aat gtc ttc ctg cgg aac aca gtc aag gtc acg ggc gtg gtg gtc ttc        1258
```

```
Asn Val Phe Leu Arg Asn Thr Val Lys Val Thr Gly Val Val Val Phe
305                 310                 315                 320 atg ttc agc ctc tca tgg cag ctc tcc ttg gtc acc ttc atg ggc ttc    1306
Met Phe Ser Leu Ser Trp Gln Leu Ser Leu Val Thr Phe Met Gly Phe
                325                 330                 335 ccc atc atc atg atg gtg tcc aac atc tac ggc aag tac tac aag agg    1354
Pro Ile Ile Met Met Val Ser Asn Ile Tyr Gly Lys Tyr Tyr Lys Arg
            340                 345                 350 ctc tcc aaa gag gtc cag aat gcc ctg gcc aga gcg agc aac acg gcg    1402
Leu Ser Lys Glu Val Gln Asn Ala Leu Ala Arg Ala Ser Asn Thr Ala
        355                 360                 365 gag gag acc atc agt gcc atg aag act gtc cgg agc ttc gcc aat gag    1450
Glu Glu Thr Ile Ser Ala Met Lys Thr Val Arg Ser Phe Ala Asn Glu
370                 375                 380 gag gag gag gca gag gtg tac ctg cgg aag ctg cag cag gtg tac aag    1498
Glu Glu Glu Ala Glu Val Tyr Leu Arg Lys Leu Gln Gln Val Tyr Lys
385                 390                 395                 400 ctg aac agg aag gag gca gct gcc tac atg tac tac gtc tgg ggc agc    1546
Leu Asn Arg Lys Glu Ala Ala Ala Tyr Met Tyr Tyr Val Trp Gly Ser
                405                 410                 415 ggg ctc aca ctg ctg gtg gtc cag gtc agc atc ctc tac tac ggg ggc    1594
Gly Leu Thr Leu Leu Val Val Gln Val Ser Ile Leu Tyr Tyr Gly Gly
            420                 425                 430 cac ctt gtc atc tca ggc cag atg acc agc ggc aac ctc atc gcc ttc    1642
His Leu Val Ile Ser Gly Gln Met Thr Ser Gly Asn Leu Ile Ala Phe
        435                 440                 445 atc atc tac gag ttt gtc ctg gga gat tgt atg gag tcc gtg ggc tcc    1690
Ile Ile Tyr Glu Phe Val Leu Gly Asp Cys Met Glu Ser Val Gly Ser
450                 455                 460 gtc tac agt ggc ctg atg cag gga gtg ggg gct gct gag aag gtg ttc    1738
Val Tyr Ser Gly Leu Met Gln Gly Val Gly Ala Ala Glu Lys Val Phe
465                 470                 475                 480 gag ttc atc gac cgg cag ccg acc atg gtg cac gat ggc agc ttg gcc    1786
Glu Phe Ile Asp Arg Gln Pro Thr Met Val His Asp Gly Ser Leu Ala
                485                 490                 495 ccc gac cac ctg gag ggc cgg gtg gac ttt gag aat gtg acc ttc acc    1834
Pro Asp His Leu Glu Gly Arg Val Asp Phe Glu Asn Val Thr Phe Thr
            500                 505                 510 tac cgc act cgg ccc cac acc cag gtc ctg cag aat gtc tcc ttc agc    1882
Tyr Arg Thr Arg Pro His Thr Gln Val Leu Gln Asn Val Ser Phe Ser
        515                 520                 525 ctg tcc ccc ggc aag gtg acg gcc ctg gtg ggg ccc tcg ggc agt ggg    1930
Leu Ser Pro Gly Lys Val Thr Ala Leu Val Gly Pro Ser Gly Ser Gly
530                 535                 540 aag agc tcc tgt gtc aac atc ctg gag aac ttc tac ccc ctg gag ggg    1978
Lys Ser Ser Cys Val Asn Ile Leu Glu Asn Phe Tyr Pro Leu Glu Gly
545                 550                 555                 560 ggc cgg gtg ctg ctg gac ggc aag ccc atc agc gcc tac gac cac aag    2026
Gly Arg Val Leu Leu Asp Gly Lys Pro Ile Ser Ala Tyr Asp His Lys
                565                 570                 575 tac ttg cac cgt gtg atc tcc ctg gtg agc cag gag ccc gtg ctg ttc    2074
Tyr Leu His Arg Val Ile Ser Leu Val Ser Gln Glu Pro Val Leu Phe
            580                 585                 590 gcc cgc tcc atc acg gat aac atc tcc tac ggc ctg ccc act gtg cct    2122
Ala Arg Ser Ile Thr Asp Asn Ile Ser Tyr Gly Leu Pro Thr Val Pro
        595                 600                 605 ttc gag atg gtg gtg gag gcc gca cag aag gcc aat gcc cac ggc ttc    2170
Phe Glu Met Val Val Glu Ala Ala Gln Lys Ala Asn Ala His Gly Phe
610                 615                 620
```

-continued

| | | |
|---|---|---|
| atc atg gaa ctc cag gac ggc tac agc aca gag aca ggg gag aag ggc<br>Ile Met Glu Leu Gln Asp Gly Tyr Ser Thr Glu Thr Gly Glu Lys Gly<br>625      630      635      640 | | 2218 |
| gcc cag ctg tca ggt ggc cag aag cag cgg gtg gcc atg gcc cgg gct<br>Ala Gln Leu Ser Gly Gly Gln Lys Gln Arg Val Ala Met Ala Arg Ala<br>      645      650      655 | | 2266 |
| ctg gtg cgg aac ccc cca gtc ctc atc ctg gat gaa gcc acc agc gct<br>Leu Val Arg Asn Pro Pro Val Leu Ile Leu Asp Glu Ala Thr Ser Ala<br>  660      665      670 | | 2314 |
| ttg gat gcc gag agc gag tat ctg atc cag cag gcc atc cat ggc aac<br>Leu Asp Ala Glu Ser Glu Tyr Leu Ile Gln Gln Ala Ile His Gly Asn<br>675      680      685 | | 2362 |
| ctg cag aag cac acg gta ctc atc atc gcg cac cgg ctg agc acc gtg<br>Leu Gln Lys His Thr Val Leu Ile Ile Ala His Arg Leu Ser Thr Val<br>690      695      700 | | 2410 |
| gag cac gcg cac ctc att gtg gtg ctg gac aag ggc cgc gta gtg cag<br>Glu His Ala His Leu Ile Val Val Leu Asp Lys Gly Arg Val Val Gln<br>705      710      715      720 | | 2458 |
| cag ggc acc cac cag cag ctg ctg gcc cag ggc ggc ctc tac gcc aag<br>Gln Gly Thr His Gln Gln Leu Leu Ala Gln Gly Gly Leu Tyr Ala Lys<br>      725      730      735 | | 2506 |
| ctg gtg cag cgg cag atg ctg ggg ctt cag ccc gcc gca gac ttc aca<br>Leu Val Gln Arg Gln Met Leu Gly Leu Gln Pro Ala Ala Asp Phe Thr<br>  740      745      750 | | 2554 |
| gct ggc cac aac gag cct gta gcc aac ggc agt cac aag gcc<br>Ala Gly His Asn Glu Pro Val Ala Asn Gly Ser His Lys Ala<br>755      760      765 | | 2596 |
| tgatgggggg cccctgcttc tcccggtggg gcagaggacc cggtgcctgc ctggcagatg | | 2656 |
| tgccacggga ggcccccagc tgccctccga gcccaggcct gcagcactga agacgacct | | 2716 |
| gccatgtccc atggatcacc gcttcctgca tcttgcccct ggtccctgcc ccattcccag | | 2776 |
| ggcactcctt acccctgctg ccctgagcca acgccttcac ggacctccct agcctcctaa | | 2836 |
| gcaaaggtag agctgccttt ttaaacctag gtcttaccag ggttttttact gtttggtttg | | 2896 |
| aggcacccca gtcaactcct agatttcaaa aaccttttc taattgggag taatggcggg | | 2956 |
| cactttcacc aagatgttct agaaacttct gagccaggag tgaatggccc ttccttagta | | 3016 |
| gcctggggga tgtccagaga ctaggcctct ccccttacc cctccagaga aggggcttcc | | 3076 |
| ctgtcccgga gggacacggg gaacgggatt ttccgtctct ccctcttgcc agctctgtga | | 3136 |
| gtctggccag ggcgggtagg gagcgtggag ggcatctgtc tgccatcgcc cgctgccaat | | 3196 |
| ctaagccagt ctcactgtga accacacgaa acctcaactg ggggagtgag gggctggcca | | 3256 |
| ggtctggagg ggcctcaggg gtgcccagcc cggcacccag cgctttcgcc cctcgtccac | | 3316 |
| ccaccctgg ctggcagcct ccctccccac acccgcccct gtgctctgct gtctggaggc | | 3376 |
| cacgtggatg ttcatgagat gcattctctt ctgtctttgg tggatgggat ggtggcaaag | | 3436 |
| cccaggatct ggctttgcca gaggttgcaa catgttgaga gaacccggtc aataaagtgt | | 3496 |
| actacctctt acccctaaaa aaaaaaaaaa aaaaaaaaa | | 3536 |

<210> SEQ ID NO 2
<211> LENGTH: 766
<212> TYPE: PRT
<213> ORGANISM: Homo sapiens

<400> SEQUENCE: 2

Met Arg Leu Trp Lys Ala Val Val Thr Leu Ala Phe Met Ser Val
1     5       10       15

```
Asp Ile Cys Val Thr Ala Ile Tyr Val Phe Ser His Leu Asp Arg
         20                  25                  30

Ser Leu Leu Glu Asp Ile Arg His Phe Asn Ile Phe Asp Ser Val Leu
             35                  40                  45

Asp Leu Trp Ala Ala Cys Leu Tyr Arg Ser Cys Leu Leu Leu Gly Ala
         50                  55                  60

Thr Ile Gly Val Ala Lys Asn Ser Ala Leu Gly Pro Arg Arg Leu Arg
 65                  70                  75                  80

Ala Ser Trp Leu Val Ile Thr Leu Val Cys Leu Phe Val Gly Ile Tyr
                 85                  90                  95

Ala Met Val Lys Leu Leu Leu Phe Ser Glu Val Arg Arg Pro Ile Arg
             100                 105                 110

Asp Pro Trp Phe Trp Ala Leu Phe Val Trp Thr Tyr Ile Ser Leu Gly
         115                 120                 125

Ala Ser Phe Leu Leu Trp Trp Leu Leu Ser Thr Val Arg Pro Gly Thr
         130                 135                 140

Gln Ala Leu Glu Pro Gly Ala Ala Thr Glu Ala Gly Phe Pro Gly
145                 150                 155                 160

Ser Gly Arg Pro Pro Glu Gln Ala Ser Gly Ala Thr Leu Gln Lys
                 165                 170                 175

Leu Leu Ser Tyr Thr Lys Pro Asp Val Ala Phe Leu Val Ala Ala Ser
             180                 185                 190

Phe Phe Leu Ile Val Ala Ala Leu Gly Glu Thr Phe Leu Pro Tyr Tyr
         195                 200                 205

Thr Gly Arg Ala Ile Asp Gly Ile Val Ile Gln Lys Ser Met Asp Gln
         210                 215                 220

Phe Ser Thr Ala Val Val Ile Val Cys Leu Leu Ala Ile Gly Ser Ser
225                 230                 235                 240

Phe Ala Ala Gly Ile Arg Gly Gly Ile Phe Thr Leu Ile Phe Ala Arg
                 245                 250                 255

Leu Asn Ile Arg Leu Arg Asn Cys Leu Phe Arg Ser Leu Val Ser Gln
             260                 265                 270

Glu Thr Ser Phe Phe Asp Glu Asn Arg Thr Gly Asp Leu Ile Ser Arg
             275                 280                 285

Leu Thr Ser Asp Thr Thr Met Val Ser Asp Leu Val Ser Gln Asn Ile
         290                 295                 300

Asn Val Phe Leu Arg Asn Thr Val Lys Val Thr Gly Val Val Phe
305                 310                 315                 320

Met Phe Ser Leu Ser Trp Gln Leu Ser Leu Val Thr Phe Met Gly Phe
             325                 330                 335

Pro Ile Ile Met Met Val Ser Asn Ile Tyr Gly Lys Tyr Tyr Lys Arg
             340                 345                 350

Leu Ser Lys Glu Val Gln Asn Ala Leu Ala Arg Ala Ser Asn Thr Ala
         355                 360                 365

Glu Glu Thr Ile Ser Ala Met Lys Thr Val Arg Ser Phe Ala Asn Glu
         370                 375                 380

Glu Glu Ala Glu Val Tyr Leu Arg Lys Leu Gln Gln Val Tyr Lys
385                 390                 395                 400

Leu Asn Arg Lys Glu Ala Ala Tyr Met Tyr Tyr Val Trp Gly Ser
                 405                 410                 415

Gly Leu Thr Leu Leu Val Val Gln Val Ser Ile Leu Tyr Tyr Gly Gly
             420                 425                 430

His Leu Val Ile Ser Gly Gln Met Thr Ser Gly Asn Leu Ile Ala Phe
```

```
                435             440             445
Ile Ile Tyr Glu Phe Val Leu Gly Asp Cys Met Glu Ser Val Gly Ser
            450             455             460

Val Tyr Ser Gly Leu Met Gln Gly Val Gly Ala Ala Glu Lys Val Phe
465             470             475             480

Glu Phe Ile Asp Arg Gln Pro Thr Met Val His Asp Gly Ser Leu Ala
                485             490             495

Pro Asp His Leu Glu Gly Arg Val Asp Phe Glu Asn Val Thr Phe Thr
            500             505             510

Tyr Arg Thr Arg Pro His Thr Gln Val Leu Gln Asn Val Ser Phe Ser
            515             520             525

Leu Ser Pro Gly Lys Val Thr Ala Leu Val Gly Pro Ser Gly Ser Gly
530             535             540

Lys Ser Ser Cys Val Asn Ile Leu Glu Asn Phe Tyr Pro Leu Glu Gly
545             550             555             560

Gly Arg Val Leu Leu Asp Gly Lys Pro Ile Ser Ala Tyr Asp His Lys
                565             570             575

Tyr Leu His Arg Val Ile Ser Leu Val Ser Gln Glu Pro Val Leu Phe
            580             585             590

Ala Arg Ser Ile Thr Asp Asn Ile Ser Tyr Gly Leu Pro Thr Val Pro
            595             600             605

Phe Glu Met Val Val Glu Ala Ala Gln Lys Ala Asn Ala His Gly Phe
610             615             620

Ile Met Glu Leu Gln Asp Gly Tyr Ser Thr Glu Thr Gly Glu Lys Gly
625             630             635             640

Ala Gln Leu Ser Gly Gly Gln Lys Gln Arg Val Ala Met Ala Arg Ala
                645             650             655

Leu Val Arg Asn Pro Pro Val Leu Ile Leu Asp Glu Ala Thr Ser Ala
            660             665             670

Leu Asp Ala Glu Ser Glu Tyr Leu Ile Gln Gln Ala Ile His Gly Asn
            675             680             685

Leu Gln Lys His Thr Val Leu Ile Ile Ala His Arg Leu Ser Thr Val
690             695             700

Glu His Ala His Leu Ile Val Val Leu Asp Lys Gly Arg Val Val Gln
705             710             715             720

Gln Gly Thr His Gln Gln Leu Leu Ala Gln Gly Leu Tyr Ala Lys
                725             730             735

Leu Val Gln Arg Gln Met Leu Gly Leu Gln Pro Ala Ala Asp Phe Thr
            740             745             750

Ala Gly His Asn Glu Pro Val Ala Asn Gly Ser His Lys Ala
            755             760             765

<210> SEQ ID NO 3
<211> LENGTH: 2298
<212> TYPE: DNA
<213> ORGANISM: Homo sapiens
<220> FEATURE:
<221> NAME/KEY: CDS
<222> LOCATION: (1)..(2298)

<400> SEQUENCE: 3 atg cgg ctg tgg aag gcg gtg gtg gtg act ttg gcc ttc atg agt gtg       48
Met Arg Leu Trp Lys Ala Val Val Val Thr Leu Ala Phe Met Ser Val
1               5                   10                  15 gac atc tgc gtg acc acg gcc atc tat gtc ttc agc cac ctg gac cgc       96
Asp Ile Cys Val Thr Thr Ala Ile Tyr Val Phe Ser His Leu Asp Arg
```

|                   |     |     |     |     |     |     |     |     |     |     |     |     |     |     |     |      |
|---|---|---|---|---|---|---|---|---|---|---|---|---|---|---|---|---|
|                   |     |     | 20  |     |     |     |     | 25  |     |     |     |     | 30  |     |     |      |
| agc | ctc | ctg | gag | gac | atc | cgc | cac | ttc | aac | atc | ttt | gac | tcg | gtg | ctg | 144 |
| Ser | Leu | Leu | Glu | Asp | Ile | Arg | His | Phe | Asn | Ile | Phe | Asp | Ser | Val | Leu |     |
|     |     | 35  |     |     |     |     | 40  |     |     |     |     | 45  |     |     |     |     |
| gat | ctc | tgg | gca | gcc | tgc | ctg | tac | cgc | agc | tgc | ctg | ctg | ctg | gga | gcc | 192 |
| Asp | Leu | Trp | Ala | Ala | Cys | Leu | Tyr | Arg | Ser | Cys | Leu | Leu | Leu | Gly | Ala |     |
|     | 50  |     |     |     |     | 55  |     |     |     |     | 60  |     |     |     |     |     |
| acc | att | ggt | gtg | gcc | aag | aac | agt | gcg | ctg | ggg | ccc | cgg | cgg | ctg | cgg | 240 |
| Thr | Ile | Gly | Val | Ala | Lys | Asn | Ser | Ala | Leu | Gly | Pro | Arg | Arg | Leu | Arg |     |
| 65  |     |     |     |     | 70  |     |     |     |     | 75  |     |     |     |     | 80  |     |
| gcc | tcg | tgg | ctg | gtc | atc | acc | ctc | gtg | tgc | ctc | ttc | gtg | ggc | atc | tat | 288 |
| Ala | Ser | Trp | Leu | Val | Ile | Thr | Leu | Val | Cys | Leu | Phe | Val | Gly | Ile | Tyr |     |
|     |     |     |     | 85  |     |     |     |     | 90  |     |     |     |     | 95  |     |     |
| gcc | atg | gtg | aag | ctg | ctc | ctc | ttc | tca | gag | gtg | cgc | agg | ccc | atc | cgg | 336 |
| Ala | Met | Val | Lys | Leu | Leu | Leu | Phe | Ser | Glu | Val | Arg | Arg | Pro | Ile | Arg |     |
|     |     |     | 100 |     |     |     |     | 105 |     |     |     |     | 110 |     |     |     |
| gac | ccc | tgg | ttt | tgg | gcc | ctg | ttc | gtg | tgg | acg | tac | att | tca | ctc | ggc | 384 |
| Asp | Pro | Trp | Phe | Trp | Ala | Leu | Phe | Val | Trp | Thr | Tyr | Ile | Ser | Leu | Gly |     |
|     |     |     | 115 |     |     |     |     | 120 |     |     |     |     | 125 |     |     |     |
| gca | tcc | ttc | ctg | ctc | tgg | tgg | ctg | ctg | tcc | acc | gtg | cgg | cca | ggc | acc | 432 |
| Ala | Ser | Phe | Leu | Leu | Trp | Trp | Leu | Leu | Ser | Thr | Val | Arg | Pro | Gly | Thr |     |
|     |     |     | 130 |     |     |     |     | 135 |     |     |     |     | 140 |     |     |     |
| cag | gcc | ctg | gag | cca | ggg | gcg | gcc | acc | gag | gct | gag | ggc | ttc | cct | ggg | 480 |
| Gln | Ala | Leu | Glu | Pro | Gly | Ala | Ala | Thr | Glu | Ala | Glu | Gly | Phe | Pro | Gly |     |
| 145 |     |     |     |     | 150 |     |     |     |     | 155 |     |     |     |     | 160 |     |
| agc | ggc | cgg | cca | ccg | ccc | gag | cag | gcg | tct | ggg | gcc | acg | ctg | cag | aag | 528 |
| Ser | Gly | Arg | Pro | Pro | Pro | Glu | Gln | Ala | Ser | Gly | Ala | Thr | Leu | Gln | Lys |     |
|     |     |     |     | 165 |     |     |     |     | 170 |     |     |     |     | 175 |     |     |
| ctg | ctc | tcc | tac | acc | aag | ccc | gac | gtg | gcc | ttc | ctc | gtg | gcc | gcc | tcc | 576 |
| Leu | Leu | Ser | Tyr | Thr | Lys | Pro | Asp | Val | Ala | Phe | Leu | Val | Ala | Ala | Ser |     |
|     |     |     | 180 |     |     |     |     | 185 |     |     |     |     | 190 |     |     |     |
| ttc | ttc | ctc | atc | gtg | gca | gct | ctg | gga | gag | acc | ttc | ctg | ccc | tac | tac | 624 |
| Phe | Phe | Leu | Ile | Val | Ala | Ala | Leu | Gly | Glu | Thr | Phe | Leu | Pro | Tyr | Tyr |     |
|     |     |     | 195 |     |     |     |     | 200 |     |     |     |     | 205 |     |     |     |
| acg | ggc | cgc | gcc | att | gat | ggc | atc | gtc | atc | cag | aaa | agc | atg | gat | cag | 672 |
| Thr | Gly | Arg | Ala | Ile | Asp | Gly | Ile | Val | Ile | Gln | Lys | Ser | Met | Asp | Gln |     |
|     |     | 210 |     |     |     |     | 215 |     |     |     |     | 220 |     |     |     |     |
| ttc | agc | acg | gct | gtc | gtc | atc | gtg | tgc | ctg | ctg | gcc | att | ggc | agc | tca | 720 |
| Phe | Ser | Thr | Ala | Val | Val | Ile | Val | Cys | Leu | Leu | Ala | Ile | Gly | Ser | Ser |     |
| 225 |     |     |     | 230 |     |     |     |     | 235 |     |     |     |     | 240 |     |     |
| ttt | gcc | gca | ggt | att | cgg | ggc | ggc | att | ttt | acc | ctc | ata | ttt | gcc | aga | 768 |
| Phe | Ala | Ala | Gly | Ile | Arg | Gly | Gly | Ile | Phe | Thr | Leu | Ile | Phe | Ala | Arg |     |
|     |     |     |     | 245 |     |     |     |     | 250 |     |     |     |     | 255 |     |     |
| ctg | aac | att | cgc | ctt | cga | aac | tgt | ctc | ttc | cgc | tca | ctg | gtg | tcc | cag | 816 |
| Leu | Asn | Ile | Arg | Leu | Arg | Asn | Cys | Leu | Phe | Arg | Ser | Leu | Val | Ser | Gln |     |
|     |     |     | 260 |     |     |     |     | 265 |     |     |     |     | 270 |     |     |     |
| gag | aca | agc | ttc | ttt | gat | gag | aac | cgc | aca | ggg | gac | ctc | atc | tcc | cgc | 864 |
| Glu | Thr | Ser | Phe | Phe | Asp | Glu | Asn | Arg | Thr | Gly | Asp | Leu | Ile | Ser | Arg |     |
|     |     | 275 |     |     |     |     | 280 |     |     |     |     | 285 |     |     |     |     |
| ctg | acc | tcg | gac | acc | acc | atg | gtc | agc | gac | ctg | gtc | tcc | cag | aac | atc | 912 |
| Leu | Thr | Ser | Asp | Thr | Thr | Met | Val | Ser | Asp | Leu | Val | Ser | Gln | Asn | Ile |     |
|     | 290 |     |     |     |     | 295 |     |     |     |     | 300 |     |     |     |     |     |
| aat | gtc | ttc | ctg | cgg | aac | aca | gtc | aag | gtc | acg | ggc | gtg | gtg | gtc | ttc | 960 |
| Asn | Val | Phe | Leu | Arg | Asn | Thr | Val | Lys | Val | Thr | Gly | Val | Val | Val | Phe |     |
| 305 |     |     |     | 310 |     |     |     |     | 315 |     |     |     |     | 320 |     |     |
| atg | ttc | agc | ctc | tca | tgg | cag | ctc | tcc | ttg | gtc | acc | ttc | atg | ggc | ttc | 1008 |
| Met | Phe | Ser | Leu | Ser | Trp | Gln | Leu | Ser | Leu | Val | Thr | Phe | Met | Gly | Phe |     |
|     |     |     |     | 325 |     |     |     |     | 330 |     |     |     |     | 335 |     |     |
| ccc | atc | atc | atg | atg | gtg | tcc | aac | atc | tac | ggc | aag | tac | tac | aag | agg | 1056 |

```
Pro Ile Ile Met Met Val Ser Asn Ile Tyr Gly Lys Tyr Tyr Lys Arg
            340                 345                 350 ctc tcc aaa gag gtc cag aat gcc ctg gcc aga gcg agc aac acg gcg     1104
Leu Ser Lys Glu Val Gln Asn Ala Leu Ala Arg Ala Ser Asn Thr Ala
            355                 360                 365 gag gag acc atc agt gcc atg aag act gtc cgg agc ttc gcc aat gag     1152
Glu Glu Thr Ile Ser Ala Met Lys Thr Val Arg Ser Phe Ala Asn Glu
            370                 375                 380 gag gag gag gca gag gtg tac ctg cgg aag ctg cag cag gtg tac aag     1200
Glu Glu Glu Ala Glu Val Tyr Leu Arg Lys Leu Gln Gln Val Tyr Lys
385                 390                 395                 400 ctg aac agg aag gag gca gct gcc tac atg tac tac gtc tgg ggc agc     1248
Leu Asn Arg Lys Glu Ala Ala Ala Tyr Met Tyr Tyr Val Trp Gly Ser
            405                 410                 415 ggg ctc aca ctg ctg gtg gtc cag gtc agc atc ctc tac tac ggg ggc     1296
Gly Leu Thr Leu Leu Val Val Gln Val Ser Ile Leu Tyr Tyr Gly Gly
            420                 425                 430 cac ctt gtc atc tca ggc cag atg acc agc ggc aac ctc atc gcc ttc     1344
His Leu Val Ile Ser Gly Gln Met Thr Ser Gly Asn Leu Ile Ala Phe
            435                 440                 445 atc atc tac gag ttt gtc ctg gga gat tgt atg gag tcc gtg ggc tcc     1392
Ile Ile Tyr Glu Phe Val Leu Gly Asp Cys Met Glu Ser Val Gly Ser
            450                 455                 460 gtc tac agt ggc ctg atg cag gga gtg ggg gct gct gag aag gtg ttc     1440
Val Tyr Ser Gly Leu Met Gln Gly Val Gly Ala Ala Glu Lys Val Phe
465                 470                 475                 480 gag ttc atc gac cgg cag ccg acc atg gtg cac gat ggc agc ttg gcc     1488
Glu Phe Ile Asp Arg Gln Pro Thr Met Val His Asp Gly Ser Leu Ala
            485                 490                 495 ccc gac cac ctg gag ggc cgg gtg gac ttt gag aat gtg acc ttc acc     1536
Pro Asp His Leu Glu Gly Arg Val Asp Phe Glu Asn Val Thr Phe Thr
            500                 505                 510 tac cgc act cgg ccc cac acc cag gtc ctg cag aat gtc tcc ttc agc     1584
Tyr Arg Thr Arg Pro His Thr Gln Val Leu Gln Asn Val Ser Phe Ser
            515                 520                 525 ctg tcc ccc ggc aag gtg acg gcc ctg gtg ggg ccc tcg ggc agt ggg     1632
Leu Ser Pro Gly Lys Val Thr Ala Leu Val Gly Pro Ser Gly Ser Gly
            530                 535                 540 aag agc tcc tgt gtc aac atc ctg gag aac ttc tac ccc ctg gag ggg     1680
Lys Ser Ser Cys Val Asn Ile Leu Glu Asn Phe Tyr Pro Leu Glu Gly
545                 550                 555                 560 ggc cgg gtg ctg ctg gac ggc aag ccc atc agc gcc tac gac cac aag     1728
Gly Arg Val Leu Leu Asp Gly Lys Pro Ile Ser Ala Tyr Asp His Lys
            565                 570                 575 tac ttg cac cgt gtg atc tcc ctg gtg agc cag gag ccc gtg ctg ttc     1776
Tyr Leu His Arg Val Ile Ser Leu Val Ser Gln Glu Pro Val Leu Phe
            580                 585                 590 gcc cgc tcc atc acg gat aac atc tcc tac ggc ctg ccc act gtg cct     1824
Ala Arg Ser Ile Thr Asp Asn Ile Ser Tyr Gly Leu Pro Thr Val Pro
            595                 600                 605 ttc gag atg gtg gtg gag gcc gca cag aag gcc aat gcc cac ggc ttc     1872
Phe Glu Met Val Val Glu Ala Ala Gln Lys Ala Asn Ala His Gly Phe
            610                 615                 620 atc atg gaa ctc cag gac ggc tac agc aca gag aca ggg gag aag ggc     1920
Ile Met Glu Leu Gln Asp Gly Tyr Ser Thr Glu Thr Gly Glu Lys Gly
625                 630                 635                 640 gcc cag ctg tca ggt ggc cag aag cag cgg gtg gcc atg gcc cgg gct     1968
Ala Gln Leu Ser Gly Gly Gln Lys Gln Arg Val Ala Met Ala Arg Ala
            645                 650                 655
```

```
ctg gtg cgg aac ccc cca gtc ctc atc ctg gat gaa gcc acc agc gct       2016
Leu Val Arg Asn Pro Pro Val Leu Ile Leu Asp Glu Ala Thr Ser Ala
        660                 665                 670 ttg gat gcc gag agc gag tat ctg atc cag cag gcc atc cat ggc aac       2064
Leu Asp Ala Glu Ser Glu Tyr Leu Ile Gln Gln Ala Ile His Gly Asn
    675                 680                 685 ctg cag aag cac acg gta ctc atc atc gcg cac cgg ctg agc acc gtg       2112
Leu Gln Lys His Thr Val Leu Ile Ile Ala His Arg Leu Ser Thr Val
690                 695                 700 gag cac gcg cac ctc att gtg gtg ctg gac aag ggc cgc gta gtg cag       2160
Glu His Ala His Leu Ile Val Val Leu Asp Lys Gly Arg Val Val Gln
705                 710                 715                 720 cag ggc acc cac cag cag ctg ctg gcc cag ggc ggc ctc tac gcc aag       2208
Gln Gly Thr His Gln Gln Leu Leu Ala Gln Gly Gly Leu Tyr Ala Lys
                725                 730                 735 ctg gtg cag cgg cag atg ctg ggg ctt cag ccc gcc gca gac ttc aca       2256
Leu Val Gln Arg Gln Met Leu Gly Leu Gln Pro Ala Ala Asp Phe Thr
            740                 745                 750 gct ggc cac aac gag cct gta gcc aac ggc agt cac aag gcc               2298
Ala Gly His Asn Glu Pro Val Ala Asn Gly Ser His Lys Ala
        755                 760                 765

<210> SEQ ID NO 4
<211> LENGTH: 9
<212> TYPE: PRT
<213> ORGANISM: Homo sapiens

<400> SEQUENCE: 4

Gly Pro Ser Gly Ser Gly Lys Ser Ser
 1               5

<210> SEQ ID NO 5
<211> LENGTH: 12
<212> TYPE: PRT
<213> ORGANISM: Homo sapiens

<400> SEQUENCE: 5

Leu Ser Gly Gly Gln Lys Gln Arg Val Ala Met Ala
 1               5                  10

<210> SEQ ID NO 6
<211> LENGTH: 16
<212> TYPE: PRT
<213> ORGANISM: Homo sapiens

<400> SEQUENCE: 6

Arg Ala Leu Val Arg Asn Pro Pro Val Leu Ile Leu Asp Glu Ala Thr
 1               5                  10                  15

<210> SEQ ID NO 7
<211> LENGTH: 762
<212> TYPE: PRT
<213> ORGANISM: Rattus sp.

<400> SEQUENCE: 7

Met Arg Leu Trp Lys Ala Val Val Thr Leu Ala Phe Val Ser Met
 1               5                  10                  15

Asp Val Gly Val Thr Thr Ala Ile Tyr Ala Phe Ser His Leu Asp Arg
                20                  25                  30

Ser Leu Leu Glu Asp Ile Arg His Phe Asn Ile Phe Asp Ser Val Leu
        35                  40                  45

Asp Leu Trp Ala Ala Cys Leu Tyr Arg Ser Cys Leu Leu Leu Gly Ala
```

-continued

```
              50                  55                  60
Thr Ile Gly Val Ala Lys Asn Ser Ala Leu Gly Pro Arg Arg Leu Arg
 65                  70                  75                  80

Ala Ser Trp Leu Val Ile Thr Leu Val Cys Leu Phe Val Gly Ile Tyr
                     85                  90                  95

Ala Met Ala Lys Leu Leu Leu Phe Ser Glu Val Arg Arg Pro Ile Arg
                    100                 105                 110

Asp Pro Trp Phe Trp Ala Leu Phe Val Trp Thr Tyr Ile Ser Leu Ala
                    115                 120                 125

Ala Ser Phe Leu Leu Trp Gly Leu Leu Ala Thr Val Arg Pro Asp Ala
130                 135                 140

Glu Ala Leu Glu Pro Gly Asn Glu Gly Phe His Gly Glu Gly Gly Ala
145                 150                 155                 160

Pro Ala Glu Gln Ala Ser Gly Ala Thr Leu Gln Lys Leu Leu Ser Tyr
                    165                 170                 175

Thr Lys Pro Asp Val Ala Phe Leu Val Ala Ala Ser Phe Phe Leu Ile
                    180                 185                 190

Val Ala Ala Leu Gly Glu Thr Phe Leu Pro Tyr Tyr Thr Gly Arg Ala
                    195                 200                 205

Ile Asp Ser Ile Val Ile Gln Lys Ser Met Asp Gln Phe Thr Thr Ala
210                 215                 220

Val Val Val Val Cys Leu Leu Ala Ile Gly Ser Ser Leu Ala Ala Gly
225                 230                 235                 240

Ile Arg Gly Gly Ile Phe Thr Leu Val Phe Ala Arg Leu Asn Ile Arg
                    245                 250                 255

Leu Arg Asn Cys Leu Phe Arg Ser Leu Val Ser Gln Glu Thr Ser Phe
                    260                 265                 270

Phe Asp Glu Asn Arg Thr Gly Asp Leu Ile Ser Arg Leu Thr Ser Asp
                    275                 280                 285

Thr Thr Met Val Ser Asp Leu Val Ser Gln Asn Ile Asn Ile Phe Leu
290                 295                 300

Arg Asn Thr Val Lys Val Thr Gly Val Val Phe Met Phe Ser Leu
305                 310                 315                 320

Ser Trp Gln Leu Ser Leu Val Thr Phe Met Gly Phe Pro Ile Ile Met
                    325                 330                 335

Met Val Ser Asn Ile Tyr Gly Lys Tyr Tyr Lys Arg Leu Ser Lys Glu
                    340                 345                 350

Val Gln Ser Ala Leu Ala Arg Ala Ser Thr Thr Ala Glu Glu Thr Ile
                    355                 360                 365

Ser Ala Met Lys Thr Val Arg Ser Phe Ala Asn Glu Glu Glu Glu Ala
370                 375                 380

Glu Val Phe Leu Arg Lys Leu Gln Gln Val Tyr Lys Leu Asn Arg Lys
385                 390                 395                 400

Glu Ala Ala Ala Tyr Met Ser Tyr Val Trp Gly Ser Gly Leu Thr Leu
                    405                 410                 415

Leu Val Val Gln Val Ser Ile Leu Tyr Tyr Gly Gly His Leu Val Ile
                    420                 425                 430

Ser Gly Gln Met Ser Ser Gly Asn Leu Ile Ala Phe Ile Ile Tyr Glu
                    435                 440                 445

Phe Val Leu Gly Asp Cys Met Glu Ser Val Gly Ser Val Tyr Ser Gly
                    450                 455                 460

Leu Met Gln Gly Val Gly Ala Ala Glu Lys Val Phe Glu Phe Ile Asp
465                 470                 475                 480
```

-continued

```
Arg Gln Pro Thr Met Val His Asp Gly Arg Leu Ala Pro Asp His Leu
                485                 490                 495
Glu Gly Arg Val Asp Phe Glu Asn Val Thr Phe Thr Tyr Arg Thr Arg
            500                 505                 510
Pro His Thr Gln Val Leu Gln Asn Val Ser Phe Ser Leu Ser Pro Gly
        515                 520                 525
Lys Val Thr Ala Leu Val Gly Pro Ser Gly Ser Gly Lys Ser Ser Cys
    530                 535                 540
Val Asn Ile Leu Glu Asn Phe Tyr Pro Leu Gln Gly Arg Val Leu
545                 550                 555                 560
Leu Asp Gly Glu Pro Ile Gly Ala Tyr Asp His Lys Tyr Leu His Arg
                565                 570                 575
Val Ile Ser Leu Val Ser Gln Glu Pro Val Leu Phe Ala Arg Ser Ile
            580                 585                 590
Thr Asp Asn Ile Ser Tyr Gly Leu Pro Thr Val Pro Phe Glu Met Val
        595                 600                 605
Val Glu Ala Ala Gln Lys Ala Asn Ala His Gly Phe Ile Met Glu Leu
    610                 615                 620
Gln Asp Gly Tyr Ser Thr Glu Thr Gly Glu Lys Gly Ala Gln Leu Ser
625                 630                 635                 640
Gly Gly Gln Lys Gln Arg Val Ala Met Ala Arg Ala Leu Val Arg Asn
                645                 650                 655
Pro Pro Val Leu Ile Leu Asp Glu Ala Thr Ser Ala Leu Asp Ala Glu
            660                 665                 670
Ser Glu Tyr Leu Ile Gln Gln Ala Ile His Gly Asn Leu Gln Arg His
        675                 680                 685
Thr Val Leu Ile Ile Ala His Arg Leu Ser Thr Val Glu Arg Ala His
    690                 695                 700
Leu Ile Val Val Leu Asp Lys Gly Arg Val Val Gln Gln Gly Thr His
705                 710                 715                 720
Gln Gln Leu Leu Ala Gln Gly Gly Leu Tyr Ala Lys Leu Val Gln Arg
                725                 730                 735
Gln Met Leu Gly Leu Glu His Pro Leu Asp Tyr Thr Ala Gly His Lys
            740                 745                 750
Glu Pro Pro Ser Asn Thr Glu His Lys Ala
        755                 760

<210> SEQ ID NO 8
<211> LENGTH: 743
<212> TYPE: PRT
<213> ORGANISM: Homo sapiens

<400> SEQUENCE: 8

Met Ala Ser Ser Arg Cys Pro Ala Pro Arg Gly Cys Arg Cys Leu Pro
1               5                   10                  15
Gly Ala Ser Leu Ala Trp Leu Gly Thr Val Leu Leu Leu Leu Ala Asp
                20                  25                  30
Trp Val Leu Leu Arg Thr Ala Leu Pro Arg Ile Phe Ser Leu Leu Val
            35                  40                  45
Pro Thr Ala Leu Pro Leu Leu Arg Val Trp Ala Val Gly Leu Ser Arg
        50                  55                  60
Trp Ala Val Leu Trp Leu Gly Ala Cys Gly Val Leu Arg Ala Thr Val
65                  70                  75                  80
Gly Ser Lys Ser Glu Asn Ala Gly Ala Gln Gly Trp Leu Ala Ala Leu
```

-continued

```
                 85                  90                  95
Lys Pro Leu Ala Ala Leu Gly Leu Ala Leu Pro Gly Leu Ala Leu
            100                 105                 110
Phe Arg Glu Leu Ile Ser Trp Gly Ala Pro Gly Ser Ala Asp Ser Thr
            115                 120                 125
Arg Leu Leu His Trp Gly Ser His Pro Thr Ala Phe Val Val Ser Tyr
            130                 135                 140
Ala Ala Ala Leu Pro Ala Ala Leu Trp His Lys Leu Gly Gly Gly
145                 150                 155                 160
Gln Gly Gly Ser Gly Asn Pro Val Arg Leu Leu Gly Cys Leu Gly
                165                 170                 175
Ser Glu Thr Arg Arg Leu Ser Leu Phe Leu Val Leu Val Leu Ser
            180                 185                 190
Ser Leu Gly Glu Met Ala Ile Pro Phe Phe Thr Gly Arg Leu Thr Asp
            195                 200                 205
Trp Ile Leu Gln Asp Gly Ser Ala Asp Thr Phe Thr Arg Asn Leu Thr
            210                 215                 220
Leu Met Ser Ile Leu Thr Ile Ala Ser Ala Val Leu Glu Phe Val Gly
225                 230                 235                 240
Asp Gly Ile Tyr Asn Asn Thr Met Gly His Val His Ser His Leu Gln
                245                 250                 255
Gly Glu Val Phe Gly Ala Val Leu Arg Gln Glu Thr Glu Phe Phe Gln
                260                 265                 270
Gln Asn Gln Thr Gly Asn Ile Met Ser Arg Val Thr Glu Asp Thr Ser
            275                 280                 285
Thr Leu Ser Asp Ser Leu Ser Glu Asn Leu Ser Leu Phe Leu Trp Tyr
            290                 295                 300
Leu Val Arg Gly Leu Cys Leu Leu Gly Ile Met Leu Trp Gly Ser Val
305                 310                 315                 320
Ser Leu Thr Met Val Thr Leu Ile Thr Leu Pro Leu Leu Phe Leu Leu
                325                 330                 335
Pro Lys Lys Val Gly Lys Trp Tyr Gln Leu Leu Glu Val Gln Val Arg
            340                 345                 350
Glu Ser Leu Ala Lys Ser Ser Gln Val Ala Ile Glu Ala Leu Ser Ala
            355                 360                 365
Met Pro Thr Val Arg Ser Phe Ala Asn Glu Glu Gly Glu Ala Gln Lys
            370                 375                 380
Phe Arg Glu Lys Leu Gln Glu Ile Lys Thr Leu Asn Gln Lys Glu Ala
385                 390                 395                 400
Val Ala Tyr Ala Val Asn Ser Trp Thr Thr Ser Ile Ser Gly Met Leu
                405                 410                 415
Leu Lys Val Gly Ile Leu Tyr Ile Gly Gly Gln Leu Val Thr Ser Gly
            420                 425                 430
Ala Val Ser Ser Gly Asn Leu Val Thr Phe Val Leu Tyr Gln Met Gln
            435                 440                 445
Phe Thr Gln Ala Val Glu Val Leu Leu Ser Ile Tyr Pro Arg Val Gln
            450                 455                 460
Lys Ala Val Gly Ser Ser Glu Lys Ile Phe Glu Tyr Leu Asp Arg Thr
465                 470                 475                 480
Pro Arg Cys Pro Pro Ser Gly Leu Leu Thr Pro Leu His Leu Glu Gly
                485                 490                 495
Leu Val Gln Phe Gln Asp Val Ser Phe Ala Tyr Pro Asn Arg Pro Asp
            500                 505                 510
```

-continued

```
Val Leu Val Leu Gln Gly Leu Thr Phe Thr Leu Arg Pro Gly Glu Val
            515                 520                 525

Thr Ala Leu Val Gly Pro Asn Gly Ser Gly Lys Ser Thr Val Ala Ala
        530                 535                 540

Leu Leu Gln Asn Leu Tyr Gln Pro Thr Gly Gly Gln Leu Leu Leu Asp
545                 550                 555                 560

Gly Lys Pro Leu Pro Gln Tyr Glu His Arg Tyr Leu His Arg Gln Val
                565                 570                 575

Ala Ala Val Gly Gln Glu Pro Gln Val Phe Gly Arg Ser Leu Gln Glu
            580                 585                 590

Asn Ile Ala Tyr Gly Leu Thr Gln Lys Pro Thr Met Glu Glu Ile Thr
        595                 600                 605

Ala Ala Ala Val Lys Ser Gly Ala His Ser Phe Ile Ser Gly Leu Pro
610                 615                 620

Gln Gly Tyr Asp Thr Glu Val Asp Glu Ala Gly Ser Gln Leu Ser Gly
625                 630                 635                 640

Gly Gln Arg Gln Ala Val Ala Leu Ala Arg Ala Leu Ile Arg Lys Pro
                645                 650                 655

Cys Val Leu Ile Leu Asp Asp Ala Thr Ser Ala Leu Asp Ala Asn Ser
            660                 665                 670

Gln Leu Gln Val Glu Gln Leu Leu Tyr Glu Ser Pro Glu Arg Tyr Ser
        675                 680                 685

Arg Ser Val Leu Leu Ile Thr Gln His Leu Ser Leu Val Glu Gln Ala
690                 695                 700

Asp His Ile Leu Phe Leu Glu Gly Gly Ala Ile Arg Glu Gly Gly Thr
705                 710                 715                 720

His Gln Gln Leu Met Glu Lys Lys Gly Cys Tyr Trp Ala Met Val Gln
                725                 730                 735

Ala Pro Ala Asp Ala Pro Glu
            740

<210> SEQ ID NO 9
<211> LENGTH: 724
<212> TYPE: PRT
<213> ORGANISM: Mus musculus

<400> SEQUENCE: 9

Met Ala Ala His Val Trp Leu Ala Ala Leu Leu Leu Leu Val Asp
  1               5                  10                  15

Trp Leu Leu Arg Pro Met Leu Pro Gly Ile Phe Ser Leu Leu Val
                 20                  25                  30

Pro Glu Val Pro Leu Leu Arg Val Trp Val Gly Leu Ser Arg Trp
             35                  40                  45

Ala Ile Leu Gly Leu Gly Val Arg Gly Val Leu Gly Val Thr Ala Gly
         50                  55                  60

Ala His Gly Trp Leu Ala Ala Leu Gln Pro Leu Val Ala Ala Leu Ser
 65                  70                  75                  80

Leu Ala Leu Pro Gly Leu Ala Leu Phe Arg Glu Leu Ala Ala Trp Gly
                 85                  90                  95

Thr Leu Arg Glu Gly Asp Ser Ala Gly Leu Leu Tyr Trp Asn Ser Arg
            100                 105                 110

Pro Asp Ala Phe Ala Ile Ser Tyr Val Ala Ala Leu Pro Ala Ala Ala
        115                 120                 125

Leu Trp His Lys Leu Gly Ser Leu Trp Ala Pro Ser Gly Asn Arg Asp
```

-continued

```
                130                 135                 140
Ala Gly Asp Met Leu Cys Arg Met Leu Gly Phe Leu Gly Pro Lys Lys
145                 150                 155                 160

Arg Arg Leu Tyr Leu Val Leu Val Leu Ile Leu Ser Cys Leu Gly
                165                 170                 175

Glu Met Ala Ile Pro Phe Phe Thr Gly Arg Ile Thr Asp Trp Ile Leu
                180                 185                 190

Gln Asp Lys Thr Val Pro Ser Phe Thr Arg Asn Ile Trp Leu Met Ser
                195                 200                 205

Ile Leu Thr Ile Ala Ser Thr Ala Leu Glu Phe Ala Ser Asp Gly Ile
210                 215                 220

Tyr Asn Ile Thr Met Gly His Met His Gly Arg Val His Arg Glu Val
225                 230                 235                 240

Phe Arg Ala Val Leu Arg Gln Glu Thr Gly Phe Phe Leu Lys Asn Pro
                245                 250                 255

Ala Gly Ser Ile Thr Ser Arg Val Thr Glu Asp Thr Ala Asn Val Cys
                260                 265                 270

Glu Ser Ile Ser Asp Thr Leu Ser Leu Leu Trp Tyr Leu Gly Arg
                275                 280                 285

Ala Leu Cys Leu Leu Val Phe Met Phe Trp Gly Ser Pro Tyr Leu Thr
                290                 295                 300

Leu Val Thr Leu Ile Asn Leu Pro Leu Leu Phe Leu Leu Pro Lys Lys
305                 310                 315                 320

Leu Gly Lys Val His Gln Ser Leu Ala Val Lys Val Gln Glu Ser Leu
                325                 330                 335

Ala Lys Ser Thr Gln Val Ala Leu Glu Ala Leu Ser Ala Met Pro Thr
                340                 345                 350

Val Arg Ser Phe Ala Asn Glu Glu Gly Glu Ala Gln Lys Phe Arg Gln
                355                 360                 365

Lys Leu Glu Glu Met Lys Thr Leu Asn Lys Lys Glu Ala Leu Ala Tyr
                370                 375                 380

Val Ala Glu Val Trp Thr Thr Ser Val Ser Gly Met Leu Leu Lys Val
385                 390                 395                 400

Gly Ile Leu Tyr Leu Gly Gly Gln Leu Val Ile Arg Gly Thr Val Ser
                405                 410                 415

Ser Gly Asn Leu Val Ser Phe Val Leu Tyr Gln Leu Gln Phe Thr Gln
                420                 425                 430

Ala Val Gln Val Leu Leu Ser Leu Tyr Pro Ser Met Gln Lys Ala Val
                435                 440                 445

Gly Ser Ser Glu Lys Ile Phe Glu Tyr Leu Asp Arg Thr Pro Cys Ser
450                 455                 460

Pro Leu Ser Gly Ser Leu Ala Pro Ser Asn Met Lys Gly Leu Val Glu
465                 470                 475                 480

Phe Gln Asp Val Ser Phe Ala Tyr Pro Asn Gln Pro Lys Val Gln Val
                485                 490                 495

Leu Gln Gly Leu Thr Phe Thr Leu His Pro Gly Thr Val Thr Ala Leu
                500                 505                 510

Val Gly Pro Asn Gly Ser Gly Lys Ser Thr Val Ala Ala Leu Leu Gln
                515                 520                 525

Asn Leu Tyr Gln Pro Thr Gly Gly Gln Leu Leu Leu Asp Gly Gln Arg
                530                 535                 540

Leu Val Gln Tyr Asp His His Tyr Leu His Thr Gln Val Ala Ala Val
545                 550                 555                 560
```

-continued

Gly Gln Glu Pro Leu Leu Phe Gly Arg Ser Phe Arg Glu Asn Ile Ala
                565                 570                 575

Tyr Gly Leu Asn Arg Thr Pro Thr Met Glu Glu Ile Thr Ala Val Ala
                580                 585                 590

Val Glu Ser Gly Ala His Asp Phe Ile Ser Gly Phe Pro Gln Gly Tyr
                595                 600                 605

Asp Thr Glu Val Gly Glu Thr Gly Asn Gln Leu Ser Gly Gly Gln Arg
                610                 615                 620

Gln Ala Val Ala Leu Ala Arg Ala Leu Ile Arg Lys Pro Leu Leu Leu
625                 630                 635                 640

Ile Leu Asp Asp Ala Thr Ser Ala Leu Asp Ala Gly Asn Gln Leu Arg
                645                 650                 655

Val Gln Arg Leu Leu Tyr Glu Ser Pro Lys Arg Ala Ser Arg Thr Val
                660                 665                 670

Leu Leu Ile Thr Gln Gln Leu Ser Leu Ala Glu Gln Ala His His Ile
                675                 680                 685

Leu Phe Leu Arg Glu Gly Ser Val Gly Glu Gln Gly Thr His Leu Gln
                690                 695                 700

Leu Met Lys Arg Gly Gly Cys Tyr Arg Ala Met Val Glu Ala Leu Ala
705                 710                 715                 720

Ala Pro Ala Asp

<210> SEQ ID NO 10
<211> LENGTH: 725
<212> TYPE: PRT
<213> ORGANISM: Rattus sp.

<400> SEQUENCE: 10

Met Ala Ala His Ala Trp Pro Thr Ala Ala Leu Leu Leu Leu Leu Val
 1               5                  10                  15

Asp Trp Leu Leu Leu Arg Pro Val Leu Pro Gly Ile Phe Ser Leu Leu
                20                  25                  30

Val Pro Glu Val Pro Leu Leu Arg Val Trp Ala Val Gly Leu Ser Arg
                35                  40                  45

Trp Ala Ile Leu Gly Leu Gly Val Arg Gly Val Leu Gly Val Thr Ala
                50                  55                  60

Gly Ala Arg Gly Trp Leu Ala Ala Leu Gln Pro Leu Val Ala Ala Leu
65                  70                  75                  80

Gly Leu Ala Leu Pro Gly Leu Ala Ser Phe Arg Lys Leu Ser Ala Trp
                85                  90                  95

Gly Ala Leu Arg Glu Gly Asp Asn Ala Gly Leu Leu His Trp Asn Ser
                100                 105                 110

Arg Leu Asp Ala Phe Val Leu Ser Tyr Val Ala Ala Leu Pro Ala Ala
                115                 120                 125

Ala Leu Trp His Lys Leu Gly Gly Phe Trp Ala Pro Ser Gly His Lys
                130                 135                 140

Gly Ala Gly Asp Met Leu Cys Arg Met Leu Gly Phe Leu Asp Ser Lys
145                 150                 155                 160

Lys Gly Arg Leu His Leu Val Leu Val Leu Leu Ile Leu Ser Cys Leu
                165                 170                 175

Gly Glu Met Ala Ile Pro Phe Phe Thr Gly Arg Ile Thr Asp Trp Ile
                180                 185                 190

Leu Gln Asp Lys Thr Ala Pro Ser Phe Ala Arg Asn Met Trp Leu Met
                195                 200                 205

-continued

```
Cys Ile Leu Thr Ile Ala Ser Thr Val Leu Glu Phe Ala Gly Asp Gly
    210                 215                 220

Ile Tyr Asn Ile Thr Met Gly His Met His Ser Arg Val His Gly Glu
225                 230                 235                 240

Val Phe Arg Ala Val Leu His Gln Glu Thr Gly Phe Phe Leu Lys Asn
                245                 250                 255

Pro Thr Gly Ser Ile Thr Ser Arg Val Thr Glu Asp Thr Ser Asn Val
            260                 265                 270

Cys Glu Ser Ile Ser Asp Lys Leu Asn Leu Phe Leu Trp Tyr Leu Gly
        275                 280                 285

Arg Gly Leu Cys Leu Leu Ala Phe Met Ile Trp Gly Ser Phe Tyr Leu
    290                 295                 300

Thr Val Val Thr Leu Leu Ser Leu Pro Leu Leu Phe Leu Leu Pro Arg
305                 310                 315                 320

Arg Leu Gly Lys Val Tyr Gln Ser Leu Ala Val Lys Val Gln Glu Ser
                325                 330                 335

Leu Ala Lys Ser Thr Gln Val Ala Leu Glu Ala Leu Ser Ala Met Pro
            340                 345                 350

Thr Val Arg Ser Phe Ala Asn Glu Glu Gly Glu Ala Gln Lys Phe Arg
        355                 360                 365

Gln Lys Leu Glu Glu Met Lys Pro Leu Asn Lys Lys Glu Ala Leu Ala
    370                 375                 380

Tyr Val Thr Glu Val Trp Thr Met Ser Val Ser Gly Met Leu Leu Lys
385                 390                 395                 400

Val Gly Ile Leu Tyr Leu Gly Gly Gln Leu Val Val Arg Gly Ala Val
                405                 410                 415

Ser Ser Gly Asn Leu Val Ser Phe Val Leu Tyr Gln Leu Gln Phe Thr
            420                 425                 430

Arg Ala Val Glu Val Leu Leu Ser Ile Tyr Pro Ser Met Gln Lys Ser
        435                 440                 445

Val Gly Ala Ser Glu Lys Ile Phe Glu Tyr Leu Asp Arg Thr Pro Cys
    450                 455                 460

Ser Pro Leu Ser Gly Ser Leu Ala Pro Leu Asn Met Lys Gly Leu Val
465                 470                 475                 480

Lys Phe Gln Asp Val Ser Phe Ala Tyr Pro Asn His Pro Asn Val Gln
                485                 490                 495

Val Leu Gln Gly Leu Thr Phe Thr Leu Tyr Pro Gly Lys Val Thr Ala
            500                 505                 510

Leu Val Gly Pro Asn Gly Ser Gly Lys Ser Thr Val Ala Ala Leu Leu
        515                 520                 525

Gln Asn Leu Tyr Gln Pro Thr Gly Gly Lys Val Leu Leu Asp Gly Glu
    530                 535                 540

Pro Leu Val Gln Tyr Asp His His Tyr Leu His Thr Gln Val Ala Ala
545                 550                 555                 560

Val Gly Gln Glu Pro Leu Leu Phe Gly Arg Ser Phe Arg Glu Asn Ile
                565                 570                 575

Ala Tyr Gly Leu Thr Arg Thr Pro Thr Met Glu Glu Ile Thr Ala Val
            580                 585                 590

Ala Met Glu Ser Gly Ala His Asp Phe Ile Ser Gly Phe Pro Gln Gly
        595                 600                 605

Tyr Asp Thr Glu Val Gly Glu Thr Gly Asn Gln Leu Ser Gly Gly Gln
    610                 615                 620
```

```
Arg Gln Ala Val Ala Leu Ala Arg Ala Leu Ile Arg Lys Pro Arg Leu
625                 630                 635                 640

Leu Ile Leu Asp Asp Ala Thr Ser Ala Leu Asp Ala Gly Asn Gln Leu
                645                 650                 655

Arg Val Gln Arg Leu Leu Tyr Glu Ser Pro Glu Trp Ala Ser Arg Thr
            660                 665                 670

Val Leu Leu Ile Thr Gln Gln Leu Ser Leu Ala Glu Arg Ala His His
        675                 680                 685

Ile Leu Phe Leu Lys Glu Gly Ser Val Cys Glu Gln Gly Thr His Leu
    690                 695                 700

Gln Leu Met Glu Arg Gly Gly Cys Tyr Arg Ser Met Val Glu Ala Leu
705                 710                 715                 720

Ala Ala Pro Ser Asp
                725

<210> SEQ ID NO 11
<211> LENGTH: 686
<212> TYPE: PRT
<213> ORGANISM: Homo sapiens

<400> SEQUENCE: 11

Met Arg Leu Pro Asp Leu Arg Pro Trp Thr Ser Leu Leu Leu Val Asp
1               5                   10                  15

Ala Ala Leu Leu Trp Leu Leu Gln Gly Pro Leu Gly Thr Leu Leu Pro
                20                  25                  30

Gln Gly Leu Pro Gly Leu Trp Leu Glu Gly Thr Leu Arg Leu Gly Gly
            35                  40                  45

Leu Trp Gly Leu Leu Lys Leu Arg Gly Leu Leu Gly Phe Val Gly Thr
    50                  55                  60

Leu Leu Leu Pro Leu Cys Leu Ala Thr Pro Leu Thr Val Ser Leu Arg
65                  70                  75                  80

Ala Leu Val Ala Gly Ala Ser Arg Ala Pro Pro Ala Arg Val Ala Ser
                85                  90                  95

Ala Pro Trp Ser Trp Leu Leu Val Gly Tyr Gly Ala Ala Gly Leu Ser
            100                 105                 110

Trp Ser Leu Trp Ala Val Leu Ser Pro Pro Gly Ala Gln Glu Lys Glu
    115                 120                 125

Gln Asp Gln Val Asn Asn Lys Val Leu Met Trp Arg Leu Leu Lys Leu
130                 135                 140

Ser Arg Pro Asp Leu Pro Leu Leu Val Ala Ala Phe Phe Leu Val
145                 150                 155                 160

Leu Ala Val Leu Gly Glu Thr Leu Ile Pro His Tyr Ser Gly Arg Val
                165                 170                 175

Ile Asp Ile Leu Gly Gly Asp Phe Asp Pro His Ala Phe Ala Ser Ala
            180                 185                 190

Ile Phe Phe Met Cys Leu Phe Ser Phe Gly Ser Ser Leu Ser Ala Gly
    195                 200                 205

Cys Arg Gly Gly Cys Phe Thr Tyr Thr Met Ser Arg Ile Asn Leu Arg
210                 215                 220

Ile Arg Glu Gln Leu Phe Ser Ser Leu Leu Arg Gln Asp Leu Gly Phe
225                 230                 235                 240

Phe Gln Glu Thr Lys Thr Gly Glu Leu Asn Ser Arg Leu Ser Ser Asp
                245                 250                 255

Thr Thr Leu Met Ser Asn Trp Leu Pro Leu Asn Ala Asn Val Leu Leu
            260                 265                 270
```

```
Arg Ser Leu Val Lys Val Gly Leu Tyr Gly Phe Met Leu Ser Ile
        275                 280                 285
Ser Pro Arg Leu Thr Leu Ser Leu Leu His Met Pro Phe Thr Ile
    290                 295                 300
Ala Ala Glu Lys Val Tyr Asn Thr Arg His Gln Glu Val Leu Arg Glu
305                 310                 315                 320
Ile Gln Asp Ala Val Ala Arg Ala Gly Gln Val Val Arg Glu Ala Val
                325                 330                 335
Gly Gly Leu Gln Thr Val Arg Ser Phe Gly Ala Glu Glu His Glu Val
                340                 345                 350
Cys Arg Tyr Lys Glu Ala Leu Glu Gln Cys Arg Gln Leu Tyr Trp Arg
            355                 360                 365
Arg Asp Leu Glu Arg Ala Leu Tyr Leu Leu Val Arg Arg Val Leu His
            370                 375                 380
Leu Gly Val Gln Met Leu Met Leu Ser Cys Gly Leu Gln Gln Met Gln
385                 390                 395                 400
Asp Gly Glu Leu Thr Gln Gly Ser Leu Leu Ser Phe Met Ile Tyr Gln
                405                 410                 415
Glu Ser Val Gly Ser Tyr Val Gln Thr Leu Val Tyr Ile Tyr Gly Asp
                420                 425                 430
Met Leu Ser Asn Val Gly Ala Ala Glu Lys Val Phe Ser Tyr Met Asp
            435                 440                 445
Arg Gln Pro Asn Leu Pro Ser Pro Gly Thr Leu Ala Pro Thr Thr Leu
    450                 455                 460
Gln Gly Val Val Lys Phe Gln Asp Val Ser Phe Ala Tyr Pro Asn Arg
465                 470                 475                 480
Pro Asp Arg Pro Val Leu Lys Gly Leu Thr Phe Thr Leu Arg Pro Gly
                485                 490                 495
Glu Val Thr Ala Leu Val Gly Pro Asn Gly Ser Gly Lys Ser Thr Val
                500                 505                 510
Ala Ala Leu Leu Gln Asn Leu Tyr Gln Pro Thr Gly Gly Gln Val Leu
            515                 520                 525
Leu Asp Glu Lys Pro Ile Ser Gln Tyr Glu His Cys Tyr Leu His Ser
    530                 535                 540
Gln Val Val Ser Val Gly Gln Glu Pro Val Leu Phe Ser Gly Ser Val
545                 550                 555                 560
Arg Asn Asn Ile Ala Tyr Gly Leu Gln Ser Cys Glu Asp Asp Lys Val
                565                 570                 575
Met Ala Ala Gln Ala Ala His Ala Asp Asp Phe Ile Gln Glu Met
            580                 585                 590
Glu His Gly Ile Tyr Thr Asp Val Gly Glu Lys Gly Ser Gln Leu Ala
            595                 600                 605
Ala Gly Gln Lys Gln Arg Leu Ala Ile Ala Arg Ala Leu Val Arg Asp
    610                 615                 620
Pro Arg Val Leu Ile Leu Asp Glu Ala Thr Ser Ala Leu Asp Val Gln
625                 630                 635                 640
Cys Glu Gln Ala Leu Gln Asp Trp Asn Ser Arg Gly Asp Arg Thr Val
            645                 650                 655
Leu Val Ile Ala His Arg Leu Gln Thr Val Gln Arg Ala His Gln Ile
            660                 665                 670
Leu Val Leu Gln Glu Gly Lys Leu Gln Lys Leu Ala Gln Leu
    675                 680                 685
```

<210> SEQ ID NO 12
<211> LENGTH: 702
<212> TYPE: PRT
<213> ORGANISM: Mus musculus

<400> SEQUENCE: 12

```
Met Ala Leu Ser Tyr Leu Arg Pro Trp Val Ser Leu Leu Ala Asp
 1               5                  10                  15

Met Ala Leu Leu Gly Leu Leu Gln Gly Ser Leu Gly Asn Leu Leu Pro
                20                  25                  30

Gln Gly Leu Pro Gly Leu Trp Ile Glu Gly Thr Leu Arg Leu Gly Val
            35                  40                  45

Leu Trp Gly Leu Leu Lys Val Gly Glu Leu Leu Gly Leu Val Gly Thr
    50                  55                  60

Leu Leu Pro Leu Leu Cys Leu Ala Thr Pro Leu Phe Phe Ser Leu Arg
65                  70                  75                  80

Ala Leu Val Gly Gly Thr Ala Ser Thr Ser Val Val Arg Val Ala Ser
                85                  90                  95

Ala Ser Trp Gly Trp Leu Leu Ala Gly Tyr Gly Ala Val Ala Leu Ser
            100                 105                 110

Trp Ala Val Trp Ala Val Leu Ser Pro Ala Gly Val Gln Glu Lys Glu
        115                 120                 125

Pro Gly Gln Glu Asn Arg Thr Leu Met Lys Arg Leu Leu Lys Leu Ser
    130                 135                 140

Arg Pro Asp Leu Pro Phe Leu Ile Ala Ala Phe Phe Leu Val Val
145                 150                 155                 160

Ala Val Trp Gly Glu Thr Leu Ile Pro Arg Tyr Ser Arg Val Ile
                165                 170                 175

Asp Ile Leu Gly Gly Asp Phe Asp Pro Asp Ala Phe Ala Ser Ala Ile
            180                 185                 190

Phe Phe Met Cys Leu Phe Ser Val Gly Ser Ser Phe Ser Ala Gly Cys
        195                 200                 205

Arg Gly Gly Ser Phe Leu Phe Thr Met Ser Arg Ile Asn Leu Arg Ile
    210                 215                 220

Arg Glu Gln Leu Phe Ser Ser Leu Leu Arg Gln Asp Leu Gly Phe Phe
225                 230                 235                 240

Gln Glu Thr Lys Thr Gly Glu Leu Asn Ser Arg Leu Ser Ser Asp Thr
                245                 250                 255

Ser Leu Met Ser Arg Trp Leu Pro Phe Asn Ala Asn Ile Leu Leu Arg
            260                 265                 270

Ser Leu Val Lys Val Val Gly Leu Tyr Phe Phe Met Leu Gln Val Ser
        275                 280                 285

Pro Arg Leu Thr Phe Leu Ser Leu Leu Asp Leu Pro Leu Thr Ile Ala
    290                 295                 300

Ala Glu Lys Val Tyr Asn Pro Arg His Gln Ala Val Leu Lys Glu Ile
305                 310                 315                 320

Gln Asp Ala Val Ala Lys Ala Gly Gln Val Val Arg Glu Ala Val Gly
                325                 330                 335

Gly Leu Gln Thr Val Arg Ser Phe Gly Ala Glu Glu Gln Glu Val Ser
            340                 345                 350

His Tyr Lys Glu Ala Leu Glu Arg Cys Arg Gln Leu Trp Trp Arg Arg
        355                 360                 365

Asp Leu Glu Lys Asp Val Tyr Leu Val Ile Arg Arg Val Met Ala Leu
    370                 375                 380
```

```
Gly Met Gln Val Leu Ile Leu Asn Cys Gly Val Gln Ile Leu Ala
385                 390                 395                 400

Gly Glu Val Thr Arg Gly Gly Leu Leu Ser Phe Leu Leu Tyr Gln Glu
                405                 410                 415

Glu Val Gly Gln Tyr Val Arg Asn Leu Val Tyr Met Tyr Gly Asp Met
            420                 425                 430

Leu Ser Asn Val Gly Ala Ala Glu Lys Val Phe Ser Tyr Leu Asp Arg
        435                 440                 445

Lys Pro Asn Leu Pro Gln Pro Gly Ile Leu Ala Pro Pro Trp Leu Glu
450                 455                 460

Gly Arg Val Glu Phe Gln Asp Val Ser Phe Ser Tyr Pro Arg Arg Pro
465                 470                 475                 480

Glu Lys Pro Val Leu Gln Gly Leu Thr Phe Thr Leu His Pro Gly Thr
                485                 490                 495

Val Thr Ala Leu Val Gly Pro Asn Gly Ser Gly Lys Ser Thr Val Ala
            500                 505                 510

Ala Leu Leu Gln Asn Leu Tyr Gln Pro Thr Gly Gly Gln Leu Leu Leu
        515                 520                 525

Asp Gly Glu Pro Leu Thr Glu Tyr Asp His His Tyr Leu His Arg Gln
530                 535                 540

Val Val Leu Val Gly Gln Glu Pro Val Leu Phe Ser Gly Ser Val Lys
545                 550                 555                 560

Asp Asn Ile Ala Tyr Gly Leu Arg Asp Cys Glu Asp Ala Gln Val Met
                565                 570                 575

Ala Ala Ala Gln Ala Ala Cys Ala Asp Asp Phe Ile Gly Glu Met Thr
            580                 585                 590

Asn Gly Ile Asn Thr Glu Ile Gly Glu Lys Gly Gly Gln Leu Ala Val
        595                 600                 605

Gly Gln Lys Gln Arg Leu Ala Ile Ala Arg Ala Leu Val Arg Asn Pro
610                 615                 620

Arg Val Leu Ile Leu Asp Glu Ala Thr Ser Ala Leu Asp Ala Gln Cys
625                 630                 635                 640

Glu Gln Ala Leu Gln Asn Trp Arg Ser Gln Gly Asp Arg Thr Met Leu
                645                 650                 655

Val Ile Ala His Arg Leu His Thr Val Gln Asn Ala Asp Gln Val Leu
            660                 665                 670

Val Leu Lys Gln Gly Arg Leu Val Glu His Asp Gln Leu Arg Asp Gly
        675                 680                 685

Gln Asp Val Tyr Ala His Leu Val Gln Gln Arg Leu Glu Ala
690                 695                 700

<210> SEQ ID NO 13
<211> LENGTH: 703
<212> TYPE: PRT
<213> ORGANISM: Rattus sp.

<400> SEQUENCE: 13

Met Ala Leu Ser His Pro Arg Pro Trp Ala Ser Leu Leu Leu Val Asp
  1               5                  10                  15

Leu Ala Leu Leu Gly Leu Leu Gln Ser Ser Leu Gly Thr Leu Leu Pro
                20                  25                  30

Pro Gly Leu Pro Gly Leu Trp Leu Glu Gly Thr Leu Arg Leu Gly Val
            35                  40                  45

Leu Trp Gly Leu Leu Lys Val Gly Gly Leu Leu Arg Leu Val Gly Thr
```

```
                50                  55                  60
Phe Leu Pro Leu Cys Leu Thr Asn Pro Leu Phe Phe Ser Leu Arg
 65                  70                  75                  80

Ala Leu Val Gly Ser Thr Met Ser Thr Ser Val Val Arg Val Ala Ser
                 85                  90                  95

Ala Ser Trp Gly Trp Leu Leu Ala Asp Tyr Gly Ala Val Ala Leu Ser
                100                 105                 110

Leu Ala Val Trp Ala Val Leu Ser Pro Ala Gly Ala Gln Glu Lys Glu
                115                 120                 125

Pro Gly Gln Glu Asn Asn Arg Ala Leu Met Ile Arg Leu Leu Arg Leu
    130                 135                 140

Ser Lys Pro Asp Leu Pro Phe Leu Ile Val Ala Phe Ile Phe Leu Ala
145                 150                 155                 160

Met Ala Val Trp Trp Glu Met Phe Ile Pro His Tyr Ser Gly Arg Val
                165                 170                 175

Ile Asp Ile Leu Gly Gly Asp Phe Asp Pro Asp Ala Phe Ala Ser Ala
                180                 185                 190

Ile Phe Phe Met Cys Leu Phe Ser Val Gly Ser Ser Leu Ser Ala Gly
                195                 200                 205

Cys Arg Gly Gly Ser Phe Leu Phe Ala Glu Ser Arg Ile Asn Leu Arg
    210                 215                 220

Ile Arg Glu Gln Leu Phe Ser Ser Leu Leu Arg Gln Asp Leu Ala Phe
225                 230                 235                 240

Phe Gln Glu Thr Lys Thr Gly Glu Leu Asn Ser Arg Leu Ser Ser Asp
                245                 250                 255

Thr Ser Leu Met Ser Gln Trp Leu Ser Leu Asn Ala Asn Ile Leu Leu
                260                 265                 270

Arg Ser Leu Val Lys Val Gly Leu Tyr Tyr Phe Met Leu Gln Val
    275                 280                 285

Ser Pro Arg Leu Thr Phe Leu Ser Leu Leu Asp Leu Pro Leu Thr Ile
    290                 295                 300

Ala Ala Glu Lys Val Tyr Asn Pro Arg His Gln Ala Val Leu Lys Glu
305                 310                 315                 320

Ile Gln Asp Ala Val Ala Lys Ala Gly Gln Val Val Arg Glu Ala Val
                325                 330                 335

Gly Gly Leu Gln Thr Val Arg Ser Phe Gly Ala Glu Glu Gln Glu Val
                340                 345                 350

Arg Arg Tyr Lys Glu Ala Leu Glu Arg Cys Arg Gln Leu Trp Trp Arg
                355                 360                 365

Arg Asp Leu Glu Lys Ser Leu Tyr Leu Val Ile Gln Arg Val Met Ala
    370                 375                 380

Leu Gly Met Gln Val Leu Ile Leu Asn Val Gly Val Gln Gln Ile Leu
385                 390                 395                 400

Ala Gly Glu Val Thr Arg Gly Gly Leu Leu Ser Phe Leu Leu Tyr Gln
                405                 410                 415

Glu Glu Val Gly His His Val Gln Asn Leu Val Tyr Met Tyr Gly Asp
                420                 425                 430

Met Leu Ser Asn Val Gly Ala Ala Glu Lys Val Phe Ser Tyr Leu Asp
                435                 440                 445

Arg Arg Pro Asn Leu Pro Asn Pro Gly Thr Leu Ala Pro Pro Arg Leu
    450                 455                 460

Glu Gly Arg Val Glu Phe Gln Asp Val Ser Phe Ser Tyr Pro Ser Arg
465                 470                 475                 480
```

```
Pro Glu Lys Pro Val Leu Gln Gly Leu Thr Phe Thr Leu His Pro Gly
            485                 490                 495

Lys Val Thr Ala Leu Val Gly Pro Asn Gly Ser Gly Lys Ser Thr Val
            500                 505                 510

Ala Ala Leu Leu Gln Asn Leu Tyr Gln Pro Thr Gly Gly Gln Leu Leu
            515                 520                 525

Leu Asp Gly Glu Pro Leu Val Gln Tyr Asp His His Tyr Leu His Arg
            530                 535                 540

Gln Val Leu Val Gly Gln Glu Pro Val Leu Phe Ser Gly Ser Val
545                 550                 555                 560

Lys Asp Asn Ile Ala Tyr Gly Leu Arg Asp Cys Glu Asp Ala Gln Val
            565                 570                 575

Met Ala Ala Gln Ala Ala Cys Ala Asp Asp Phe Ile Gly Glu Met
            580                 585                 590

Thr Asn Gly Ile Asn Thr Glu Ile Gly Glu Lys Gly Ser Gln Leu Ala
            595                 600                 605

Val Gly Gln Lys Gln Arg Leu Ala Ile Ala Arg Ala Leu Val Arg Asn
            610                 615                 620

Pro Arg Val Leu Ile Leu Asp Glu Ala Thr Ser Ala Leu Asp Ala Glu
625                 630                 635                 640

Cys Glu Gln Ala Leu Gln Thr Trp Arg Ser Gln Glu Asp Arg Thr Met
            645                 650                 655

Leu Val Ile Ala His Arg Leu His Thr Val Gln Asn Ala Asp Gln Val
            660                 665                 670

Leu Val Leu Lys Gln Gly Gln Leu Val Glu His Asp Gln Leu Arg Asp
            675                 680                 685

Glu Gln Asp Val Tyr Ala His Leu Val Gln Gln Arg Leu Glu Ala
            690                 695                 700

<210> SEQ ID NO 14
<211> LENGTH: 766
<212> TYPE: PRT
<213> ORGANISM: Homo sapiens

<400> SEQUENCE: 14

Met Arg Leu Trp Lys Ala Val Val Thr Leu Ala Phe Met Ser Val
 1               5                  10                  15

Asp Ile Cys Val Thr Thr Ala Ile Tyr Val Phe Ser His Leu Asp Arg
            20                  25                  30

Ser Leu Leu Glu Asp Ile Arg His Phe Asn Ile Phe Asp Ser Val Leu
            35                  40                  45

Asp Leu Trp Ala Ala Cys Leu Tyr Arg Ser Cys Leu Leu Leu Gly Ala
            50                  55                  60

Thr Ile Gly Val Ala Lys Asn Ser Ala Leu Gly Pro Arg Arg Leu Arg
65                  70                  75                  80

Ala Ser Trp Leu Val Ile Thr Leu Val Cys Leu Phe Val Gly Ile Tyr
            85                  90                  95

Ala Met Val Lys Leu Leu Leu Phe Ser Glu Val Arg Arg Pro Ile Arg
            100                 105                 110

Asp Pro Trp Phe Trp Ala Leu Phe Val Trp Thr Tyr Ile Ser Leu Gly
            115                 120                 125

Ala Ser Phe Leu Leu Trp Trp Leu Leu Ser Thr Val Arg Pro Gly Thr
            130                 135                 140

Gln Ala Leu Glu Pro Gly Ala Ala Thr Glu Ala Glu Gly Phe Pro Gly
```

```
              145                 150                 155                 160
        Ser Gly Arg Pro Pro Glu Gln Ala Ser Gly Ala Thr Leu Gln Lys
                        165                 170                 175

Leu Leu Ser Tyr Thr Lys Pro Asp Val Ala Phe Leu Val Ala Ala Ser
                        180                 185                 190

Phe Phe Leu Ile Val Ala Ala Leu Gly Glu Thr Phe Leu Pro Tyr Tyr
                        195                 200                 205

Thr Gly Arg Ala Ile Asp Gly Ile Val Ile Gln Lys Ser Met Asp Gln
                        210                 215                 220

Phe Ser Thr Ala Val Val Ile Val Cys Leu Leu Ala Ile Gly Ser Ser
        225                 230                 235                 240

Phe Ala Ala Gly Ile Arg Gly Gly Ile Phe Thr Leu Ile Phe Ala Arg
                        245                 250                 255

Leu Asn Ile Arg Leu Arg Asn Cys Leu Phe Arg Ser Leu Val Ser Gln
                        260                 265                 270

Glu Thr Ser Phe Phe Asp Glu Asn Arg Thr Gly Asp Leu Ile Ser Arg
                        275                 280                 285

Leu Thr Ser Asp Thr Thr Met Val Ser Asp Leu Val Ser Gln Asn Ile
                        290                 295                 300

Asn Val Phe Leu Arg Asn Thr Val Lys Val Thr Gly Val Val Val Phe
        305                 310                 315                 320

Met Phe Ser Leu Ser Trp Gln Leu Ser Leu Val Thr Phe Met Gly Phe
                        325                 330                 335

Pro Ile Ile Met Met Val Ser Asn Ile Tyr Gly Lys Tyr Tyr Lys Arg
                        340                 345                 350

Leu Ser Lys Glu Val Gln Asn Ala Leu Ala Arg Ala Ser Asn Thr Ala
                        355                 360                 365

Glu Glu Thr Ile Ser Ala Met Lys Thr Val Arg Ser Phe Ala Asn Glu
                        370                 375                 380

Glu Glu Glu Ala Glu Val Tyr Leu Arg Lys Leu Gln Gln Val Tyr Lys
        385                 390                 395                 400

Leu Asn Arg Lys Glu Ala Ala Tyr Met Tyr Tyr Val Trp Gly Ser
                        405                 410                 415

Gly Leu Thr Leu Leu Val Val Gln Val Ser Ile Leu Tyr Tyr Gly Gly
                        420                 425                 430

His Leu Val Ile Ser Gly Gln Met Thr Ser Gly Asn Leu Ile Ala Phe
                        435                 440                 445

Ile Ile Tyr Glu Phe Val Leu Gly Asp Cys Met Glu Ser Val Gly Ser
                        450                 455                 460

Val Tyr Ser Gly Leu Met Gln Gly Val Gly Ala Ala Glu Lys Val Phe
        465                 470                 475                 480

Glu Phe Ile Asp Arg Gln Pro Thr Met Val His Asp Gly Ser Leu Ala
                        485                 490                 495

Pro Asp His Leu Glu Gly Arg Val Asp Phe Glu Asn Val Thr Phe Thr
                        500                 505                 510

Tyr Arg Thr Arg Pro His Thr Gln Val Leu Gln Asn Val Ser Phe Ser
                        515                 520                 525

Leu Ser Pro Gly Lys Val Thr Ala Leu Val Gly Pro Ser Gly Ser Gly
                        530                 535                 540

Arg Ser Ser Cys Val Asn Ile Leu Glu Asn Phe Tyr Pro Leu Glu Gly
        545                 550                 555                 560

Gly Arg Val Leu Leu Asp Gly Lys Pro Ile Ser Ala Tyr Asp His Lys
                        565                 570                 575
```

```
Tyr Leu His Arg Val Ile Ser Leu Val Ser Gln Glu Pro Val Leu Phe
            580                 585                 590

Ala Arg Ser Ile Thr Asp Asn Ile Ser Tyr Gly Leu Pro Thr Val Pro
            595                 600                 605

Phe Glu Met Val Val Glu Ala Ala Gln Lys Ala Asn Ala His Gly Phe
            610                 615                 620

Ile Met Glu Leu Gln Asp Gly Tyr Ser Thr Glu Thr Gly Glu Lys Gly
625                 630                 635                 640

Ala Gln Leu Ser Gly Gly Gln Lys Gln Arg Val Ala Met Ala Arg Ala
            645                 650                 655

Leu Val Arg Asn Pro Pro Val Leu Ile Leu Asp Glu Ala Thr Ser Ala
            660                 665                 670

Leu Asp Ala Glu Ser Glu Tyr Leu Ile Gln Gln Ala Ile His Gly Asn
            675                 680                 685

Leu Gln Lys His Thr Val Leu Ile Ile Ala His Arg Leu Ser Thr Val
            690                 695                 700

Glu His Ala His Leu Ile Val Val Leu Asp Lys Gly Arg Val Val Gln
705                 710                 715                 720

Gln Gly Thr His Gln Gln Leu Leu Ala Gln Gly Gly Leu Tyr Ala Lys
            725                 730                 735

Leu Val Gln Arg Gln Met Leu Gly Leu Gln Pro Ala Ala Asp Phe Thr
            740                 745                 750

Ala Gly His Asn Glu Pro Val Ala Asn Gly Ser His Lys Ala
            755                 760                 765

<210> SEQ ID NO 15
<211> LENGTH: 766
<212> TYPE: PRT
<213> ORGANISM: Homo sapiens

<400> SEQUENCE: 15

Met Arg Leu Trp Lys Ala Val Val Val Thr Leu Ala Phe Met Ser Val
1               5                   10                  15

Asp Ile Cys Val Thr Thr Ala Ile Tyr Val Phe Ser His Leu Asp Arg
            20                  25                  30

Ser Leu Leu Glu Asp Ile Arg His Phe Asn Ile Phe Asp Ser Val Leu
        35                  40                  45

Asp Leu Trp Ala Ala Cys Leu Tyr Arg Ser Cys Leu Leu Leu Gly Ala
    50                  55                  60

Thr Ile Gly Val Ala Lys Asn Ser Ala Leu Gly Pro Arg Arg Leu Arg
65                  70                  75                  80

Ala Ser Trp Leu Val Ile Thr Leu Val Cys Leu Phe Val Gly Ile Tyr
                85                  90                  95

Ala Met Val Lys Leu Leu Leu Phe Ser Glu Val Arg Arg Pro Ile Arg
            100                 105                 110

Asp Pro Trp Phe Trp Ala Leu Phe Val Trp Thr Tyr Ile Ser Leu Gly
        115                 120                 125

Ala Ser Phe Leu Leu Trp Trp Leu Leu Ser Thr Val Arg Pro Gly Thr
    130                 135                 140

Gln Ala Leu Glu Pro Gly Ala Ala Thr Glu Ala Glu Gly Phe Pro Gly
145                 150                 155                 160

Ser Gly Arg Pro Pro Pro Glu Gln Ala Ser Gly Ala Thr Leu Gln Lys
                165                 170                 175

Leu Leu Ser Tyr Thr Lys Pro Asp Val Ala Phe Leu Val Ala Ala Ser
```

```
                  180              185              190
Phe Phe Leu Ile Val Ala Ala Leu Gly Glu Thr Phe Leu Pro Tyr Tyr
            195              200              205

Thr Gly Arg Ala Ile Asp Gly Ile Val Ile Gln Lys Ser Met Asp Gln
    210              215              220

Phe Ser Thr Ala Val Val Ile Val Cys Leu Ala Ile Gly Ser Ser
225              230              235              240

Phe Ala Ala Gly Ile Arg Gly Gly Ile Phe Thr Leu Ile Phe Ala Arg
                245              250              255

Leu Asn Ile Arg Leu Arg Asn Cys Leu Phe Arg Ser Leu Val Ser Gln
            260              265              270

Glu Thr Ser Phe Phe Asp Glu Asn Arg Thr Gly Asp Leu Ile Ser Arg
        275              280              285

Leu Thr Ser Asp Thr Thr Met Val Ser Asp Leu Val Ser Gln Asn Ile
        290              295              300

Asn Val Phe Leu Arg Asn Thr Val Lys Val Thr Gly Val Val Val Phe
305              310              315              320

Met Phe Ser Leu Ser Trp Gln Leu Ser Leu Val Thr Phe Met Gly Phe
                325              330              335

Pro Ile Ile Met Met Val Ser Asn Ile Tyr Gly Lys Tyr Tyr Lys Arg
            340              345              350

Leu Ser Lys Glu Val Gln Asn Ala Leu Ala Arg Ala Ser Asn Thr Ala
        355              360              365

Glu Glu Thr Ile Ser Ala Met Lys Thr Val Arg Ser Phe Ala Asn Glu
    370              375              380

Glu Glu Glu Ala Glu Val Tyr Leu Arg Lys Leu Gln Gln Val Tyr Lys
385              390              395              400

Leu Asn Arg Lys Glu Ala Ala Tyr Met Tyr Tyr Val Trp Gly Ser
                405              410              415

Gly Leu Thr Leu Leu Val Val Gln Val Ser Ile Leu Tyr Tyr Gly Gly
            420              425              430

His Leu Val Ile Ser Gly Gln Met Thr Ser Gly Asn Leu Ile Ala Phe
        435              440              445

Ile Ile Tyr Glu Phe Val Leu Gly Asp Cys Met Glu Ser Val Gly Ser
    450              455              460

Val Tyr Ser Gly Leu Met Gln Gly Val Gly Ala Ala Glu Lys Val Phe
465              470              475              480

Glu Phe Ile Asp Arg Gln Pro Thr Met Val His Asp Gly Ser Leu Ala
                485              490              495

Pro Asp His Leu Glu Gly Arg Val Asp Phe Glu Asn Val Thr Phe Thr
            500              505              510

Tyr Arg Thr Arg Pro His Thr Gln Val Leu Gln Asn Val Ser Phe Ser
        515              520              525

Leu Ser Pro Gly Lys Val Thr Ala Leu Val Gly Pro Ser Gly Ser Gly
        530              535              540

Lys Ser Ser Cys Val Asn Ile Leu Glu Asn Phe Tyr Pro Leu Glu Gly
545              550              555              560

Gly Arg Val Leu Leu Asp Gly Lys Pro Ile Ser Ala Tyr Asp His Lys
                565              570              575

Tyr Leu His Arg Val Ile Ser Leu Val Ser Gln Glu Pro Val Leu Phe
            580              585              590

Ala Arg Ser Ile Thr Asp Asn Ile Ser Tyr Gly Leu Pro Thr Val Pro
        595              600              605
```

```
Phe Glu Met Val Val Glu Ala Ala Gln Lys Ala Asn Ala His Gly Phe
            610                 615                 620

Ile Met Glu Leu Gln Asp Gly Tyr Ser Thr Glu Thr Gly Glu Lys Gly
625                 630                 635                 640

Ala Gln Leu Ser Gly Gly Lys Gln Arg Val Ala Met Ala Arg Ala
                645                 650                 655

Leu Val Arg Asn Pro Pro Val Leu Ile Leu Asn Glu Ala Thr Ser Ala
            660                 665                 670

Leu Asp Ala Glu Ser Glu Tyr Leu Ile Gln Gln Ala Ile His Gly Asn
            675                 680                 685

Leu Gln Lys His Thr Val Leu Ile Ile Ala His Arg Leu Ser Thr Val
            690                 695                 700

Glu His Ala His Leu Ile Val Val Leu Asp Lys Gly Arg Val Val Gln
705                 710                 715                 720

Gln Gly Thr His Gln Gln Leu Leu Ala Gln Gly Leu Tyr Ala Lys
                725                 730                 735

Leu Val Gln Arg Gln Met Leu Gly Leu Gln Pro Ala Ala Asp Phe Thr
            740                 745                 750

Ala Gly His Asn Glu Pro Val Ala Asn Gly Ser His Lys Ala
            755                 760                 765

<210> SEQ ID NO 16
<211> LENGTH: 234
<212> TYPE: DNA
<213> ORGANISM: Homo sapiens
<220> FEATURE:
<223> OTHER INFORMATION: Corresponds to GenBank Acc: F06569
<223> OTHER INFORMATION: All occurrences of n = any nucleotide

<400> SEQUENCE: 16
ggccaatgnc cacggcttca tcatggaact ccaggacggc tacagcacag agacagggga      60
gaagggcgcc cagctgtcag gtggccagaa gcagcgggtg gccatggncc gggctctggt     120
gcggaacccc ccagtcctca tcctggatga agccaccagc gctttggatg ccgagagcga     180
gtatctgatc cagcaggcca tccatggcaa cctgcagaag cacacggtac tcat           234

<210> SEQ ID NO 17
<211> LENGTH: 388
<212> TYPE: DNA
<213> ORGANISM: Homo sapiens
<220> FEATURE:
<223> OTHER INFORMATION: Corresponds to GenBank Acc: R25718
<223> OTHER INFORMATION: All occurrences of n = any nucleotide

<400> SEQUENCE: 17
gccaatgnca cggtttcatc atggaactcc aggacggcta cagcacagag acagggga       60 agggcgccca gctgtcaggt ggccagaagc agcgggtggc catggccgng gctctggtgc    120 ggaaccccc agtcctcatc ctggatgaag ccaccagcgc tttggatgcc gagagcgagt     180
atctgatcca gcaggccatc catggcaacc tgtcagaagc acacggtact catcatcgcg    240
caccggctga gcaccgtgga gcacgcgcac ctcattgtgg tgctggacaa gggccgcgta    300
gtgcagcagg gcacccacca gcagcttgct tgccccaggg cgggcttttta cggcaagctn    360 gttgcagcgg cagatgtttg gggtttna                                       388

<210> SEQ ID NO 18
<211> LENGTH: 20
<212> TYPE: DNA
```

-continued

```
<213> ORGANISM: Artificial Sequence
<220> FEATURE:
<223> OTHER INFORMATION: Description of Artificial Sequence: primer

<400> SEQUENCE: 18
ggatgggcct gcgcacctct                                                    20

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 19
cactcatgaa ggccaaag                                                      18

<210> SEQ ID NO 20
<211> LENGTH: 6
<212> TYPE: DNA
<213> ORGANISM: Homo sapiens

<400> SEQUENCE: 20 aataaa                                                                    6
```

ABCB9 TRANSPORTER AND USES THEREOF

RELATED INFORMATION

This application claims priority to U.S. Provisional Application Ser. No. 60/167,930 entitled "NOVEL ABCB9 TRANSPORTER AND USES THEREOF", filed on Nov. 29, 1999, the entire contents of which is hereby incorporated herein by reference. The contents of all patents, patent applications, and references cited throughout the specification are hereby incorporated by reference in their entireties.

BACKGROUND OF THE INVENTION

ABC transporter proteins represent a large superfamily of proteins with conserved features in both prokaryotes and eukaryotes. ABC transporters catalyze ATP-dependent transport of endogenous or exogenous substrates across biological membranes (Borst, P., (1997) *Seminar in Cancer Biology* 8:131–213) and/or allosterically modify the function of heterologous proteins (Higgins C F, 1995, *Cell* 82:693–696). Several ABC transporters have been associated with clinically relevant phenotypes including the phenomenon of multidrug resistance (Ambudkar S. V. et al., (1999), *Annu. Rev. Toxicol.*, 39:361–398), cystic fibrosis (Riordin J R et al., (1989) *Science* 245:1066–1073), atherosclerosis (Brooks-Wilson A et al., (1999) *Nature Genetics* 22:336–345), hyperinsulinemic hypoglycemia (Thomas P M et al., (1995) *Science* 268:46–429), macular degeneration (Allikmets R et al., (1997) *Science* 277:1805–1807), and adrenoleukodystrophy (Mosser J et al., (1993) *Nature* 361:726–730) to name but a few. While the genes associated with these disease phenotypes have been identified to some degree, it is clear that a large number of putative ABC transporters exist in the human genome, as evidenced by the partial sequences noted in various EST databases (Allikmets et al., (1996) *Hum Mol Genet* 5:1649–1655). However, the utility of such information is compromised by the absence of the full-length nucleotide sequence of the coding region of the relevant gene and its translated protein product.

SUMMARY OF THE INVENTION

The present invention is based, at least in part, on the discovery of a novel ATP Binding Cassette (ABC) transporter family member, referred to herein as ABCB9 transporter nucleic acid and protein molecules The ABCB9 transporter molecules of the present invention are useful as targets for developing modulating agents to regulate a variety of cellular processes, particularly the transport of neurotoxic molecules, e.g., β-amyloid peptide (Aβ), across cell membranes or, e.g., the blood-brain barrier (BBB). Neurotoxic molecules such as β-amyloid peptide are involved in neurological disorders such as Alzheimer's disease (see, e.g., Goate et al. (1991) *Nature* 349:704; Games et al. (1995) *Nature* 373:523; and Suzuki et al. (1994) *Science* 264:1336). Other neurological diseases involving toxic polypeptides include, e.g., prion diseases, Huntington's disease, Parkinson's disease, Amyotrophic Lateral Sclerosis, Spinocerebellar Ataxia, Frontotemporal Dementia, etc. (Hardy et al. (1998) *Science* 282:1075–1079; Wolozin et al. (2000) *Arch. Neurol.*, 57:793–796).

Accordingly, modulation of amyloid-β protein export with a modulator of the human ABCB9 transporter would be expected to modulate amyloid deposition and thus, Alzheimer's disease.

In addition, the ABCB9 transporter molecules of the invention are useful as targets for developing modulating agents of multidrug resistance. Moreover, the molecules of the present invention are useful as diagnostic and therapeutic tools.

Accordingly, in one aspect, this invention provides isolated nucleic acid molecules encoding ABCB9 transporter proteins or biologically active portions thereof, as well as nucleic acid fragments suitable as primers or hybridization probes for the detection of ABCB9-encoding nucleic acids.

In one embodiment, an ABCB9 transporter nucleic acid molecule of the invention is at least 75%, 80%, 81%, 82%, 83%, 84%, 85%, 86%, 87%, 88%, 89%, 90%, 91%, 92%, 93%, 94%, 95%, 96%, 97%, 98%, or more identical to the nucleotide sequence (e.g., to the entire length of the nucleotide sequence) shown in SEQ ID NO: 1 or 3, or a complement thereof.

In a preferred embodiment, the isolated nucleic acid molecule includes the nucleotide sequence shown in SEQ ID NO: 1 or 3, or a complement thereof. In another embodiment, the nucleic acid molecule includes SEQ ID NO: 3 and nucleotides 1–298 of SEQ ID NO: 1. In another embodiment, the nucleic acid molecule includes SEQ ID NO: 3 and nucleotides 2597–3536 of SEQ ID NO: 1.

In another embodiment, an ABCB9 transporter nucleic acid molecule includes a nucleotide sequence encoding a protein having an amino acid sequence sufficiently homologous to the amino acid sequence of SEQ ID NO: 2. In a preferred embodiment, an ABCB9 transporter nucleic acid molecule includes a nucleotide sequence encoding a protein having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or more homologous to entire length of the amino acid sequence of SEQ ID NO: 2.

In another preferred embodiment, an isolated nucleic acid molecule encodes the amino acid sequence of human ABCB9 transporter having the amino acid sequence of SEQ ID NO: 2. In yet another preferred embodiment, the nucleic acid molecule is at least 2298 nucleotides in length. In a further preferred embodiment, the nucleic acid molecule is at least 3536 nucleotides in length and encodes a protein having ABCB9 transporter activity (as described herein).

Another embodiment of the invention features nucleic acid molecules, preferably ABCB9 transporter nucleic acid molecules, which specifically detect ABCB9 transporter nucleic acid molecules relative to nucleic acid molecules encoding non-ABCB9 transporter proteins. For example, in one embodiment, such a nucleic acid molecule is at least 50, 60, 70, 80, 90, 100, 150, 200, 300, 400, 500, 500–1000, 1000–1500, 1500–2000, or 2000–2500 or more nucleotides in length and/or hybridizes under stringent conditions to a nucleic acid molecule comprising the nucleotide sequence shown in SEQ ID NO: 1, or a complement thereof. It should be understood that the nucleic acid molecule can be of a length within a range having one of the numbers listed above as a lower limit and another number as the upper limit for the number of nucleotides in length, e.g., molecules that are 60–80, 300–1000, or 150–400 nucleotides in length.

In preferred embodiments, the nucleic acid molecules are at least 15 (e.g., contiguous) nucleotides in length and hybridize under stringent conditions to nucleotides 299–2596 of SEQ ID NO: 1. In other preferred embodiments, the nucleic acid molecules comprise nucleotides 299–2596 of SEQ ID NO: 1.

In other preferred embodiments, the nucleic acid molecule encodes a naturally occurring allelic variant of a polypeptide comprising the amino acid sequence of SEQ ID NO: 2, wherein the nucleic acid molecule hybridizes to a nucleic acid molecule comprising SEQ ID NO: 1 or 3 under stringent conditions.

Another embodiment of the invention provides an isolated nucleic acid molecule which is antisense to an ABCB9 transporter nucleic acid molecule, e.g., the coding strand of an ABCB9 transporter nucleic acid molecule.

Another aspect of the invention provides a vector comprising an ABCB9 transporter nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably an ABCB9 transporter protein, by culturing in a suitable medium, a host cell, e.g., a mammalian host cell such as a non-human mammalian cell, of the invention containing a recombinant expression vector, such that the protein is produced.

Another aspect of this invention features isolated or recombinant ABCB9 transporter proteins and polypeptides. In a preferred embodiment, the protein, preferably an ABCB9 transporter protein, includes at least one transmembrane domain and has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or more homologous to the amino acid sequence of SEQ ID NO: 2. In yet another preferred embodiment, the protein, preferably an ABCB9 transporter protein, includes at least one transmembrane domain and is encoded by a nucleic acid molecule having a nucleotide sequence which hybridizes under stringent hybridization conditions to a nucleic acid molecule comprising the nucleotide sequence of SEQ ID NO: 1.

In another embodiment, the invention features fragments of the protein having the amino acid sequence of SEQ ID NO: 2, wherein the fragment comprises at least 15 amino acids (e.g., contiguous amino acids) of the amino acid sequence of SEQ ID NO: 2. In another embodiment, the protein, preferably an ABCB9 transporter protein, has the amino acid sequence of SEQ ID NO: 2.

In another embodiment, the invention features an isolated protein, preferably an ABCB9 transporter protein, which is encoded by a nucleic acid molecule consisting of a nucleotide sequence at least 75%, 80%, 81%, 82%, 83%, 84%, 85%, 86%, 87%, 88%, 89%, 90%, 91%, 92%, 93%, 94%, 95%, 96%, 97%, 98%, or more homologous to a nucleotide sequence of SEQ ID NO: 1 or 3, or a complement thereof. This invention further features an isolated protein, preferably an ABCB9 transporter protein, which is encoded by a nucleic acid molecule consisting of a nucleotide sequence which hybridizes under stringent hybridization conditions to a nucleic acid molecule comprising the nucleotide sequence of SEQ ID NO: 1 or 3, or a complement thereof.

The proteins of the present invention or portions thereof, e.g., biologically active portions thereof, can be operatively linked to a non-ABCB9 transporter polypeptide (e.g., heterologous amino acid sequences) to form fusion proteins. The invention further features antibodies, such as monoclonal or polyclonal antibodies, that specifically bind proteins of the invention, preferably ABCB9 transporter proteins. In addition, the ABCB9 transporter proteins, biologically active portions thereof, or expressible nucleic acids encoding the foregoing, can be incorporated into pharmaceutical compositions, which optionally include pharmaceutically acceptable carriers.

In another aspect, the present invention provides a method for detecting the presence of an ABCB9 transporter nucleic acid molecule, protein or polypeptide in a biological sample by contacting the biological sample with an agent capable of detecting an ABCB9 transporter nucleic acid molecule, protein or polypeptide such that the presence of an ABCB9 transporter nucleic acid molecule, protein or polypeptide is detected in the biological sample.

In another aspect, the present invention provides a method for detecting the presence of ABCB9 transporter activity in a biological sample by contacting the biological sample with an agent capable of detecting an indicator of ABCB9 transporter activity such that the presence of ABCB9 transporter activity is detected in the biological sample.

In another aspect, the invention provides a method for modulating ABCB9 transporter activity comprising contacting a cell capable of expressing an ABCB9 transporter with an agent that modulates ABCB9 transporter activity such that ABCB9 transporter activity in the cell is modulated. In one embodiment, the agent inhibits ABCB9 transporter activity. In another embodiment, the agent modulates the ability of the ABCB9 transporter to allosterically modify the function of other membrane proteins. In another embodiment, the agent stimulates ABCB9 transporter activity. In one embodiment, the agent is an antibody that specifically binds to an ABCB9 transporter protein. In another embodiment, the agent modulates expression of ABCB9 transporter by modulating transcription of an ABCB9 transporter gene or translation of an ABCB9 transporter mRNA. In yet another embodiment, the agent is a nucleic acid molecule having a nucleotide sequence that is antisense to the coding strand of an ABCB9 transporter mRNA or an ABCB9 transporter gene.

In one embodiment, the methods of the present invention are used to treat a subject having a disorder characterized by aberrant or unwanted ABCB9 transporter protein or nucleic acid expression or activity by administering an agent which is an ABCB9 transporter modulator to the subject. In one embodiment, the ABCB9 transporter modulator is an ABCB9 transporter protein. In another embodiment the ABCB9 transporter modulator is an ABCB9 transporter nucleic acid molecule. In yet another embodiment, the ABCB9 transporter modulator is a polypeptide antibody (or fragment thereof), peptide, peptidomimetic, or other small molecule, e.g. a molecule that is carbohydrate-based, lipid-based, nucleic acid-based, natural organic-based, or synthetically derived organic-based.

The present invention also provides a diagnostic assay for identifying the presence or absence of a genetic alteration characterized by at least one of (i) aberrant modification or mutation of a gene encoding an ABCB9 transporter protein; (ii) mis-regulation of the gene; and (iii) aberrant post-translational modification of an ABCB9 transporter protein, wherein a wild-type form of the gene encodes a protein with an ABCB9 transporter activity.

In another aspect the invention provides a method for identifying a compound that binds to or modulates the activity of an ABCB9 transporter protein, by providing an indicator composition comprising an ABCB9 transporter protein having ABCB9 transporter activity, contacting the indicator composition with a test compound, and determining the effect of the test compound on ABCB9 transporter activity in the indicator composition to identify a compound that modulates the activity of an ABCB9 transporter protein, e.g., an ABCB9 transporter protein associated with a membrane.

BRIEF DESCRIPTION OF THE DRAWINGS

FIGS. 1-1 and 1-2 depict the cDNA sequence of a human ABCB9 transporter. The nucleotide sequence corresponds to nucleic acids 1 to 3536, which is also represented by SEQ ID NO: 1. The coding region without the 5' and 3' untranslated regions of the human ABCB9 transporter gene corresponds to nucleic acids 299–2596 which is represented by SEQ ID NO: 3.

FIG. 2 depicts the amino acid sequence of the ABC transporter molecule corresponding to amino acids 1 to 766 which is represented by SEQ ID NO: 2. The position and amino acid sequence of several polypeptide motifs are indicated (e.g., Walker A motif (SEQ ID NO: 4); ABC transporter signature (SEQ ID NO: 5); and Walker B motif (SEQ ID NO: 6)).

FIGS. 3-1, 3-2, and 3-3 depict an amino acid sequence alignment of the human ABCB9 transporter polypeptide (SEQ ID NO: 2) compared with polypeptides found in various species (e.g., rat TAPL (SEQ ID NO: 7); human ABCB2 (SEQ ID NO: 8); mouse TAP1 (SEQ ID NO: 9); rat TAP1 (SEQ ID NO: 10); human ABCB3 (SEQ ID NO: 11); mouse TAP2 (SEQ ID NO: 12); and rat TAP2 (SEQ ID NO: 13). The symbols (:) and (*) represent, respectively, amino acid residue positions having similarity or identity.

DETAILED DESCRIPTION OF THE INVENTION

Figure 4:
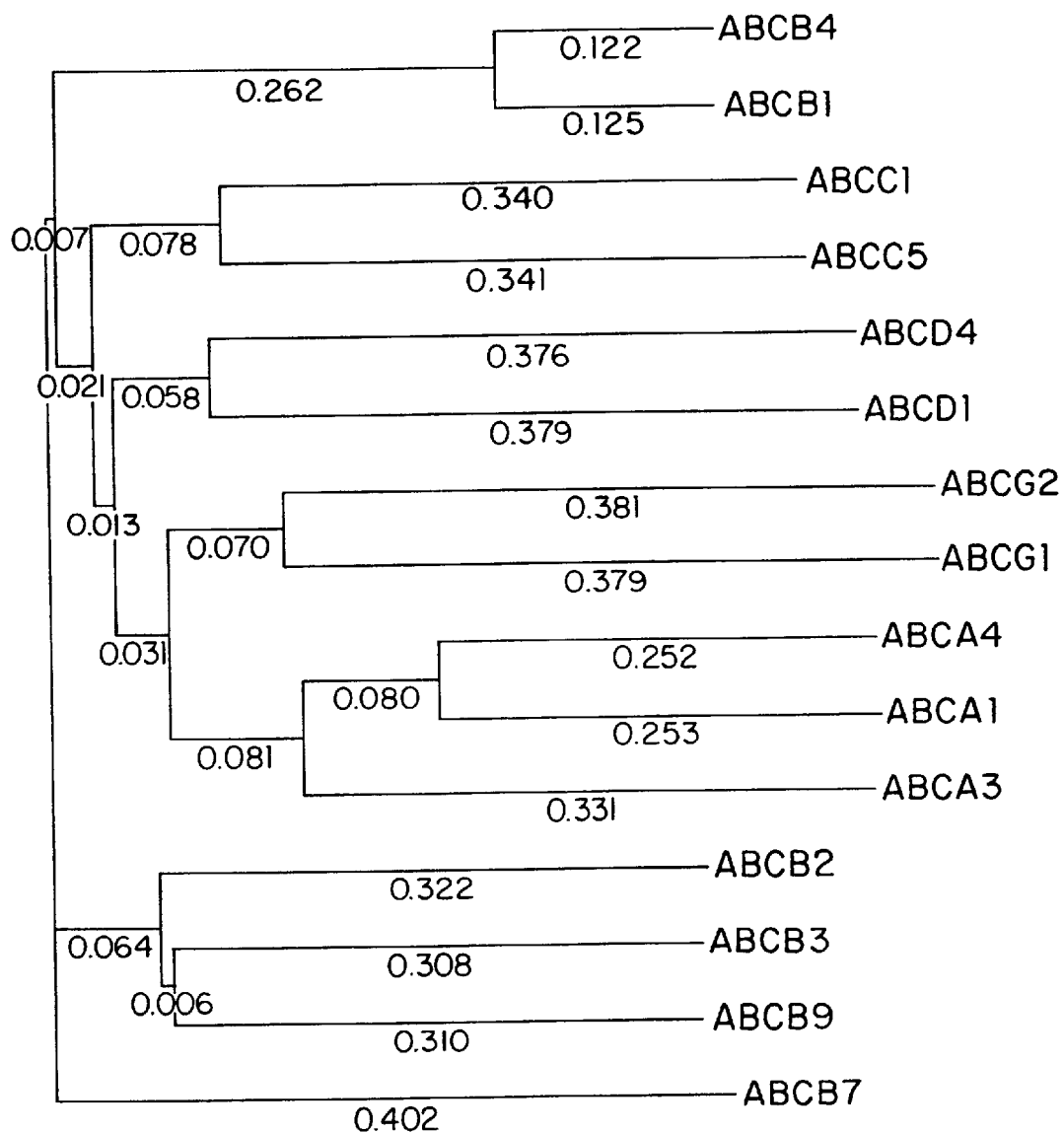
FIG. 4 depicts the probable lineage of some of the ABC transporter proteins, including human ABCB9.

The present invention is based, at least in part, on the discovery of novel ATP Binding Cassette (ABC) transporter family members, referred to herein as ABCB9 transporter nucleic acid and protein molecules. ABC transporter molecules are transmembrane proteins which catalyze ATP-dependent transport of endogenous or exogenous substrates across biological membranes. ABC transporters have been associated with the transport of polypeptides, e.g., a neurotoxic polypeptide, such as β-amyloid, which is involved in Alzheimer's disease. Other neurological diseases caused by neurotoxic polypeptides include prion diseases, Parkinson's disease, Huntington's disease, etc. (for a review, see Hardy et al. (1998) Science 282: 1075–1079). In particular, ABC transporters are associated with the transport of substrates across the blood-brain-barrier. In addition, ABC transporters are associated with multidrug resistance found in cells especially, e.g., cells that are refractory to cytotoxic anticancer drugs (Borst, P. (1997) *Sem. Cancer Bio.* 8:131–134).

Accordingly, the ABCB9 transporter molecules of the invention are suitable targets for developing novel diagnostic targets and therapeutic agents to control cellular transport in cells of the brain (e.g., neuronal cells) and transport across the blood-brain-barrier. Moreover, the ABCB9 transporter molecules are suitable targets for developing diagnostic targets and therapeutic agents for detecting and/or treating cells or tissues having multidrug resistance, e.g., a cancer.

In particular, the novel human ABCB9 transporter molecules described herein are believed to have one or more of the following functions and/or applications:

ABC transporters expressed in the brain are implicated in the transport of substrates through the blood brain barrier (Schinkel A. H., et al, (1994) *Cell*, 77, 491) and therefore identification of the sequence of the human ABCB9 transporter described herein affords the development of new strategies for altering the function of the blood brain barrier. Given that many drugs of potential utility in treating diseases of the brain are discarded because they do not enter the brain at therapeutically relevant concentrations, the present invention allows for the development of strategies to assist in the delivery of drugs to the brain.

ABC transporters expressed in the brain (as described in, e.g., U.S. patent application Ser. No. 08/847,616, the text of which is incorporated herein) are potential transporters for the β-amyloid peptide, a peptide whose deposition in senile plaques is a fundamental feature of Alzheimer's disease. Thus, identifying novel transporters that regulate β-amyloid deposition is crucial in developing therapeutic treatment for Alzheimer's disease.

The human homologue of the *Drosophila melanogaster* white gene has been reported to be associated with mood and panic disorders (Nakamura M et al., (1999), *Mol. Psychiatry*, 4, 155–162), and this gene is a member of the superfamily of ABC transporters. The human ABCB9 transporter of the invention is also expressed in the brain, and, accordingly, may be involved in mood and panic disorders. Identification of the sequence of human ABC transporter described herein allows for the development of new treatments for mood and panic disorders.

ABC transporters have been shown to be involved in the phenomenon of multidrug resistance (Ling, V., (1997) *Cancer Chemother Pharmacol* 40:S3–S8. The present invention will allow precise determination of the ability of ABCB9 to contribute to the multidrug resistance phenotype and the design of agents capable of ameliorating multidrug resistance using techniques similar to those described by Boer, R., et al. ((1996) *European Journal of Cancer*, 32A:857–861).

The human ABC1 protein has been shown to be associated with cholesterol efflux and mutated forms cause Tangier disease and familial high-density lipoprotein deficiency (Brooks-Wilson A. et al, Bodzioch M. et al, Rust S. et al, *Nature Genetics*, 22, 336–345, 347–351, 352–355 respectively). As the ABC1 protein is a homologue of the ABCB9 protein, human ABCB9 may also be found to be a cholesterol transporter. Identification of the sequence of human ABCB9 allows for the development of new treatments for diseases involving cholesterol misregulation.

The mouse abc1 protein has been implicated in interleukin-1β (IL-1β) secretion from macrophages (Hamon Y. et al, 1997, *Blood*, 90, 2911–2915). IL-1β is a mediator of inflammatory reactions, and agents able to impair its production or secretion are of potential therapeutic importance. Thus, identification of the related sequence of human ABCB9 allows for the development of new treatments for inflammatory diseases.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

For example, the family of ABC transporter proteins comprise at least one "transmembrane domain" and preferably two transmembrane domains. As used herein, the term "transmembrane domain" includes an amino acid sequence of about 18 amino acid residues in length which spans the plasma membrane. More preferably, a transmembrane domain includes about at least 18, 20, 25, 30, 35, 40, or 45 residues or more and spans the plasma membrane. Transmembrane domains are described in, for example, Zagotta W. N. et al, (1996) *Annual Rev. Neuronsci*. 19: 235–63, the contents of which are incorporated herein by reference. One or more of these transmembrane domains may associate to form a membrane-spanning domain.

Isolated proteins of the present invention, preferably ABCB9 transporter proteins, have an amino acid sequence sufficiently homologous to the amino acid sequence of SEQ ID NO: 2 or are encoded by a nucleotide sequence sufficiently homologous to SEQ ID NO: 1 or 3. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 60% homology, more preferably 70%–80%, and even more preferably 90–95% homology across the amino acid sequences of the domains and contain at least one and preferably two structural domains or motifs, are defined herein as sufficiently homologous. Furthermore, amino acid or nucleotide sequences which share at least 60%, more preferably 70–80%, or 90–95% homology and share a common functional activity are defined herein as sufficiently homologous.

As used interchangeably herein, "ABCB9 transporter activity", "biological activity of an ABCB9 transporter" or "functional activity of an ABCB9 transporter", refers to an activity exerted by an ABCB9 transporter protein, polypeptide or nucleic acid molecule on an ABCB9 transporter responsive cell or on an ABCB9 transporter protein substrate, as determined in vivo, or in vitro, according to standard techniques.

Preferably, an ABCB9 transporter activity has the ability to act as an energy-dependent (ATP) molecular pump. In one embodiment, an ABCB9 activity is a direct activity, such as an association with a membrane-associated protein and/or the transport of an endogenous or exogenous substrate across a biological membrane. In another embodiment, the ABCB9 activity is the ability of the polypeptide to allosterically modify the function of other membrane proteins. For example, in some cells, modulation of p-glycoprotein by an ABC transporter modulator has been shown to alter the magnitude of volume-activated chloride currents (reviewed in Higgins, C. F. Volume-activated chloride currents associated with the multidrug resistance P-glycoprotein, *J.* *Physiol*. 482:31S–36S (1995)). Thus, in this model, p-glycoprotein and other ABC transporters have multiple functions, one of which is to allosterically modify the function of the other membrane proteins.

The present invention is consistent with a model in which the allosteric modification of other membrane proteins by e.g., an ABCB9 transporter, is responsible for a change in the transport of a substrate, e.g., β-amyloid, a cytotoxic drug, or other small molecule. Accordingly, an ABCB9 activity is at least one or more of the following activities:

(i) activation of an ABCB9-dependent signal transduction pathway;

(ii) modulation of the transport of a substrate (e.g., a cytotoxic drug, β-amyloid) across a membrane;

(iii) interaction of an ABCB9 protein with a non-ABCB9 membrane-associated molecule;

(iv) modulation of the development or differentiation of an ABCB9-expressing cell;

(v) modulation of the development or differentiation of a non-ABCB9-expressing cell;

(vi) modulation of the homeostasis of an ABCB9-expressing cell; and (vii) modulation of the homeostasis of a non-ABCB9-expressing cell.

Accordingly, another embodiment of the invention features isolated ABCB9 transporter proteins and polypeptides having an ABCB9 transporter activity. Preferred proteins are ABCB9 transporter proteins having at least one transmembrane domain, preferably two transmembrane domains, and, preferably, ABCB9 transporter activity.

The nucleotide sequence of the isolated human ABCB9 transporter protein cDNA and the predicted amino acid sequence of the human ABCB9 transporter polypeptide correspond to SEQ ID NO: 1 and SEQ ID NO: 2, respectively.

The human ABCB9 transporter gene, which is approximately 3536 nucleotides in length, encodes a protein having a molecular weight of approximately 117.2 kDa and which is approximately 766 amino acid residues in length.

Various aspects of the invention are described in further detail in the following subsections:

I. Isolated Nucleic Acid Molecules

One aspect of the invention pertains to isolated nucleic acid molecules that encode ABCB9 transporter proteins or biologically active portions thereof, as well as nucleic acid fragments sufficient for use as hybridization probes to identify ABCB9-encoding nucleic acid molecules (e.g., ABCB9 transporter mRNA) and fragments for use as PCR primers for the amplification or mutation of ABCB9 transporter nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated ABCB9 transporter nucleic acid molecule can contain less than about 5 kb, 4kb, 3kb, 2kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO: 1 or 3, or a portion thereof, can be isolated using standard molecular biology techniques and the sequence information provided herein. Using all or portion of the nucleic acid sequence of SEQ ID NO: 1 or 3 as a hybridization probe, ABCB9 transporter nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989). Moreover, a nucleic acid molecule encompassing all or a portion of SEQ ID NO: 1 or 3 can be isolated by the polymerase chain reaction (PCR) using synthetic oligonucleotide primers designed based upon the sequence of SEQ ID NO: 1 or 3.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to ABCB9 transporter nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO: 1. The sequence of SEQ ID NO: 1 corresponds to the human ABCB9 cDNA. This cDNA comprises sequences encoding the human ABCB9 protein (i.e., "the coding region", from nucleotides 299–2597), as well as 5' untranslated sequences (nucleotides 1–298) and 3' untranslated sequences (nucleotides 2598–3536). Alternatively, the nucleic acid molecule can comprise only the coding region of SEQ ID NO: 1(e.g., nucleotides 299–2597, corresponding to SEQ ID NO: 3).

In another preferred embodiment, an isolated nucleic acid molecule of the invention comprises a nucleic acid molecule which is a complement of the nucleotide sequence shown in SEQ ID NO: 1 or 3, or a portion of any of these nucleotide sequences. A nucleic acid molecule which is complementary to the nucleotide sequence shown in SEQ ID NO: 1 or 3 is one which is sufficiently complementary to the nucleotide sequence shown in SEQ ID NO: 1 or 3 such that it can hybridize to the nucleotide sequence shown in SEQ ID NO: 1 or 3, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 86%, 87%, 88%, 89%, 90%, 91%, 92%, 93%, 94%, 95%, 96%, 97%, 98%, or more homologous to the entire length of the nucleotide sequence shown in SEQ ID NO: 1 or 3, or a portion of any of these nucleotide sequences.

Moreover, the nucleic acid molecule of the invention can comprise only a portion of the nucleic acid sequence of SEQ ID NO: 1 or 3, for example, a fragment which can be used as a probe or primer or a fragment encoding a portion of an ABCB9 transporter protein, e.g., a biologically active portion of an ABCB9 transporter protein. The nucleotide sequence determined from the cloning of the ABCB9 transporter gene allows for the generation of probes and primers designed for use in identifying and/or cloning other ABCB9 transporter family members, as well as ABCB9 transporter homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO: 1 or 3 of an anti-sense sequence of SEQ ID NO: 1 or 3, or of a naturally occurring allelic variant or mutant of SEQ ID NO: 1 or 3. In an exemplary embodiment, a nucleic acid molecule of the present invention comprises a nucleotide sequence which is greater than 50, 60, 70, 80, 90, 100, 150, 200, 300, 400, 500–1000, 1000–1500, 1500–2000, or 2000–2500 or more nucleotides in length and hybridizes under stringent hybridization conditions to a nucleic acid molecule of SEQ ID NO: 1 or 3.

Probes based on the ABCB9 transporter nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an ABCB9 transporter protein, such as by measuring a level of an ABCB9-encoding nucleic acid in a sample of cells from a subject e.g., detecting ABCB9 transporter mRNA levels or determining whether a genomic ABCB9 transporter gene has been mutated or deleted.

A nucleic acid fragment encoding a "biologically active portion of an ABCB9 transporter protein" can be prepared by isolating a portion of the nucleotide sequence of SEQ ID NO: 1 or 3 which encodes a polypeptide having an ABCB9 transporter biological activity (the biological activities of the ABCB9 transporter proteins are described herein), expressing the encoded portion of the ABCB9 transporter protein (e.g., by recombinant expression in vitro) and assessing the activity of the encoded portion of the ABCB9 transporter protein.

The invention further encompasses nucleic acid molecules that differ from the nucleotide sequence shown in SEQ ID NO: 1 or 3 due to degeneracy of the genetic code and thus encode the same ABCB9 transporter proteins as those encoded by the nucleotide sequence shown in SEQ ID NO: 1 or 3. In another embodiment, an isolated nucleic acid molecule of the invention has a nucleotide sequence encoding a protein having an amino acid sequence shown in SEQ ID NO: 2.

In addition to the ABCB9 transporter nucleotide sequences shown in SEQ ID NO: 1 or 3, it will be appreciated by those skilled in the art that DNA sequence polymorphisms that lead to changes in the amino acid sequences of the ABCB9 transporter proteins may exist within a population (e.g., the human population). Such genetic polymorphism in the ABCB9 transporter genes may exist among individuals within a population due to natural allelic variation. As used herein, the terms "gene" and "recombinant gene" refer to nucleic acid molecules which include an open reading frame encoding an ABCB9 transporter protein, preferably a mammalian ABCB9 transporter protein, and can further include non-coding regulatory sequences, and introns.

Allelic variants of a human ABCB9 transporter include both functional and non-functional ABCB9 transporter proteins. Functional allelic variants are naturally occurring amino acid sequence variants of the human ABCB9 transporter that maintain the ability to bind an ABCB9 transporter ligand. Functional allelic variants will typically contain only conservative substitution of one or more amino acids of SEQ ID NO: 2 or substitution, deletion or insertion of non-critical residues in non-critical regions of the protein.

Non-functional allelic variants are naturally occurring amino acid sequence variants of the human ABCB9 transporter protein that do not have the ability to either bind an ABCB9 transporter ligand. Non-functional allelic variants will typically contain a non-conservative substitution, a deletion, or insertion or premature truncation of the amino acid sequence of SEQ ID NO: 2 or a substitution, insertion or deletion in critical residues or critical regions.

The present invention further provides non-human orthologues of the human ABCB9 transporter protein. Orthologues of the human ABCB9 transporter protein are proteins that are isolated from non-human organisms and possess the same ABCB9 transporter activity as the human ABCB9 transporter protein. Orthologues of the human ABCB9 protein can readily be identified as comprising an amino acid sequence that is substantially homologous to SEQ ID NO: 2.

Moreover, nucleic acid molecules encoding other ABCB9 transporter family members and, thus, which have a nucleotide sequence which differs from the ABCB9 transporter sequences of SEQ ID NO: 1 or 3 are intended to be within the scope of the invention. For example, another ABCB9 transporter cDNA can be identified based on the nucleotide sequence of the human ABCB9 transporter. Moreover, nucleic acid molecules encoding ABCB9 transporter proteins from different species, e.g., mammals, and which, thus, have a nucleotide sequence which differs from the ABCB9 transporter sequences of SEQ ID NO: 1 or 3 are intended to be within the scope of the invention. For example, a mouse ABCB9 transporter cDNA can be identified based on the nucleotide sequence of the human ABCB9 transporter.

Nucleic acid molecules corresponding to natural allelic variants and homologues of the ABCB9 transporter cDNAs of the invention can be isolated based on their homology to the ABCB9 transporter nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the ABCB9 transporter cDNAs of the invention can further be isolated by mapping to the same chromosome or locus as the ABCB9 transporter gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO: 1 or 3. In other embodiment, the nucleic acid is at least 30, 50, 100, 150, 200, 300, 400, 500, 600, 700, 800, 900, 1000, 1250, 1500, 1750, 2000, 2250, 2500, 2739 or more nucleotides in length. As used herein, the term "hybridizes under stringent conditions" is intended to describe conditions for hybridization and washing under which nucleotide sequences at least 75% homologous to each other typically remain hybridized to each other. Preferably, the conditions are such that sequences at least about 80%, even more preferably at least about 85%, 86%, 87%, 88%, 89%, 90%, 91%, 92%, 93%, 94%, 95%, 96%, 97%, or 98% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50° C., preferably at 55° C., more preferably at 60° C., and even more preferably at 65° C. Preferably, an isolated nucleic acid molecule of the invention that hybridizes under stringent conditions to the sequence of SEQ ID NO: 1 or 3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the ABCB9 transporter sequences that may exist in the population, the skilled artisan will further appreciate that changes can be introduced by mutation into the nucleotide sequences of SEQ ID NO: 1 or 3, thereby leading to changes in the amino acid sequence of the encoded ABCB9 transporter proteins, without altering the functional ability of the ABCB9 transporter proteins. For example, nucleotide substitutions leading to amino acid substitutions at "non-essential" amino acid residues can be made in the sequence of SEQ ID NO: 1 or 3. A "non-essential" amino acid residue is a residue that can be altered from the wild-type sequence of ABCB9 transporter (e.g., the sequence of SEQ ID NO: 2) without altering the biological activity, whereas an "essential" amino acid residue is required for biological activity.

Accordingly, another aspect of the invention pertains to nucleic acid molecules encoding ABCB9 transporter proteins that contain changes in amino acid residues that are not essential for activity. Such ABCB9 transporter proteins differ in amino acid sequence from SEQ ID NO: 2, yet retain biological activity. In one embodiment, the isolated nucleic acid molecule comprises a nucleotide sequence encoding a protein, wherein the protein comprises an amino acid sequence at least about 75%, 80%, 81%, 82%, 83%, 84%, 85%, 86%, 87%, 88%, 89%, 90%, 91%, 92%, 93%, 94%, 95%, 96%, 97%, or more homologous to SEQ ID NO: 2.

An isolated nucleic acid molecule encoding an ABCB9 transporter protein homologous to the protein of SEQ ID NO: 2 can be created by introducing one or more nucleotide substitutions, additions, or deletions into the nucleotide sequence of SEQ ID NO: 1 or 3, such that one or more amino acid substitutions, additions or deletions are introduced into the encoded protein. Mutations can be introduced into SEQ ID NO: 1 or 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an ABCB9 transporter protein is preferably replaced with another amino acid residue from the same side chain family. Alternatively, in another embodiment, mutations can be introduced randomly along all or part of an ABCB9 transporter coding sequence, such as by saturation mutagenesis, and the resultant mutants can be screened for ABCB9 transporter biological activity to identify mutants that retain activity. Following mutagenesis of SEQ ID NO: 1 or 3 the encoded protein can be expressed recombinantly and the activity of the protein can be determined.

In a preferred embodiment, a mutant ABCB9 transporter protein can be assayed for the ability to interact with a non-ABCB9 transporter molecule, e.g., an ABCB9 transporter ligand, e.g., a polypeptide or a small molecule.

In addition to the nucleic acid molecules encoding ABCB9 transporter proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire ABCB9 transporter coding strand, or to only a portion thereof. In one embodiment, an antisense nucleic acid molecule is antisense to a "coding region" of the coding strand of a nucleotide sequence encoding ABCB9. The term "coding region" refers to the region of the nucleotide sequence comprising codons which are translated into amino acids residues (e.g., the coding region of human ABCB9 is corresponds to SEQ ID NO: 3). In another embodiment, the antisense nucleic acid molecule is antisense to a "noncoding region" of the coding strand of a nucleotide sequence encoding ABCB9. The term "noncoding region" refers to 5' and 3' sequences which flank the coding region that are not translated into amino acids (i.e., also referred to as 5' and 3' untranslated regions).

Given the coding strand sequences encoding ABCB9 transporter disclosed herein (e.g., SEQ ID NO: 3), antisense nucleic acids of the invention can be designed according to the rules of Watson and Crick base pairing. The antisense nucleic acid molecule can be complementary to the entire coding region of ABCB9 transporter mRNA, but more preferably is an oligonucleotide which is antisense to only a portion of the coding or noncoding region of ABCB9 transporter mRNA. For example, the antisense oligonucleotide can be complementary to the region surrounding the translation start site of ABCB9 transporter mRNA. An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an ABCB9 transporter protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave ABCB9 transporter mRNA transcripts to thereby inhibit translation of ABCB9 transporter mRNA. A ribozyme having specificity for an ABCB9-encoding nucleic acid can be designed based upon the nucleotide sequence of an ABCB9 transporter cDNA disclosed herein (i.e., SEQ ID NO: 1). For example, a derivative of a Tetrahymena L-19 IVS RNA can be constructed in which the nucleotide sequence of the active site is complementary to the nucleotide sequence to be cleaved in an ABCB9-encoding mRNA. See, e.g., Cech et al. U.S. Pat. No. 4,987,071; and Cech et al. U.S. Pat. No. 5,116,742. Alternatively, ABCB9 transporter mRNA can be used to select a catalytic RNA having a specific ribonuclease activity from a pool of RNA molecules. See, e.g., Bartel, D. and Szostak, J. W. (1993) *Science* 261:1411–1418.

Alternatively, ABCB9 transporter gene expression can be inhibited by targeting nucleotide sequences complementary to the regulatory region of the ABCB9 transporter (e.g., the ABCB9 transporter promoter and/or enhancers) to form triple helical structures that prevent transcription of the ABCB9 transporter gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the ABCB9 transporter nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of ABCB9 transporter nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of ABCB9 transporter nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of ABCB9 transporter nucleic acid molecules can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of ABCB9 transporter nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated ABCB9 Transporter Proteins and Anti-ABCB9 Transporter Antibodies

One aspect of the invention pertains to isolated ABCB9 transporter proteins, and biologically active portions thereof, as well as polypeptide fragments suitable for use as immunogens to raise anti-ABCB9 transporter antibodies. In one embodiment, native ABCB9 transporter proteins can be isolated from cells or tissue sources by an appropriate purification scheme using standard protein purification techniques. In another embodiment, ABCB9 transporter proteins are produced by recombinant DNA techniques. Alternative to recombinant expression, an ABCB9 transporter protein or polypeptide can be synthesized chemically using standard peptide synthesis techniques.

An "isolated" or "purified" protein or biologically active portion thereof is substantially free of cellular material or other contaminating proteins from the cell or tissue source from which the ABCB9 transporter protein is derived, or substantially free from chemical precursors or other chemicals when chemically synthesized. The language "substantially free of cellular material" includes preparations of ABCB9 transporter protein in which the protein is separated from cellular components of the cells from which it is isolated or recombinantly produced. In one embodiment, the language "substantially free of cellular material" includes preparations of ABCB9 transporter protein having less than about 30% (by dry weight) of non-ABCB9 transporter protein (also referred to herein as a "contaminating protein"), more preferably less than about 20% of non-ABCB9 transporter protein, still more preferably less than about 10% of non-ABCB9 transporter protein, and most preferably less than about 5% non-ABCB9 transporter protein. When the ABCB9 transporter protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of ABCB9 transporter protein in which the protein is separated from chemical precursors or other chemicals which are involved in the synthesis of the protein. In one embodiment, the language "substantially free of chemical precursors or other chemicals" includes preparations of ABCB9 transporter protein having less than about 30% (by dry weight) of chemical precursors or non-ABCB9 transporter chemicals, more preferably less than about 20% chemical precursors or non-ABCB9 transporter chemicals, still more preferably less than about 10% chemical precursors or non-ABCB9 transporter chemicals, and most preferably less than about 5% chemical precursors or non-ABCB9 transporter chemicals.

As used herein, a "biologically active portion" of an ABCB9 transporter protein includes a fragment of an ABCB9 transporter protein which participates in an interaction between an ABCB9 transporter molecule and a non-ABCB9 transporter molecule. Biologically active portions of an ABCB9 transporter protein include peptides comprising amino acid sequences sufficiently homologous to or derived from the amino acid sequence of the ABCB9 transporter protein, e.g., the amino acid sequence shown in SEQ ID NO: 2, which include less amino acids than the full length ABCB9 transporter proteins, and exhibit at least one activity of an ABCB9 transporter protein. Typically, biologically active portions comprise a domain or motif with at least one activity of the ABCB9 transporter protein. A biologically active portion of an ABCB9 transporter protein can be a polypeptide which is, for example, 10, 25, 50, 100, 200, 300, 400, 500, 600, 700, 800 or more amino acids in length. Biologically active portions of an ABCB9 transporter protein can be used as targets for developing agents which modulate an ABCB9 transporter mediated activity.

In one embodiment, a biologically active portion of an ABCB9 transporter protein comprises at least one transmembrane domain. It is to be understood that a preferred biologically active portion of an ABCB9 transporter protein of the present invention may contain at least one transmembrane domain. Another preferred biologically active portion of an ABCB9 transporter protein may contain at least two transmembrane domains. One or more of these transmembrane domains may associate to form a membrane-spanning domain. In addition, or alternatively, the biologically active portion of the ABCB9 transporter protein may include multiple clusters of conserved residues that define an ATP binding domain. In addition, or alternatively, the biologically active portion of the ABCB9 transporter protein may comprise a Walker domain, e.g., a Walker A and/or Walker B domain (see FIG. 2.; Patel et al. (1998) *Trends Cell Biol* 8: 65–71). Identification of these domains may be facilitated using any of a number of art recognized molecular modeling techniques as described herein (see also Example 2). Moreover, other biologically active portions, in which other regions of the protein are deleted, can be prepared by recombinant techniques and evaluated for one or more of the functional activities of a native ABCB9 transporter protein.

In a preferred embodiment, the ABCB9 transporter protein has an amino acid sequence shown in SEQ ID NO: 2.

In other embodiments, the ABCB9 transporter protein is substantially homologous to SEQ ID NO: 2, and retains the functional activity of the protein of SEQ ID NO: 2, yet differs in amino acid sequence due to natural allelic variation or mutagenesis, as described in detail in subsection I above. Accordingly, in another embodiment, the ABCB9 transporter protein is a protein which comprises an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or more homologous to SEQ ID NO: 2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 70%, preferably, 80%, 90% or 100% of the length of the reference sequence (e.g., when aligning a second sequence to the ABCB9 transporter amino acid sequence of SEQ ID NO: 2 having 2001 amino acid residues, at least 600, preferably at least 800, more preferably at least 1000, even more preferably at least 1200, and even more preferably at least 1400, 1600, 1800, or 2001 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

A comparison of sequences and determination of percent identity between two sequences can be accomplished using a mathematical algorithm. In a preferred embodiment, the percent identity between two amino acid sequences is determined using standard art recognized comparison software using standard parameter settings. For example, the Needleman and Wunsch (*J. Mol. Biol.* (48):444–453 (1970)) algorithm which has been incorporated into the GAP program in the GCG software package (available at http://www.gcg.com) can be employed using either a Blossum 62 matrix or a PAM250 matrix, and a gap weight of 16, 14, 12, 10, 8, 6, or 4 and a length weight of 1, 2, 3, 4,5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to ABCB9 transporter nucleic acid molecules of the invention. BLAST protein searches can be performed with the XBLAST program, score=50, wordlength=3 to obtain amino acid sequences homologous to ABCB9 transporter protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The invention also provides ABCB9 transporter chimeric or fusion proteins. As used herein, an ABCB9 transporter "chimeric protein" or "fusion protein" comprises an ABCB9 transporter polypeptide operatively linked to a non-ABCB9 transporter polypeptide. An "ABCB9 transporter polypeptide" refers to a polypeptide having an amino acid sequence corresponding to ABCB9, whereas a "non-ABCB9 transporter polypeptide" refers to a polypeptide having an amino acid sequence corresponding to a protein which is not substantially homologous to the ABCB9 transporter protein, e.g., a protein which is different from the ABCB9 transporter protein and which is derived from the same or a different organism. Within an ABCB9 transporter fusion protein the ABCB9 transporter polypeptide can correspond to all or a portion of an ABCB9 transporter protein. In a preferred embodiment, an ABCB9 transporter fusion protein comprises at least one biologically active portion of an ABCB9 transporter protein. In another preferred embodiment, an ABCB9 transporter fusion protein comprises at least two biologically active portions of an ABCB9 transporter protein. Within the fusion protein, the term "operatively linked" is intended to indicate that the ABCB9 transporter polypeptide and the non-ABCB9 transporter polypeptide are fused in-frame to each other. The non-ABCB9 transporter polypeptide can be fused to the N-terminus or C-terminus of the ABCB9 transporter polypeptide.

For example, in one embodiment, the fusion protein is a GST-ABCB9 transporter fusion protein in which the ABCB9 transporter sequences are fused to the C-terminus of the GST sequences. Such fusion proteins can facilitate the purification of recombinant ABCB9.

In another embodiment, the fusion protein is an ABCB9 transporter protein containing a heterologous signal sequence at its N-terminus. In certain host cells (e.g., mammalian host cells), expression and/or secretion of ABCB9 transporter can be increased through use of a heterologous signal sequence.

The ABCB9 transporter fusion proteins of the invention can be incorporated into pharmaceutical compositions and administered to a subject in vivo. The ABCB9 transporter fusion proteins can be used to affect the bioavailability of an ABCB9 transporter substrate. Use of ABCB9 transporter fusion proteins may be useful therapeutically for the treatment of disorders caused by, for example, (i) aberrant modification or mutation of a gene encoding an ABCB9 transporter protein; (ii) mis-regulation of the ABCB9 transporter gene; and (iii) aberrant post-translational modification of an ABCB9 transporter protein.

Moreover, the ABCB9-fusion proteins of the invention can be used as immunogens to produce anti-ABCB9 transporter antibodies in a subject, to purify ABCB9 transporter ligands and in screening assays to identify molecules which inhibit the interaction of an ABCB9 transporter with an ABCB9 transporter substrate.

Preferably, an ABCB9 transporter chimeric or fusion protein of the invention is -produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An ABCB9 transporter-encoding nucleic acid can be cloned into such an expression vector such that the fusion moiety is linked in-frame to the ABCB9 transporter protein.

The present invention also pertains to variants of the ABCB9 transporter proteins which function as either ABCB9 transporter agonists or as ABCB9 transporter antagonists. Variants of the ABCB9 transporter proteins can be generated by mutagenesis, e.g., discrete point mutation or truncation of an ABCB9 transporter protein. An agonist of the ABCB9 transporter proteins can retain substantially the same, or a subset, of the biological activities of the naturally occurring form of an ABCB9 transporter protein. An antagonist of an ABCB9 transporter protein can inhibit one or more of the activities of the naturally occurring form of the ABCB9 transporter protein by, for example, competitively modulating an activity of an ABCB9 transporter protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the ABCB9 transporter protein.

In one embodiment, variants of an ABCB9 transporter protein which function as either ABCB9 transporter agonists (mimetics) or as ABCB9 transporter antagonists can be identified by screening combinatorial libraries of mutants, e.g., truncation mutants, of an ABCB9 transporter protein for ABCB9 transporter protein agonist or antagonist activity. In one embodiment, a variegated library of ABCB9 transporter variants is generated by combinatorial mutagenesis at the nucleic acid level and is encoded by a variegated gene library. A variegated library of ABCB9 transporter variants can be produced by, for example, enzymatically ligating a mixture of synthetic oligonucleotides into gene sequences such that a degenerate set of potential ABCB9 transporter sequences is expressible as individual polypeptides, or alternatively, as a set of larger fusion proteins (e.g., for phage display) containing the set of ABCB9 transporter sequences therein. There are a variety of methods which can be used to produce libraries of potential ABCB9 transporter variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential ABCB9 transporter sequences. Methods for synthesizing degenerate oligonucleotides are known in the art (see, e.g. Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of an ABCB9 transporter protein coding sequence can be used to generate a variegated population of ABCB9 transporter fragments for screening and subsequent selection of variants of an ABCB9 transporter protein. In one embodiment, a library of coding sequence fragments can be generated by treating a double stranded PCR fragment of an ABCB9 transporter coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the ABCB9 transporter protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of ABCB9 transporter proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify ABCB9 transporter variants (Arkin and Yourvan (1992) *Proc. Natl. Acad. Sci. USA* 89:7811–7815; Delgrave et al. (1993) *Protein Engineering* 6(3):327–331).

An isolated ABCB9 transporter protein, or a portion or fragment thereof, can be used as an immunogen to generate antibodies that bind ABCB9 transporter using standard techniques for polyclonal and monoclonal antibody preparation. A full-length ABCB9 transporter protein can be used or, alternatively, the invention provides antigenic peptide fragments of ABCB9 transporter for use as immunogens. Preferred epitopes encompassed by the antigenic peptide are regions of ABCB9 transporter that are located on the surface of the protein, e.g., hydrophilic regions, as well as regions with high antigenicity.

An ABCB9 transporter immunogen typically is used to prepare antibodies by immunizing a suitable subject, (e.g., rabbit, goat, mouse or other mammal) with the immunogen. An appropriate immunogenic preparation can contain, for example, recombinantly expressed ABCB9 transporter protein or a chemically synthesized ABCB9 transporter polypeptide. The preparation can further include an adjuvant, such as Freund's complete or incomplete adjuvant, or similar immunostimulatory agent. Immunization of a suitable subject with an immunogenic ABCB9 transporter preparation induces a polyclonal anti-ABCB9 transporter antibody response.

Accordingly, another aspect of the invention pertains to anti-ABCB9 transporter antibodies. The term "antibody" as used herein refers to immunoglobulin molecules and immunologically active portions of immunoglobulin molecules, i.e., molecules that contain an antigen binding site which specifically binds (immunoreacts with) an antigen, such as ABCB9 transporter. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind ABCB9 transporter. The term "monoclonal antibody" or "monoclonal antibody composition", as used herein, refers to a population of antibody molecules that contain only one species of an antigen binding site capable of immunoreacting with a particular epitope of ABCB9 transporter. A monoclonal antibody composition thus typically displays a single binding affinity for a particular ABCB9 transporter protein with which it immunoreacts.

Polyclonal anti-ABCB9 transporter antibodies can be prepared as described above by immunizing a suitable subject with an ABCB9 transporter immunogen. The anti-ABCB9 transporter antibody titer in the immunized subject can be monitored over time by standard techniques, such as with an enzyme linked immunosorbent assay (ELISA) using immobilized ABCB9 transporter. If desired, the antibody molecules directed against ABCB9 transporter can be isolated from the mammal (e.g., from the blood) and further purified by well known techniques, such as protein A chromatography to obtain the IgG fraction. At an appropriate time after immunization, e.g., when the anti-ABCB9 transporter antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an ABCB9 transporter immunogen as described above, and the culture supernatants of the resulting hybridoma cells are screened to identify a hybridoma producing a monoclonal antibody that binds ABCB9 transporter.

Any of the many well known protocols used for fusing lymphocytes and immortalized cell lines can be applied for the purpose of generating an anti-ABCB9 transporter monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind ABCB9, e.g., using a standard ELISA assay.

Alternative to preparing monoclonal antibody-secreting hybridomas, a monoclonal anti-ABCB9 transporter antibody can be identified and isolated by screening a recombinant combinatorial immunoglobulin library (e.g., an antibody phage display library) with ABCB9 transporter to thereby isolate immunoglobulin library members that bind ABCB9. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-ABCB9 transporter antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-ABCB9 transporter antibody (e.g., monoclonal antibody) can be used to isolate ABCB9 transporter by standard techniques, such as affinity chromatography or immunoprecipitation. An anti-ABCB9 transporter antibody can facilitate the purification of natural ABCB9 transporter from cells and of recombinantly produced ABCB9 transporter expressed in host cells. Moreover, an anti-ABCB9 transporter antibody can be used to detect ABCB9 transporter protein (e.g., in a cellular lysate or cell supernatant) in order to evaluate the abundance and pattern of expression of the ABCB9 transporter protein. Anti-ABCB9 transporter antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, $^{33}P$, $^{32}P$, or $^{3}H$.

III. Recombinant Expression Vectors and Host Cells

Another aspect of the invention pertains to vectors, preferably expression vectors, containing a nucleic acid encoding an ABCB9 transporter protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., ABCB9 transporter proteins, mutant forms of ABCB9 transporter proteins, fusion proteins, and the like).

The recombinant expression vectors of the invention can be designed for expression of ABCB9 transporter proteins in prokaryotic or eukaryotic cells. For example, ABCB9 transporter proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in ABCB9 transporter activity assays, (e.g., direct assays or competitive assays described in detail below), or to generate antibodies specific for ABCB9 transporter proteins, for example. In a preferred embodiment, an ABCB9 transporter fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the ABCB9 transporter expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, ABCB9 transporter proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev*. 1:268–277), lymphoid-specific promoters (Calame and Eaton (1988) *Adv. Immunol.* 43:235–275), in particular promoters of T cell receptors (Winoto and Baltimore (1989) *EMBO J*. 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev*. 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to ABCB9 transporter mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which an ABCB9 transporter nucleic acid molecule of the invention is introduced, e.g., an ABCB9 transporter nucleic acid molecule within a recombinant expression vector or an ABCB9 transporter nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an ABCB9 transporter protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation DEAE-dextran-mediated transfection, lipofection, or electroporation. Suitable methods for transforming or transfecting host cells can be found in Sambrook, et al. (*Molecular Cloning: A Laboratory Manual. 2nd, ed, Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an ABCB9 transporter protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an ABCB9 transporter protein. Accordingly, the invention further provides methods for producing an ABCB9 transporter protein using the host cells of the invention. In one embodiment, the method comprises culturing the host cell of the invention (into which a recombinant expression vector encoding an ABCB9 transporter protein has been introduced) in a suitable medium such that an ABCB9 transporter protein is produced. In another embodiment, the method further comprises isolating an ABCB9 transporter protein from the medium or the host cell.

The host cells of the invention can also be used to produce non-human transgenic animals. For example, in one embodiment, a host cell of the invention is a fertilized oocyte or an embryonic stem cell into which ABCB9-coding sequences have been introduced. Such host cells can then be used to create non-human transgenic animals in which exogenous ABCB9 transporter sequences have been introduced into their genome or homologous recombinant animals in which endogenous ABCB9 transporter sequences have been altered. Such animals are useful for studying the function and/or activity of an ABCB9 transporter and for identifying and/or evaluating modulators of ABCB9 transporter activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous ABCB9 transporter gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an ABCB9-encoding nucleic acid into the male pronuclei of a fertilized oocyte, e.g., by microinjection, retroviral infection, and allowing the oocyte to develop in a pseudopregnant female foster animal. The ABCB9 transporter cDNA sequence of SEQ ID NO: 1 can be introduced as a transgene into the genome of a non-human animal. Alternatively, a nonhuman homologue of a human ABCB9 transporter gene, such as a mouse or rat ABCB9 transporter gene, can be used as a transgene. Alternatively, an ABCB9 transporter gene homologue, such as another ABC transporter family member, can be isolated based on hybridization to the ABCB9 transporter cDNA sequences of SEQ ID NO: 1 or 3 (described further in subsection I above) and used as a transgene. Intronic sequences and polyadenylation signals can also be included in the transgene to increase the efficiency of expression of the transgene. A tissue-specific regulatory sequence(s) can be operably linked to an ABCB9 transporter transgene to direct expression of an ABCB9 transporter protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an ABCB9 transporter transgene in its genome and/or expression of ABCB9 transporter mRNA in tissues or cells of the animals. A transgenic founder animal can then be used to breed additional animals carrying the transgene. Moreover, transgenic animals carrying a transgene encoding an ABCB9 transporter protein can further be bred to other transgenic animals carrying other transgenes, for example, animals carrying a transgene encoding a neurotoxic polypeptide such as β-amyloid.

To create a homologous recombinant animal, a vector is prepared which contains at least a portion of an ABCB9 transporter gene into which a deletion, addition or substitution has been introduced to thereby alter, e.g., functionally disrupt, the ABCB9 transporter gene. The ABCB9 transporter gene can be a human gene (e.g., the cDNA of SEQ ID NO: 3), but more preferably, is a non-human homologue of a human ABCB9 transporter gene (e.g., a cDNA isolated by stringent hybridization with the nucleotide sequence of SEQ ID NO: 1). For example, a mouse ABCB9 transporter gene can be used to construct a homologous recombination nucleic acid molecule, e.g., a vector, suitable for altering an endogenous ABCB9 transporter gene in the mouse genome. In a preferred embodiment, the homologous recombination nucleic acid molecule is designed such that, upon homologous recombination, the endogenous ABCB9 transporter gene is functionally disrupted (i.e., no longer encodes a functional protein; also referred to as a "knock out" vector). Alternatively, the homologous recombination nucleic acid molecule can be designed such that, upon homologous recombination, the endogenous ABCB9 transporter gene is mutated or otherwise altered but still encodes functional protein (e.g., the upstream regulatory region can be altered to thereby alter the expression of the endogenous ABCB9 transporter protein). In the homologous recombination nucleic acid molecule, the altered portion of the ABCB9 transporter gene is flanked at its 5' and 3' ends by additional nucleic acid sequence of the ABCB9 transporter gene to allow for homologous recombination to occur between the exogenous ABCB9 transporter gene carried by the homologous recombination nucleic acid molecule and an endogenous ABCB9 transporter gene in a cell, e.g., an embryonic stem cell. The additional flanking ABCB9 transporter nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced ABCB9 transporter gene has homologously recombined with the endogenous ABCB9 transporter gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The ABCB9 transporter nucleic acid molecules, fragments of ABCB9 transporter proteins, anti-ABCB9 transporter antibodies (also referred to herein as "active compounds"), expressible nucleic acids encoding ABCB9 transporters (or fragments thereof), or any compound identified as a modulator of an ABCB9 transporter (as described herein) can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an ABCB9 transporter protein or an anti-ABCB9 transporter antibody) in the required amount in an appropriate solvent with one or a combination of ingredients enumerated above, as required, followed by filtered sterilization. Generally, dispersions are prepared by incorporating the active compound into a sterile vehicle which contains a basic ABCB9 transporter dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express ABCB9 transporter protein (e.g., via a recombinant expression vector in a host cell in gene therapy applications), to detect ABCB9 transporter mRNA (e.g., in a biological sample) or a genetic alteration in an ABCB9 transporter gene, and to modulate ABCB9 transporter activity, as described further below. The ABCB9 transporter proteins can be used to treat disorders characterized by insufficient or excessive production of an ABCB9 transporter substrate or production of ABCB9 transporter inhibitors. In addition, the ABCB9 transporter proteins can be used to screen for naturally occurring ABCB9 transporter substrates, to screen for drugs or compounds which modulate ABCB9 transporter activity, as well as to treat disorders characterized by insufficient or excessive production of ABCB9 transporter protein or production of ABCB9 transporter protein forms which have decreased, aberrant or unwanted activity compared to ABCB9 transporter wild type protein. Moreover, the anti-ABCB9 transporter antibodies of the invention can be used to detect and isolate ABCB9 transporter proteins, regulate the bioavailability of ABCB9 transporter proteins, and modulate ABCB9 transporter activity.

A. Screening Assays

The invention provides a method (also referred to herein as a "screening assay") for identifying modulators, i.e., candidate or test compounds or agents (e.g., peptides, peptidomimetics, small molecules or other drugs) which bind to ABCB9 transporter proteins, have a stimulatory or inhibitory effect on, for example, ABCB9 transporter expression or ABCB9 transporter activity, or have a stimulatory or inhibitory effect on, for example, the expression or activity of an ABCB9 transporter substrate.

In one embodiment, the invention provides assays for screening candidate or test compounds which are substrates of an ABCB9 transporter protein or polypeptide or biologically active portion thereof. In another embodiment, the invention provides assays for screening candidate or test compounds which bind to or modulate the activity of an ABCB9 transporter protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladnersupra.).

In one embodiment, an assay is a cell-based assay in which a cell which expresses an ABCB9 transporter protein or biologically active portion thereof is contacted with a test compound and the ability of the test compound to modulate ABCB9 transporter activity is determined. Determining the ability of the test compound to modulate ABCB9 transporter activity can be accomplished by monitoring, for example, cellular transport of organic anions, organic cations, cytotoxic anti-cancer drugs, intracellular calcium, potassium, phosphatidylcholine, sodium concentration, neuronal membrane depolarization, a neurotoxic polypeptide (e.g., β-amyloid), or the activity of an ABCB9 transporter-regulated transcription factor. The cell, for example, can be of mammalian origin, e.g., a neuronal cell. The ability of the test compound to modulate ABCB9 transporter binding to a substrate or to bind to ABCB9 transporter can also be determined. Determining the ability of the test compound to modulate ABCB9 transporter binding to a substrate can be accomplished, for example, by coupling the ABCB9 transporter substrate with a radioisotope or enzymatic label such that binding of the ABCB9 transporter substrate to ABCB9 transporter can be determined by detecting the labeled ABCB9 transporter substrate in a complex. Determining the ability of the test compound to bind ABCB9 transporter can be accomplished, for example, by coupling the compound with a radioisotope or enzymatic label such that binding of the compound to ABCB9 transporter can be determined by detecting the labeled ABCB9 transporter compound in a complex. For example, compounds (e.g., ABCB9 transporter substrates) can be labeled with $^{125}I$, $^{131}I$, $^{35}S$, $^{33}P$, $^{32}P$, or $^3H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

In one embodiment, suitable compounds include, but are not limited to, verapamil, desmethoxyverapamil, chloroquine, quinine, chinchonidine, primaquine, tamoxifen, dihydrocyclosporin, yohimbine, corynanthine, reserpine, physostigmine, acridine, acridine orange, quinacrine, trifluoroperazine chlorpromazine, propanolol, atropine, tryptamine, forskolin, 1,9-dideoxyforskolin, cyclosporin, (U.S. Pat. No. 4,117,118 (1978)), PSC-833 (cyclosporin D, 6-[(2S,4R,6E)-4-methyl-2-(methylamino)-3-oxo-6-octenoic acid]-(9CI) [U.S. Pat. No. 5,525,590] [ACS 121584-18-7], Keller et al., "SDZ PSC 833, a non-immunosuppressive cylcosporine: its potency in overcoming p-glycoprotein-mediated multidrug resistance of murine leukemia", *Int J Cancer* 50:593–597 (1992)), RU-486 (17β-hydroxy-11β-[4-dimethylaminophenyl]-17α prop-1-ynyl estra-4,9-dien-3 one), RU-49953 (17β-hydroxy-11β,17α-[4-dimethylaminophenyl]-17β prop-1-ynyl estra-4,9 dien-3 one), S9778 (6-{4-[2,2-di( )-ethylamino]-1-piperidinyl}-N, N', di-2-propenyl-1,3,5-triazine-2,4-diamine, bismethane sulfonate, [U.S. Pat. No. 5,225,411; EP 466586] [ACS #140945-01-3]; Dhainaut et al., "New triazine derivatives as potent modulators of multidrug resistance," *J Medicinal Chemistry* 35:2481–2496 (1992)), MS-209 (5-[3-[4-(2,2-diphenylacetyl)piperazin-1-yl]-2-hydroxypropoxy] quinoline sesquifumarate, [U.S. Pat. No. 5,405,843 (continuation of U.S. Pat. No. 5,112,817)], [ACS #158681-49-3], Sato et al., "Reversal of multidrug resistance by a novel quinoline derivative, MS-209, *Cancer Chemother Pharmacol* 35:271–277 (1995)), MS-073 (Fukazawa et al., European Patent Application 0363212 (1989)), FK-506 (Tanaka et al., M. Physicochemical properties of FK-506, a novel immunosuppressant isolated from *Streptomyces tsukubaensis*" *Transplantation Proceedings.* 19(5 Suppl 6): 11–6, (1987); Naito et al., "Reversal of multidrug resistance by an immunosuppressive agent FK-506," *Cancer Chemother & Pharmacol.* 29:195–200 (1992); Pourtier-Manzanedo et al., "FK-506 (fujimycin) reverses the multidrug resistance of tumor cells in vitro," *Anti-Cancer Drugs* 2:279–83 (1991); Epand & Epand, "The new potent immunosuppressant FK-506 reverses multidrug resistance in Chinese hamster ovary cells," *Anti-Cancer Drug Design* 6:189–93 (1991)), VX-710 (2-peperidinecarboxylic acid, 1-[oxo(3,4,5-trimethoxyphenyl)acetyl]-3-(3-pyridinyl)-1-[3-(3-pyridinyl)propyl]butyl ester [ACS 159997-94-1] [U.S. Pat. No. 5,620,971] Germann et al., "Chemosensitization and drug accumulation effects of VX-710, verapamil, cyclosporin A, MS-209 and GF120918 in multidrug resistance-associated protein MRP" *Anti-Cancer Drugs* 8, 141–155 (1997); Germann et al., "Cellular and biochemical characterization of VX-710 as a chemosensitizer: reversal of P-glycoprotein-mediated multidrug resistance in vitro" *Anti-Cancer Drugs* 8, 125–140 (1997)), VX-853 ([U.S. Pat. No. 5,543,423] [ACS #190454-58-1), AHC-52 (methyl 2-(N-benzyl-N-methylamino)ethyl-2,6-dimethyl-4-(2-isopropylpyrazolo[1,5-a]pyridine-3-yl)-1,4-dihyropyridine-3,5-dicarboxylate; [Japanese Patent 63-135381; European Patent 0270926] [ACS 119666-09-0] Shinoda et al., "In vivo circumvention of vincristine resistance in mice with P388 leukemia using a novel compound, AHC-52," *Cancer Res* 49:1722–6 (1989)), GF-120918 (9,10-dihydro-5-methoxy-9-oxo-N-[4-[2-(1,2,3,4-tetrahydro-6,7-dimethoxyisoquinol-2-yl) ethyl]phenyl]-4 acridinecarboxamide, [U.S. Pat. No. 5,604,237] [ACS #143664-11-3] et al., "In vitro and in vivo reversal of multidrug resistance by GF 120918, an acridonecarboxamide derivative," *Cancer Res* 53:4595–4602 (1993)), and XR-9051 (3-[(3Z,6Z)-6-Benzylidene-1-methyl-2,5-dioxopiperazin-3-ylidenemethyl]-N-[4-[2-(6,7-dimethoxy-1,2,3,4-tetrahydroisoquinolin-2-yl)ethyl]phenyl] benzamide hydrochloride, [ACS #57-22-7]).

It is also within the scope of this invention to determine the ability of a compound (e.g., an ABCB9 transporter substrate) to interact with ABCB9 transporter without the labeling of any of the interactants. For example, a microphysiometer can be used to detect the interaction of a compound with ABCB9 transporter without the labeling of either the compound or the ABCB9. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and ABCB9.

In another embodiment, an assay is a cell-based assay comprising contacting a cell expressing an ABCB9 transporter target molecule (e.g., an ABCB9 transporter substrate) with a test compound and determining the ability of the test compound to modulate (e.g. stimulate or inhibit) the activity of the ABCB9 transporter target molecule. Determining the ability of the test compound to modulate the activity of an ABCB9 transporter target molecule can be accomplished, for example, by determining the ability of the ABCB9 transporter protein to bind to or interact with the ABCB9 transporter target molecule.

Determining the ability of the ABCB9 transporter protein or a biologically active fragment thereof, to bind to or interact with an ABCB9 transporter target molecule can be accomplished by one of the methods described above for determining direct binding. In a preferred embodiment, determining the ability of the ABCB9 transporter protein to bind to or interact with an ABCB9 transporter target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), cellular transport of, e.g., a reference compound or, e.g., a neurotoxic polypeptide (e.g., β-amyloid) or detecting a target-regulated cellular response.

In yet another embodiment, an assay of the present invention is a cell-free assay in which an ABCB9 transporter protein or biologically active portion thereof is contacted with a test compound and the ability of the test compound to bind to the ABCB9 transporter protein or biologically active portion thereof is determined. Preferred biologically active portions of the ABCB9 transporter proteins to be used in assays of the present invention include fragments which participate in interactions with non-ABCB9 transporter molecules, e.g., fragments with high surface probability scores (see, for example, FIG. 2). Binding of the test compound to the ABCB9 transporter protein can be determined either directly or indirectly as described above. In a preferred embodiment, the assay includes contacting the ABCB9 transporter protein or biologically active portion thereof with a known compound which binds ABCB9 transporter to form an assay mixture, contacting the assay mixture with a test compound, and determining the ability of the test compound to interact with an ABCB9 transporter protein, wherein determining the ability of the test compound to interact with an ABCB9 transporter protein comprises determining the ability of the test compound to preferentially bind to ABCB9 transporter or biologically active portion thereof as compared to the known compound.

In another embodiment, the assay is a cell-free assay in which an ABCB9 transporter protein or biologically active portion thereof is contacted with a test compound and the ability of the test compound to modulate (e.g., stimulate or inhibit) the activity of the ABCB9 transporter protein or biologically active portion thereof is determined. Determining the ability of the test compound to modulate the activity of an ABCB9 transporter protein can be accomplished, for example, by determining the ability of the ABCB9 transporter protein to bind to an ABCB9 transporter target molecule by one of the methods described above for determining direct binding. Alternatively, for example, ATP binding can be measured. Determining the ability of the ABCB9 transporter protein to bind to an ABCB9 transporter target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of an ABCB9 transporter protein can be accomplished by determining the ability of the ABCB9 transporter protein to further modulate the activity of a downstream effector of an ABCB9 transporter target molecule. For example, the activity of the effector molecule on an appropriate target can be determined or the binding of the effector to an appropriate target can be determined as previously described.

In yet another embodiment, the cell-free assay involves contacting an ABCB9 transporter protein or biologically active portion thereof with a known compound which binds the ABCB9 transporter protein to form an assay mixture, contacting the assay mixture with a test compound, and determining the ability of the test compound to interact with the ABCB9 transporter protein, wherein determining the ability of the test compound to interact with the ABCB9 transporter protein comprises determining the ability of the ABCB9 transporter protein to preferentially bind to or modulate the activity of an ABCB9 transporter target molecule.

The cell-free assays of the present invention are amenable to use of both soluble and/or membrane-bound forms of isolated proteins (e.g., ABCB9 transporter proteins or biologically active portions thereof). In the case of cell-free assays in which a membrane-bound form of an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N, N-dimethyl-3-ammonio-1-propane sulfonate.

In more than one embodiment of the above assay methods of the present invention, it may be desirable to immobilize either ABCB9 transporter or its target molecule to facilitate separation of complexed from uncomplexed forms of one or both of the proteins, as well as to accommodate automation of the assay. Binding of a test compound to an ABCB9 transporter protein, or interaction of an ABCB9 transporter protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/ABCB9 transporter fusion proteins or glutathione-S-transferase/target fusion proteins can be adsorbed onto glutathione Sepharose beads (Sigma Chemical, St. Louis, Mo.) or glutathione derivatized microtitre plates, which are then combined with the test compound or the test compound and either the non-adsorbed target protein or ABCB9 transporter protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of ABCB9 transporter binding or activity determined using standard techniques.

Other techniques for immobilizing proteins on matrices can also be used in the screening assays of the invention. For example, either an ABCB9 transporter protein or an ABCB9 transporter target molecule can be immobilized utilizing conjugation of biotin and streptavidin. Biotinylated ABCB9 transporter protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with ABCB9 transporter protein or target molecules but which do not interfere with binding of the ABCB9 transporter protein to its target molecule can be derivatized to the wells of the plate, and unbound target or ABCB9 transporter protein trapped in the wells by antibody conjugation. Methods for detecting such complexes, in addition to those described above for the GST-immobilized complexes, include immunodetection of complexes using antibodies reactive with the ABCB9 transporter protein or target molecule, as well as enzyme-linked assays which rely on detecting an enzymatic activity associated with the ABCB9 transporter protein or target molecule.

In another embodiment, modulators of ABCB9 transporter expression are identified in a method wherein a cell is contacted with a candidate compound and the expression of ABCB9 transporter mRNA or protein in the cell is determined. The level of expression of ABCB9 transporter mRNA or protein in the presence of the candidate compound is compared to the level of expression of ABCB9 transporter mRNA or protein in the absence of the candidate compound. The candidate compound can then be identified as a modulator of ABCB9 transporter expression based on this comparison. For example, when expression of ABCB9 transporter mRNA or protein is greater (statistically significantly greater) in the presence of the candidate compound than in its absence, the candidate compound is identified as a stimulator of ABCB9 transporter mRNA or protein expression. Alternatively, when expression of ABCB9 transporter mRNA or protein is less (statistically significantly less) in the presence of the candidate compound than in its absence, the candidate compound is identified as an inhibitor of ABCB9 transporter mRNA or protein expression. The level of ABCB9 transporter mRNA or protein expression in the cells can be determined by methods described herein for detecting ABCB9 transporter mRNA or protein.

In yet another aspect of the invention, the ABCB9 transporter proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with ABCB9 transporter ("ABCB9-binding proteins" or "ABCB9-bp") and are involved in ABCB9 transporter activity. Such ABCB9-binding proteins are also likely to be involved in the propagation of signals by the ABCB9 transporter proteins or ABCB9 transporter targets as, for example, downstream elements of an ABCB9-mediated signaling pathway. Alternatively, such ABCB9-binding proteins are likely to be ABCB9 transporter inhibitors.

The two-hybrid system is based on the modular nature of most transcription factors, which consist of separable DNA-binding and activation domains. Briefly, the assay utilizes two different DNA constructs. In one construct, the gene that codes for an ABCB9 transporter protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an ABCB9-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the ABCB9 transporter protein.

In another aspect, the invention pertains to a combination of two or more of the assays described herein. For example, a modulating agent can be identified using a cell-based or a cell free assay, and the ability of the agent to modulate the activity of an ABCB9 transporter protein can be confirmed in vivo, e.g., in an animal.

This invention further pertains to novel agents identified by the above-described screening assays. Accordingly, it is within the scope of this invention to further use an agent identified as described herein in an appropriate animal model. For example, an agent identified as described herein (e.g., an ABCB9 transporter modulating agent, an antisense ABCB9 transporter nucleic acid molecule, an ABCB9-specific antibody, or an ABCB9-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the ABCB9 transporter nucleotide sequences, described herein, can be used to map the location of the ABCB9, transporter genes on a chromosome. The mapping of the ABCB9 transporter sequences to chromosomes is an important first step in correlating these sequences with genes associated with disease.

Briefly, ABCB9 transporter genes can be mapped to chromosomes by preparing PCR primers (preferably 15–25 bp in length) from the ABCB9 transporter nucleotide sequences. Computer analysis of the ABCB9 transporter sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the ABCB9 transporter sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the ABCB9 transporter nucleotide sequences to design oligonucleotide primers, sublocalization can be achieved with panels of fragments from specific chromosomes. Other mapping strategies which can similarly be used to map an ABCB9 transporter sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of BABC transporter Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the ABCB9 transporter gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The ABCB9 transporter sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the ABCB9 transporter nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The ABCB9 transporter nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO: 1 can comfortably provide positive individual identification with a panel of perhaps 10 to 1,000 primers which each yield a noncoding amplified sequence of 100 bases. If predicted coding sequences, such as those in SEQ ID NO: 3 are used, a more appropriate number of primers for positive individual identification would be 500–2,000.

If a panel of reagents from ABCB9 transporter nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of ABCB9 Transporter Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO: 1 are particularly appropriate for this use as greater numbers of polymorphisms occur in the noncoding regions, making it easier to differentiate individuals using this technique. Examples of polynucleotide reagents include the ABCB9 transporter nucleotide sequences or portions thereof, e.g., fragments derived from the noncoding regions of SEQ ID NO: 1 having a length of at least 20 bases, preferably at least 30 bases.

The ABCB9 transporter nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such ABCB9 transporter probes can be used to identify tissue by species and/or by organ type.

In a similar fashion, these reagents, e.g., ABCB9 transporter primers or probes can be used to screen tissue culture for contamination (i.e. screen for the presence of a mixture of different types of cells in a culture).

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining ABCB9 transporter protein and/or nucleic acid expression as well as ABCB9 transporter activity, in the context of a biological sample (e.g., blood, serum, cells, tissue) to thereby determine whether an individual is afflicted with a disease or disorder, or is at risk of developing a disorder, associated with aberrant or unwanted ABCB9 transporter expression or activity. The invention also provides for prognostic (or predictive) assays for determining whether an individual is at risk of developing a disorder associated with ABCB9 transporter protein, nucleic acid expression or activity. For example, mutations in an ABCB9 transporter gene can be assayed in a biological sample. Such assays can be used for prognostic or predictive purpose to thereby prophylactically treat an individual prior to the onset of a disorder characterized by or associated with ABCB9 transporter protein, nucleic acid expression or activity.

Another aspect of the invention pertains to monitoring the influence of agents (e.g., drugs, compounds) on the expression or activity of ABCB9 transporter in clinical trials.

These and other agents are described in further detail in the following sections.

1. Diagnostic Assays

An exemplary method for detecting the presence or absence of ABCB9 transporter protein or nucleic acid in a biological sample involves obtaining a biological sample from a test subject and contacting the biological sample with a compound or an agent capable of detecting ABCB9 transporter protein or nucleic acid (e.g., mRNA, genomic DNA) that encodes ABCB9 transporter protein such that the presence of ABCB9 transporter protein or nucleic acid is detected in the biological sample. A preferred agent for detecting ABCB9 transporter mRNA or genomic DNA is a labeled nucleic acid probe capable of hybridizing to ABCB9 transporter mRNA or genomic DNA. The nucleic acid probe can be, for example, a full-length ABCB9 transporter nucleic acid, such as the nucleic acid of SEQ ID NO: 1, or a portion thereof, such as an oligonucleotide of at least 15, 30, 50, 100, 250 or 500 nucleotides in length and sufficient to specifically hybridize under stringent conditions to ABCB9 transporter mRNA or genomic DNA. Other suitable probes for use in the diagnostic assays of the invention are described herein.

A preferred agent for detecting ABCB9 transporter protein is an antibody capable of binding to ABCB9 transporter protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect ABCB9 transporter mRNA, protein, or genomic DNA in a biological sample in vitro as well as in vivo. For example, in vitro techniques for detection of ABCB9 transporter mRNA include Northern hybridizations and in situ hybridizations. In vitro techniques for detection of ABCB9 transporter protein include enzyme linked immunosorbent assays (ELISAs), Western blots, immunoprecipitations and immunofluorescence. In vitro techniques for detection of ABCB9 transporter genomic DNA include Southern hybridizations. Furthermore, in vivo techniques for detection of ABCB9 transporter protein include introducing into a subject a labeled anti-ABCB9 transporter antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting ABCB9 transporter protein, mRNA, or genomic DNA, such that the presence of ABCB9 transporter protein, mRNA or genomic DNA is detected in the biological sample, and comparing the presence of ABCB9 transporter protein, mRNA or genomic DNA in the control sample with the presence of ABCB9 transporter protein, mRNA or genomic DNA in the test sample.

The invention also encompasses kits for detecting the presence of ABCB9 transporter in a biological sample. For example, the kit can comprise a labeled compound or agent capable of detecting ABCB9 transporter protein or mRNA in a biological sample; means for determining the amount of ABCB9 transporter in the sample; and means for comparing the amount of ABCB9 transporter in the sample with a standard. The compound or agent can be packaged in a suitable container. The kit can further comprise instructions for using the kit to detect an ABCB9 transporter protein or nucleic acid.

2. Prognostic Assays

The diagnostic methods described herein can furthermore be utilized to identify subjects having or at risk of developing a disease or disorder associated with aberrant or unwanted ABCB9 transporter expression or activity. As used herein, the term "aberrant" includes an ABCB9 transporter expression or activity which deviates from the wild type ABCB9 transporter expression or activity. Aberrant expression or activity includes increased or decreased expression or activity, as well as expression or activity which does not follow the wild type developmental pattern of expression or the subcellular pattern of expression. For example, aberrant ABCB9 transporter expression or activity is intended to include the cases in which a mutation in the ABCB9 transporter gene causes the ABCB9 transporter gene to be under-expressed or over-expressed and situations in which such mutations result in a non-functional ABCB9 transporter protein or a protein which does not function in a wild-type fashion, e.g., a protein which does not interact with an ABCB9 transporter ligand or one which interacts with a non-ABCB9 transporter ligand. As used herein, the term "unwanted" includes an unwanted phenomenon involved in a biological response. For example, the term unwanted includes an ABCB9 transporter expression or activity which is undesirable in a subject.

The assays described herein, such as the preceding diagnostic assays or the following assays, can be utilized to identify a subject having or at risk of developing a disorder associated with a misregulation in ABCB9 transporter protein activity or nucleic acid expression. Alternatively, the prognostic assays can be utilized to identify a subject having or at risk for developing a disorder associated with a misregulation in ABCB9 transporter protein activity or nucleic acid expression. Thus, the present invention provides a method for identifying a disease or disorder associated with aberrant or unwanted ABCB9 transporter expression or activity in which a test sample is obtained from a subject and ABCB9 transporter protein or nucleic acid (e.g., mRNA or genomic DNA) is detected, wherein the presence of ABCB9 transporter protein or nucleic acid is diagnostic for a subject having or at risk of developing a disease or disorder associated with aberrant or unwanted ABCB9 transporter expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted ABCB9 transporter expression or activity, e.g., a cancer where the cells of the cancer have developed multidrug resistance. Thus, the present invention provides methods for determining whether a subject can be effectively treated with an agent for a disorder associated with aberrant or unwanted ABCB9 transporter expression or activity in which a test sample is obtained and ABCB9 transporter protein or nucleic acid expression or activity is detected (e.g., wherein the abundance of ABCB9 transporter protein or nucleic acid expression or activity is diagnostic for a subject that can be administered the agent to treat a disorder associated with aberrant or unwanted ABCB9 transporter expression or activity).

The methods of the invention can also be used to detect genetic alterations in an ABCB9 transporter gene, thereby determining if a subject with the altered gene is at risk for a disorder characterized by misregulation in ABCB9 transporter protein activity or nucleic acid expression. In preferred embodiments, the methods include detecting, in a sample of cells from the subject, the presence or absence of a genetic alteration characterized by at least one of an alteration affecting the integrity of a gene encoding an ABCB9 protein, or the mis-expression of the ABCB9 transporter gene. For example, such genetic alterations can be detected by ascertaining the existence of at least one of 1) a deletion of one or more nucleotides from an ABCB9 transporter gene; 2) an addition of one or more nucleotides to an ABCB9 transporter gene; 3) a substitution of one or more nucleotides of an ABCB9 transporter gene, 4) a chromosomal rearrangement of an ABCB9 transporter gene; 5) an alteration in the level of a messenger RNA transcript of an ABCB9 transporter gene, 6) aberrant modification of an ABCB9 transporter gene, such as of the methylation pattern of the genomic DNA, 7) the presence of a non-wild type splicing pattern of a messenger RNA transcript of an ABCB9 transporter gene, 8) a non-wild type level of an ABCB9-protein, 9) allelic loss of an ABCB9 transporter gene, and 10) inappropriate post-translational modification of an ABCB9-protein. As described herein, there are a large number of assays known in the art which can be used for detecting alterations in an ABCB9 transporter gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91 :360–364), the latter of which can be particularly useful for detecting point mutations in the ABCB9-gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an ABCB9 transporter gene under conditions such that hybridization and amplification of the ABCB9-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad Sci. USA* 87:1874–1878), transcriptional amplification system (Kwoh, D. Y. et al., (1989) *Proc. Natl. Acad Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an ABCB9 transporter gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in ABCB9 transporter can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in ABCB9 transporter can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the ABCB9 transporter gene and detect mutations by comparing the sequence of the sample ABCB9 transporter with the corresponding wild-type (control) sequence. Examples of sequencing reactions include those based on techniques developed by Maxam and Gilbert ((1977) *Proc. Natl. Acad Sci. USA* 74:560) or Sanger ((1977) *Proc. Natl. Acad Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the ABCB9 transporter gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type ABCB9 transporter sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Nail Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in ABCB9 transporter cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an ABCB9 transporter sequence, e.g., a wild-type ABCB9 transporter sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in ABCB9 transporter genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144;

and Hayashi (1992) *Genet. Anal. Tech. Appl.* 9:73–79). Single-stranded DNA fragments of sample and control ABCB9 transporter nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an ABCB9 transporter gene.

Furthermore, any cell type or tissue in which ABCB9 transporter is expressed may be utilized in the prognostic assays described herein.

3. Monitoring of Effects During Clinical Trials

Monitoring the influence of agents (e.g., drugs) on the expression or activity of an ABCB9 transporter protein can be applied not only in ABCB9 transporter drug screening, but also in clinical trials. For example, the effectiveness of an agent determined by a screening assay as described herein to increase ABCB9 transporter gene expression, protein levels, or upregulate ABCB9 transporter activity, can be monitored in clinical trials of subjects exhibiting decreased ABCB9 transporter gene expression, protein levels, or downregulated ABCB9 transporter activity. Alternatively, the effectiveness of an agent determined by a screening assay to decrease ABCB9 transporter gene expression, protein levels, or downregulate ABCB9 transporter activity, can be monitored in clinical trials of subjects exhibiting increased ABCB9 transporter gene expression, protein levels, or upregulated ABCB9 transporter activity. In such clinical trials, the expression or activity of an ABCB9 transporter gene, and preferably, other genes that have been implicated in, for example, an ABCB9-associated disorder can be used as a "read out" or markers of the phenotype of a particular cell.

For example, and not by way of limitation, genes, including ABCB9, that are modulated in cells by treatment with an agent (e.g., compound, drug or small molecule) which modulates ABCB9 transporter activity (e.g., identified in a screening assay as described herein) can be identified. Thus, to study the effect of agents on ABCB9-associated disorders, for example, in a clinical trial, cells can be isolated and RNA prepared and analyzed for the levels of expression of ABCB9 transporter and other genes implicated in the ABCB9-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of ABCB9 transporter or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an ABCB9 transporter protein, mRNA, or genomic DNA in the preadministration sample; (iii) obtaining one or more post-administration samples from the subject; (iv) detecting the level of expression or activity of the ABCB9 transporter protein, mRNA, or genomic DNA in the post-administration samples; (v) comparing the level of expression or activity of the ABCB9 transporter protein, mRNA, or genomic DNA in the pre-administration sample with the ABCB9 transporter protein, mRNA, or genomic DNA in the post administration sample or samples; and (vi) altering the administration of the agent to the subject accordingly. For example, increased administration of the agent may be desirable to increase the expression or activity of ABCB9 transporter to higher levels than detected, i.e., to increase the effectiveness of the agent.

Alternatively, decreased administration of the agent may be desirable to decrease expression or activity of ABCB9 transporter to lower levels than detected, i.e. to decrease the effectiveness of the agent. According to such an embodiment, ABCB9 transporter expression or activity may be used as an indicator of the effectiveness of an agent, even in the absence of an observable phenotypic response.

D. Methods of Treatment

The present invention provides for both prophylactic and therapeutic methods of treating a subject at risk of (or susceptible to) a disorder or having a disorder associated with aberrant or unwanted ABCB9 transporter expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the ABCB9 transporter molecules of the present invention or ABCB9 transporter modulators according to that individual's drug response genotype. Pharmacogenomics allows a clinician or physician to is target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted ABCB9 transporter expression or activity, by administering to the subject an ABCB9 transporter or an agent which modulates ABCB9 transporter expression or at least one ABCB9 transporter activity. Subjects at risk for a disease which is caused or contributed to by aberrant or unwanted ABCB9 transporter expression or activity can be identified by, for example, any or a combination of diagnostic or prognostic assays as described herein. Administration of a prophylactic agent can occur prior to the manifestation of symptoms characteristic of the ABCB9 transporter aberrancy, such that a disease or disorder is prevented or, alternatively, delayed in its progression. Depending on the type of ABCB9 transporter aberrancy, for example, an ABCB9, ABCB9 transporter agonist or ABCB9 transporter antagonist agent can be used for treating the subject. The appropriate agent can be determined based on screening assays described herein.

2. Therapeutic Methods

Another aspect of the invention pertains to methods of modulating ABCB9 transporter expression or activity for therapeutic purposes. Accordingly, in an exemplary embodiment, the modulatory method of the invention involves contacting a cell with an ABCB9 transporter or agent that modulates one or more of the activities of ABCB9 transporter protein activity associated with the cell. An agent that modulates ABCB9 transporter protein activity can be an agent as described herein, such as a nucleic acid or a protein, a naturally-occurring target molecule of an ABCB9 transporter protein (e.g., an ABCB9 transporter substrate), an ABCB9 transporter antibody, an ABCB9 transporter agonist or antagonist, a peptidomimetic of an ABCB9 transporter agonist or antagonist, or other small molecule. In one embodiment, the agent stimulates one or more ABCB9 transporter activities. Examples of such stimulatory agents include active ABCB9 transporter protein and a nucleic acid molecule encoding an ABCB9 transporter that has been introduced into the cell. In another embodiment, the agent inhibits one or more ABCB9 transporter activities. Examples of such inhibitory agents include antisense ABCB9 transporter nucleic acid molecules, anti-ABCB9 transporter antibodies, and ABCB9 transporter inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of an ABCB9 transporter protein or nucleic acid molecule. In one embodiment, the method involves administering an agent (e.g., an agent identified by a screening assay described herein), or combination of agents that modulates (e.g., upregulates or downregulates) ABCB9 transporter expression or activity. In another embodiment, the method involves administering an ABCB9 transporter protein or nucleic acid molecule as therapy to compensate for reduced, aberrant, or unwanted ABCB9 transporter expression or activity.

Stimulation of ABCB9 transporter activity is desirable in situations in which ABCB9 transporter is abnormally downregulated and/or in which increased ABCB9 transporter activity is likely to have a beneficial effect. For example, stimulation of ABCB9 transporter activity is desirable in situations in which an ABCB9 transporter is downregulated and/or in which increased ABCB9 transporter activity is likely to have a beneficial effect. Likewise, inhibition of ABCB9 transporter activity is desirable in situations in which ABCB9 transporter is abnormally upregulated and/or in which decreased ABCB9 transporter activity is likely to have a beneficial effect.

In one embodiment, an agent found to inhibit ABCB9 transporter activity is used in combination with another therapy such that the targeting of that therapy across the blood-brain-barrier is achieved.

3. Pharmacogenomics

The ABCB9 transporter molecules of the present invention, as well as agents, or modulators which have a stimulatory or inhibitory effect on ABCB9 transporter activity (e.g., ABCB9 transporter gene expression) as identified by a screening assay described herein can be administered to individuals to treat (prophylactically or therapeutically) ABCB9-associated disorders associated with aberrant or unwanted ABCB9 transporter activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an ABCB9 transporter molecule or ABCB9 transporter modulator as well as tailoring the dosage and/or therapeutic regimen of treatment with an ABCB9 transporter molecule or ABCB9 transporter modulator.

Pharmacogenomics deals with clinically significant hereditary variations in the response to drugs due to altered drug disposition and abnormal action in affected persons. See, for example, Eichelbaum, M. et al (1996) *Clin. Exp. Pharmacol. Physiol* 23(10–11):983–985 and Linder, M. W.

et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP", is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., an ABCB9 transporter protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an ABCB9 transporter molecule or ABCB9 transporter modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an ABCB9 transporter molecule or ABCB9 transporter modulator, such as a modulator identified by one of the exemplary screening assays described herein.

This invention is further illustrated by the following examples which should not be construed as limiting.

EXEMPLIFICATION

Example 1

ISOLATION AND CLONING OF THE HUMAN ABCB9 TRANSPORTER cDNA

In this example, the isolation and cloning of the gene encoding a novel human ABCB9 (transporter (i.e., human ABCB9) is described.

The human ABCB9 transporter (i.e. ABCB9) was first identified as an expressed sequence tag (EST) partial clone by performing a data base search using the default parameters of the program TBLASTN (Altschul et al., 1990; Altschul et al. 1994) against the non-redundant Database of GenBank EST Division (The National Center for Biotechnology Information, Bethesda, Md.). Partial protein sequences from Chinese hamster pgp1 (Gerlach et al., 1986) and E. coli HlyB (Felmlee et al., 1985), that contain the signature ATP-binding motifs present in the ATP-binding cassette (ABC) superfamily, were used to identify two independent clones in the data base. The 234 bp EST122234 (GenBank accession number F06569; (SEQ ID NO: 16)) and EST195763 (GenBank accession number R25718; (SEQ ID NO: 17)) were subsequently received upon request from the Programme Genexpress division of the Laboratoire Genethon (1, rue de l'Internationale, BP 60-91002 EVRY Cedex, France) and Washington University-Merck EST project (St. Louis, Mo.). The nucleotide sequence was confirmed by DNA sequence analysis. DNA sequencing was performed using the Sanger dideoxy-mediated chain-termination method using plasmid specific oligonucleotide primers (Sequenase Version 1.0 DNA sequencing KIT, U.S. Biochemicals, No. 70700) and a sequencing gel apparatus (BRL model S2).

The full-length coding sequence for ABCB9 was obtained from a human acute lymphoblastic leukemia cDNA library. The recombinant cDNA library was constructed using standard molecular biology techniques and commercially available reagents and kits (Sambrook et al. *Molecular Cloning: A Laboratory Manual*. 2nd ed., Cold Spring Harbor Laboratory Press, Cold Spring Harbor, N.Y., 1989). Total cellular RNA was isolated from $10^8$ T lymphoblastoid CCRF-CEM cells (ATCC CCL 119; Foley et al. Cancer (1965) 18:522–529) by the acid guanidinium thiocyanate-phenol-chloroform extraction method (Chomczynski and Sacchi *Anal. Biochem.* (1987) 162:156–159). Poly (A$^+$) RNA was purified from total cellular RNA by affinity chromatography on oligo(dT)-cellulose, type 3 (Collaborative biomedical Products No20003.). The SuperScript™ Choice System for cDNA Synthesis (Gibco BRL No. 18909-019) was used to convert approximately 9 ug of purified Poly(A+) mRNA template in the presence oligo(dT) primers into double-stranded cDNA. Synthetic EcoRI (NotI) adaptors were ligated to the double-stranded cDNA and subsequently phosphorylated according to the manufacturer's specifications. After size fractionation and the removal of excess adaptors on a size selection column, 47 ng of cDNA was ligated into Lambda ZAP" II EcoRI digested and dephosphorylated vector arms (Stratagene No. 236211). The cDNA was assembled into mature bacteriophage particles using the Gigapack" III Gold-11 Packaging Extract (Stratagene No. 200203). The partial EST clone 122234 was labeled in the presence of $^{32}$P-dCTP by the primer extension method and used to probe the T lymphoblastoid cell CCRF-CEM Lambda ZAP II cDNA library (see above) (Sambrook et al. *Molecular Cloning: A Laboratory Manual*. 2nd ed., Cold Spring Harbor Laboratory Press, Cold Spring Harbor, N.Y., 1989). Initial high-stringency screening (5×SSPE, 5×Denhart's 0.5% SDS at 65° C. for 16 hr; followed by two washes with 2×SSPE, 0.1% SDS for 15 min at 23° C.; 2×SSC, two washes at 0.1% SDS for 30 min at 50° C.; and a single wash with 0.2×SSC, 0.1 % SDS for 30 min at 65° C.) yielded 2 recombinant clones that were able to hybridize the $^{32}$P-labeled EST 122234 probe. A single positive phage clone was enriched, isolated, and subsequently converted in vivo to a Bluescript plasmid from the lambda phage vector using the ExAssist™ Interference-Resistant Helper Phage (Stratagene No. 200253). The 3537 bp cDNA clone, designated c1-2, was selected for sequence analysis. DNA sequencing was performed on both the sense and anti-sense strands of the plasmid DNA using the Sanger dideoxy-mediated chain-termination method (Sequenase Version 1.0 DNA sequencing KIT, U.S. Biochemicals, Cat 70700) and a BRL sequencing gel apparatus (BRL model S2). A directed sequencing approach using specific oligonucleotide primers (Gibco BRL Custom Primers) and moving the priming site along the length of the cDNA at 300 bp intervals was used to obtain the complete sequence. The Wisconsin Genetics Computer Group (GCG) sequence analysis software package Version 8.0 was used to compile the sequencing results.

An additional 44 bp 5' fragment of ABCB9 was obtained by the rapid amplification of cDNA ends polymerase chain reaction cloning method (RACE-PCR) using a pool of adaptor-ligated double-stranded (ds) cDNAs that were synthesized from 1 µg of purified Poly(A+) mRNA derived from CCRE-CEM cells (MARATHON cDNA Amplification kit, CLONTECH No. K1802-1). In the first PCR amplification, the paired combination of adaptor-specific forward primer AP1 (CLONTECH) and gene-specific reverse primer E1-12b (5'-GGATGGGCCTGCGCA-CCTCT; (SEQ ID NO: 18); Gibco BRL Custom Primers) was added to the CCRE-CEM AP1/AP2 adaptor-ligated dscDNA pool. An enLONGase DNA polymerase enzyme mix (BRL No. 10480) and the Perkin-Elmer 2400 thermal cycler was used to perform 30 reaction cycles (denaturation at 94° C. for 1 min; denaturation at 94° C. for 20 sec; annealing at 68° C. for 2 min). The second 'nested' PCR amplification step was initiated in a reaction mixture containing 2.5 µl of a 1/50 dilution of the first PCR amplification reaction in the presence of the adaptor-specific forward primer AP2 (CLONTECH) and gene-specific reverse primer E1-7b (5' CACTCATGAAGGCCAAAG; (SEQ ID NO: 19); Gibco BRL Custom Primers). Twenty-five reaction cycles (denaturation at 94° C. for 1 min; denaturation at 94° C. for 20 sec; annealing at 55° C. for 30 sec; elongation at 72° C. for 30 sec) were performed in the presence of enLONGase enzyme mix DNA polymerase (BRL No. 10480). The 3' T overhang found in the enLONGase Taq polymerase amplified PCR products was used to clone the new ABCB9 5'-RACE-PCR fragments into pCR2.1 vector following the instructions outlined in the Original TA Cloning® Kit (Invitrogen No. K2030-J10). The 344 bp RACE-PCR product was sequenced by the Sanger dideoxy-mediated chain-termination method according to the manufacturer's specifications (Sequenase Version 1.0 DNA sequencing KIT, U.S. Biochemicals, Cat 70700).

The complete ABCB9 transporter sequence was derived from both cDNA clones to yield a contiguous 3536 bp fragment excluding the poly (A$^+$) region. The nucleotide sequence of the ABCB9 cDNA is shown in FIG. 1 (SEQ ID NO: 1). ABCB9 was predicted to encode a single 2298 bp open reading frame beginning with the initiating AUG at nucleotide position 299 and terminating with the stop UGA at nucleotide position 2597. Several in-frame termination codons were observed in all three reading frames of the 298 bp 5' untranslated region (UTR), thereby establishing the AUG codon located at position 299 as the translational start site. The 916 bp 3' UTR contained a polyadenylation signal (AATAAA; (SEQ ID NO: 20)) that preceded the poly (A$^+$) tail by 20 nucleotides. The expected molecular mass of the 766 amino-acid-residue polypeptide encoded by the human ABCB9 cDNA is 117.2 kDa. The complete amino acid sequence of the full-length human ABCB9 protein is shown in FIG. 2 (SEQ ID NO: 2).

Example 2

CHARACTERIZATION OF THE NOVEL HUMAN ABCB9 TRANSPORTER MOLECULES

In this example, the amino acid sequences of the human ABCB9 transporter polypeptide was compared to amino acid sequences of known polypeptides and various motifs were identified.

In particular, by comparing the nucleic acid sequence (and predicted amino acid sequence) of the isolated clone to other sequences found in publicly available databases (e.g., GenBank). Comparison of the predicted 766 amino acid sequence of the 2298 bp open reading frame of the isolated human ABCB9 gene reveals a significant homology with other related proteins, including rat TAPL, human ABCB2, mouse TAP1, rat TAP1, human ABCB3, mTAP2 and rat TAP2 (Table 1.).

TABLE 1

Homology between ABCB9 and related amino acid sequences expressed as a percentage of amino acid similarity/identity.

|       | ABCB9   | rTAPL   | ABCB2   | mTAP1   | rTAP1   | ABCB3   | mTAP2   | rTAP2   |
|-------|---------|---------|---------|---------|---------|---------|---------|---------|
| ABCB9 | 100/100 | 95/93   | 55/34   | 54/33   | 54/34   | 53/36   | 55/36   | 55/36   |
| rTAPL |         | 100/100 | 55/34   | 55/34   | 55/35   | 52/34   | 55/36   | 55/36   |
| ABCB2 |         |         | 100/100 | 80/69   | 81/69   | 51/34   | 53/35   | 53/34   |
| mTAP1 |         |         |         | 100/100 | 92/88   | 54/35   | 54/36   | 55/36   |
| rTAP1 |         |         |         |         | 100/100 | 53/35   | 53/36   | 54/36   |
| ABCB3 |         |         |         |         |         | 100/100 | 84/74   | 82/73   |
| mTAP2 |         |         |         |         |         |         | 100/100 | 94/91   |
| rTAP2 |         |         |         |         |         |         |         | 100/100 |

An amino acid sequence alignment between the predicted human ABCB9 and these related proteins is shown in FIGS. 3-1, 3-2, and 3-3.

The human ABCB9 transporter polypeptide was also analyzed for known domain motifs which indicate membership in the superfamily of ABC transporters. The Walker A and Walker B motifs (Patel et al. (1998) *Trends Cell Biol* 8: 65–71) are readily apparent in the amino acid sequence, as well as the "ABC Transporter Signature Sequence."

The relation of ABCB9 to some of the other human ABC proteins can be seen in the cladistic representation of the ABC superfamily in FIG. 4.

Example 3

TISSUE DISTRIBUTION OF HUMAN ABCB9 TRANSPORTER mRNA

This example describes the tissue distribution of ABCB9 transporter mRNA, as can be determined by Northern blot hybridization and in situ hybridization.

Northern blot hybridizations with the various RNA samples are performed under standard conditions and washed under stringent conditions, i e., 0.2×SSC at 65° C. The DNA probe is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) are probed in ExpressHyb hybridization solution (Clontech) and washed at high stringency according to manufacturer's recommendations.

For in situ analysis, various tissues obtained from brains of, e.g., rat, mouse, or human origin, are first frozen on dry ice. Ten-micrometer-thick coronal sections of the tissues are postfixed with 4% formaldehyde in DEPC treated 1×phosphate-buffered saline at room temperature for 10 minutes before being rinsed twice in DEPC 1×phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled (5×10$^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1×Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 µg of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Example 4

EXPRESSION OF A RECOMBINANT HUMAN ABCB9 TRANSPORTER POLYPEPTIDE IN BACTERIAL CELLS

In this example, the human ABCB9 transporter is expressed as a recombinant glutathione-S-transferase (GST) fusion polypeptide in *E. coli* and the fusion polypeptide is isolated and characterized.

Specifically, the human ABCB9 transporter is fused to GST and this fusion polypeptide is expressed in *E. coli*, e.g., strain PEB199. As the human ABCB9 transporter polypeptide is predicted to be approximately 117.2 kDa and GST is predicted to be 26 kDa, the fusion polypeptide is predicted to be approximately 143.2 kDa in molecular weight. Expression of the GST-ABCB9 transporter fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined. If desired, the polypeptide may be prepared in association with a membrane, such as, e.g., a micelle or membrane vesicle using art recognized techniques.

Example 5

EXPRESSION OF RECOMBINANT HUMAN ABCB9 TRANSPORTER POLYPEPTIDE IN MAMMALIAN CELLS

To express the ABCB9 transporter gene in a mammalian cell, e.g., COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire ABCB9 transporter protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the ABCB9 transporter DNA sequence (see, e.g., SEQ ID NO: 3) is amplified by PCR using two primers. The 5' primer contains the restriction site of interest followed by approximately twenty nucleotides of the ABCB9 transporter coding sequence starting from the initiation codon; the 3' end sequence contains complementary sequences to the other restriction site of interest, a translation stop codon, the HA tag or FLAG tag and the last 20 nucleotides of the ABCB9 transporter coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the ABCB9 transporter gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the ABCB9 transporter-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989. The expression of the ABCB9 transporter polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the ABCB9 transporter coding sequence is cloned directly into the polylinker of the pcDNA/Amp vector using the appropriate restriction sites. The resulting plasmid is transfected into COS cells in the manner described above, and the expression of the ABCB9 transporter polypeptide is detected by radiolabelling and immunoprecipitation using an ABCB9 transporter specific monoclonal antibody.

Example 6

IN VITRO AND IN VIVO SCREENING ASSAYS FOR MODULATORS OF A HUMAN ABCB9 TRANSPORTER

In this example, in vitro and in vivo assays for screening modulators of the human ABCB9 transporter molecule are described.

Briefly, the ABCB9 transporter is expressed in a mammalian cell line as described above and a base line for the cellular transport of a reference molecule, e.g., β-amyloid or other small molecule, is established. Cells are then incubated with a test compound and a change in the level of the cellular transport of the reference molecule is determined using standards techniques. A test compound that changes the transport of the detectable reference molecule is then identified as a candidate compound that alters ABCB9 transporter activity. Lead compounds may then be tested on, e.g., cells of neuronal origin or, alternatively, on brain tissue from a test animal. Methods for conducting such an assay are known in the art. Preferably, lead test compounds that inhibit ABCB9-mediated transport of, e.g., β-amyloid are further tested in vivo. Mouse models for various neurological diseases, e.g., amyloid disease, are also known in the art (see, e.g., Hardy et al., (1998) *Science* 282:1075–1079; Goate, el al., (1991) *Nature* 349: 704; Games, et al., (1995) *Nature* 373: 523; and Suzuki, et al., (1994) *Science* 264: 1336).

Alternatively, a transgenic mouse model overexpressing an ABCB9 transporter polypeptide, e.g., the human ABCB9 transporter polypeptide or corresponding murine polypeptide is generated using the techniques described herein. This animal may then be tested directly or used as a cell or tissue source, e.g., brain tissue source, for testing modulators of the human ABCB9 transporter polypeptide. Preferably, the animal is directly tested with a test compound and monitored for a physiological result, e.g., presence of β-amyloid in the cerebral spinal fluid (CSF). In a related extension of this in vivo assay, the animal may be bred with an animal overexpressing a undesired polypeptide, e.g., an amyloid polypeptide, and a change in the transport of the polypeptide is measured (e.g., in the CSF) as compared to a control. Ideally, these test animals are further monitored in the presence or absence of a modulator of the ABCB9 transporter.

Analogously, a transgenic mouse having a genetically disrupted ABCB9 transporter gene (i.e., a so-called knockout mouse) which expresses little or no ABCB9 transporter polypeptide can be made, using standard techniques, to complement the foregoing ABCB9 overexpressing mouse model. Such a mouse model can be used, for example, to examine the biologic contribution of the ABCB9 transporter molecule in, e.g., Aβ transport, or as a negative control. In addition, the mouse model can be used as a source of cells (or tissues) for use in cell-based assays where an ABCB9 transporter null background is desired as, e.g., either a control or for assessing the biologic activity (e.g., for performing structure/function analyses) of an ABCB9 transporter molecule (or other related molecules).

In a modification of the assay, the activity of the ABCB9 transporter is determined regarding the ability of a detectable reference molecule to cross the blood-brain barrier. In yet another modification of the assay, the animal is examined for the prevalence of multidrug resistant cells or tissues, and/or the sensitivity of the animal to cytotoxic drugs suitable for treating a neoplasm.

Accordingly, the foregoing animals represent in vivo assay systems in which to test the ability of an ABCB9 transporter and/or ABCB9 transporter modulator to prevent, treat, or delay the onset of disease.

Example 7

FUNCTIONAL CHARACTERIZATION OF HUMAN ABCB9 TRANSPORTER MOLECULES

In this example, a functional assay was performed to demonstrate that the novel human ABCB9 molecule has transporter activity.

In particular, by expressing the ABCB9 transporter in a cell type engineered to over produce Aβ polypeptide, the ability of ABCB9 to transport Aβ out of the cell into the culture medium, as compared to controls, could be measured. Importantly, neither an irrelevant polypeptide (β-Gal) nor a mutated ABCB9 transporters exhibited this activity.

Briefly, the experiments were performed as follows. First, 293 EBNA cells (InVitrogen, Carlsbad, Calif.) were stably transfected with wild-type Amyloid Precursor Protein and the resultant cells (now referred to as 695 WT6 cells), were cultured in standard medium (i.e., DMEM supplemented with sodium pyruvate (1 mM) and 10% fetal calf serum). Typically, cells were plated at a density of 100,000 cells per well in 35 mm² culture dishes (Falcon™) 18 hours prior to transient transfection experiments.

The cell cultures were then transfected for 48 hrs using a Fugene-6 transfection procedure (Boehringer Mannheim, Laval, QC) using 2 μg of a DNA construct encoding wild type human ABCB9 transporter, or negative controls (i.e., either an irrelevant polypeptide or a non-functional ABCB9 mutant), at a DNA:Fugene-6 ratio of 1:3.

Specifically, the constructs transfected encoded one of the following: 1) wild type human ABCB9 transporter, 2) an irrelevant βGal polypeptide, 3) an inactive mutant form of human ABCB9 having a lysine to arginine amino acid substitution at amino acid position 545 (K545R; SEQ ID NO: 14), or 4) another inactive mutant form of human ABCB9 where an aspartic acid to asparagine amino acid substitution at position 667 has been engineered (D667N: SEQ ID NO: 15). Each of the above constructs was subcloned into, and expressed from, the pcDNA3.1 vector.

Following the 48 hr transfection procedure described above, cell cultures were washed once with warm PBS (37° C.) and then exposed to DMEM supplemented with sodium pyruvate (1 mM) for 4 hrs. After this four hour incubation period the media was removed, the cultures washed once with PBS and then harvested in 100 μl of ice-cold lysis buffer (i.e., 20 mM MOPS (pH 7.2), 5 mM EDTA, 0.01% Nonidet P-40, 75 mM β-glycerol phosphate and a cocktail of protease inhibitors (Boehringer Mannheim, Laval, QC)).

Figure 5:
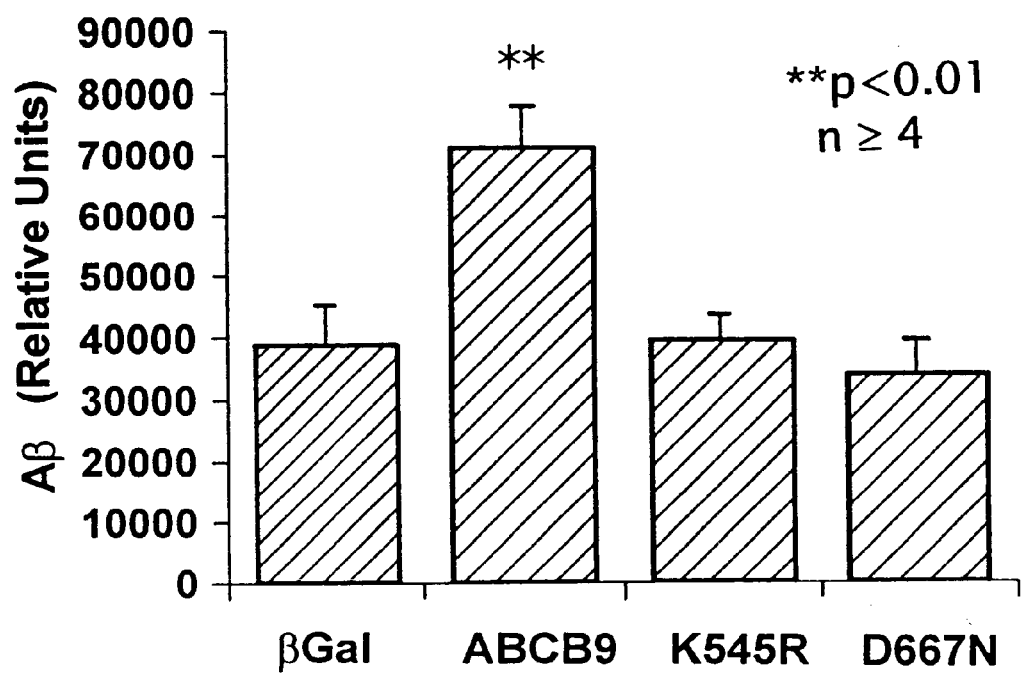
FIG. 5 depicts the effects of the transient transfection of ABCB9 on extracellular levels of Aβ as detected by densitometric analysis of a representative immunoblot. Specifically, mean densitometric values are presented (±SEM) corresponding to extracellular levels of Aβ measured from cells transfected with a construct expressing an irrelevant polypeptide (βGal), human ABCB9 (ABCB9), or one of two different mutant ABCB9 transporters (i.e., K545R(SEQ ID NO: 14) and D667N (SEQ ID NO: 15)). Statistical significance was determined by ANOVA with Tukey's post hoc test at **$p<0.01$ and n=4–7.

To detect the ability of the transfected cells to transport intracellular Aβ into the extracellular milieu, the media form the test and control cultures were retained and centrifuged for 8 min at 13,000×g followed by precipitation of extracellular protein by 10% trichloroacetic acid precipitation (Mills et al., 1997; Connop et al., 1999). Levels of Aβ in the media were quantitated using 16 % Tris-Tricine SDS-PAGE followed by immunoblot analysis using the monoclonal antibody 6E10 (Senetek, Napa, Calif.) specific to an epitope within the first 16 amino acids of the N-terminal region of Aβ. Immunoreactive bands were visualized using ECL detection (Amersham, Oakville, ON) and analyzed by standard densitometric techniques as shown in FIG. 5.

The statistical significance was determined using an ANOVA with Tukey's post hoc analysis. Data are expressed as mean±SEM with *p <0.05 and **p<0.01. n=between 4 and 7 for each treatment group.

The data clearly indicate that only cells transfected with a functional ABCB9 transporter are capable of transporting intracellular Aβ out of the cell. Accordingly, these results demonstrate that at least one important biologic function of ABCB9 is transport of Aβ. Additionally, these experiments demonstrate a working cell-based assay for the screening of compounds that can modulate the activity of a human transporter.

It will be appreciated that with only routine experimentation, this assay may be employed and/or modified to screen for activators or inhibitors of an ABC transporter, e.g., ABCB9, using a high throughput format. Still further, it will be appreciated that modulators identified using the above assay may be candidates not only for the modulation of Ad transport but also for the modulation of multi-drug resistance.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. An isolated nucleic acid molecule comprising either (a) a nucleic acid molecule comprising the nucleotide sequence set forth in SEQ ID NO: 1 or (b) a nucleic acid molecule comprising the nucleotide sequence set forth in SEQ ID NO: 3.

2. An isolated nucleic acid molecule that encodes a polypeptide comprising the amino acid sequence set forth in SEQ ID NO: 2.

3. An isolated nucleic acid molecule comprising a nucleotide sequence that is at least 92% homologous to the nucleotide sequence of SEQ ID NO: 1 or 3 that encodes an ABCB9 transporter polypeptide, wherein the ABCB9 transporter polypeptide retains an ABCB9 transporter activity.

4. An isolated nucleic acid molecule that encodes an ABCB9 transporter polypeptide comprising an amino acid sequence at least about 96% homologous to the amino acid sequence of SEQ ID NO: 2, wherein the ABCB9 transporter polypeptide retains an ABCB9 transporter activity.

5. An isolated nucleic acid molecule comprising a nucleotide sequence which is complementary to the nucleotide sequence of the nucleic acid molecule of any one of claims 1, 2, 3 or 4.

6. An isolated nucleic acid molecule comprising the nucleic acid molecule of any one of claim 1, 2, 3, or 4 and a nucleotide sequence encoding a heterologous polypeptide.

7. An expression vector comprising the nucleic acid molecule of claim 1.

8. A host cell transfected or transformed with the expression vector of claim 7.

9. A method of producing a polypeptide comprising culturing the host cell of claim 8 in an appropriate culture medium to, thereby, produce the polypeptide.

10. An expression vector comprising the nucleic acid molecule of any one of claim 1, 2, 3, or 4.

11. A host cell transfected or transformed with the expression vector of claim 10.

12. A method of producing a polypeptide comprising culturing the host cell according to claim 11 in an appropriate culture medium to, thereby, produce the polypeptide.

13. An expression vector comprising the isolated nucleic acid molecule according to claim 6.

14. A host cell transfected or transformed with the expression vector of claim 13.

15. The isolated nucleic acid molecule according to any one of claim 3 or 4 wherein the ABCB9 transporter activity is the ability to transport β-amyloid across a cell membrane.

* * * * *